United States Patent
Yu et al.

(10) Patent No.: US 11,203,645 B2
(45) Date of Patent: Dec. 21, 2021

(54) GLYCOSYNTHASE VARIANTS FOR GLYCOPROTEIN ENGINEERING AND METHODS OF USE

(71) Applicant: OBI PHARMA, INC., Taipei (TW)

(72) Inventors: Cheng-Der Tony Yu, San Diego, CA (US); Yih Huang Hsieh, Taipei (TW); Yin-Cheng Hsieh, Taipei (TW); Teng-Yi Huang, Taipei (TW); Yi-Chien Tsai, Taipei (TW); Nan-Hsuan Wang, Taipei (TW); Pu-Ling Hu, Taipei (TW)

(73) Assignee: OBI PHARMA, INC., Taipei (TW)

( * ) Notice: Subject to any disclaimer, the term of this patent is extended or adjusted under 35 U.S.C. 154(b) by 0 days.

(21) Appl. No.: 16/454,750

(22) Filed: Jun. 27, 2019

(65) Prior Publication Data

US 2020/0062861 A1 Feb. 27, 2020

Related U.S. Application Data

(60) Provisional application No. 62/690,669, filed on Jun. 27, 2018.

(51) Int. Cl.
| | | |
|---|---|---|
| C07K 16/30 | (2006.01) | |
| C07K 16/32 | (2006.01) | |
| C12N 15/85 | (2006.01) | |
| G01N 30/02 | (2006.01) | |
| G01N 30/38 | (2006.01) | |

(52) U.S. Cl.
CPC .......... *C07K 16/3053* (2013.01); *C07K 16/32* (2013.01); *C12N 15/85* (2013.01); *G01N 30/02* (2013.01); *C07K 2317/41* (2013.01); *C12Y 302/02022* (2013.01); *G01N 2030/027* (2013.01); *G01N 2030/386* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| RE30,985 E | 6/1982 | Cartaya |
| 4,419,446 A | 12/1983 | Howley et al. |
| 4,522,811 A | 6/1985 | Eppstein et al. |
| 4,560,655 A | 12/1985 | Baker |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,849,222 A | 7/1989 | Broaddus |
| 4,927,762 A | 5/1990 | Darfler |
| 4,943,533 A | 7/1990 | Mendelsohn et al. |
| 4,965,199 A | 10/1990 | Capon et al. |
| 4,975,278 A | 12/1990 | Senter et al. |
| 5,004,697 A | 4/1991 | Pardridge |
| 5,057,540 A | 10/1991 | Kensil et al. |
| 5,061,620 A | 10/1991 | Tsukamoto et al. |
| 5,100,669 A | 3/1992 | Hyon et al. |
| 5,112,596 A | 5/1992 | Malfroy-Camine |
| 5,122,469 A | 6/1992 | Mather et al. |
| 5,212,290 A | 5/1993 | Vogelstein et al. |
| 5,264,365 A | 11/1993 | Georgiou et al. |
| 5,268,164 A | 12/1993 | Kozarich et al. |
| 5,500,362 A | 3/1996 | Robinson et al. |
| 5,506,206 A | 4/1996 | Kozarich et al. |
| 5,508,192 A | 4/1996 | Georgiou et al. |
| 5,545,806 A | 8/1996 | Lonberg et al. |
| 5,545,807 A | 8/1996 | Surani et al. |

(Continued)

FOREIGN PATENT DOCUMENTS

| | | |
|---|---|---|
| CN | 1871025 A | 11/2006 |
| CN | 103108654 A | 5/2013 |

(Continued)

OTHER PUBLICATIONS

NCBI GenBank: AN 126084.1 (submitted Jun. 8, 2016). (Year: 2016).*
BLAST alignment of GenBank AN 126084.1 and SEQ ID No. 1 (downloaded Nov. 20, 2020). (Year: 2020).*
Chuang, Po-Kai, et al. "Signaling pathway of globo-series glycosphingolipids and β1, 3-galactosyltransferase V (β3GalT5) in breast cancer." Proceedings of the National Academy of Sciences 116.9 (2019):3518-3523.
International Search Report/Written Opinion dated Oct. 18, 2019 in counterpart application PCT/US2019/035168, 13 pages.

(Continued)

*Primary Examiner* — Anand U Desai
(74) *Attorney, Agent, or Firm* — Prosyla Group PC

(57) ABSTRACT

The present disclosure relates to novel glycosynthase enzymes for glycoprotein engineering and/or homogeneous antibody remodeling. The enzyme variants, termed EndoSd-D232M and EndoSz-D234M, contain the glycan conjugation and/or modification activity at the conserved N297 glycosylation site of Fc region of an exemplary antibody. It has been demonstrated that the glycosynthase activities of EndoSd-D232M and EndoSz-D234M can be applied to various mAbs targeting different receptors, including, but not limited to, Globo H, SSEA-4, SSEA-3 series of receptors (OBI-888; Globo H ganglioside), Herceptin (Her 2 receptor), Perj eta (Her 2 receptor) and Vectibix (EGFR receptor). It has been found that both mAb-GlcNAc and mAb-GlucNAc(F) were suitable substrates for both EndoSd-D232M and EndoSz-D234M. The ADCC assay of related products, OBI-888-G2S2 and Herceptin-G2S2, showed that the remodeled homogeneous antibody, mAb-G2S2, has an increased relative activity ranging from 3 to 26 folds.

15 Claims, 7 Drawing Sheets

Specification includes a Sequence Listing.

(56) References Cited

U.S. PATENT DOCUMENTS

| | | | |
|---|---|---|---|
| 5,565,332 | A | 10/1996 | Hoogenboom et al. |
| 5,569,825 | A | 10/1996 | Lonberg et al. |
| 5,571,894 | A | 11/1996 | Wels et al. |
| 5,580,717 | A | 12/1996 | Dower et al. |
| 5,587,458 | A | 12/1996 | King et al. |
| 5,625,126 | A | 4/1997 | Lonberg et al. |
| 5,633,425 | A | 5/1997 | Lonberg et al. |
| 5,641,870 | A | 6/1997 | Rinderknecht et al. |
| 5,648,237 | A | 7/1997 | Carter |
| 5,661,016 | A | 8/1997 | Lonberg et al. |
| 5,686,416 | A | 11/1997 | Kozarich et al. |
| 5,733,743 | A | 3/1998 | Johnson et al. |
| 5,804,396 | A | 9/1998 | Plowman |
| 5,814,344 | A | 9/1998 | Tice et al. |
| 5,821,337 | A | 10/1998 | Carter et al. |
| 5,840,523 | A | 11/1998 | Simmons et al. |
| 5,869,046 | A | 2/1999 | Presta et al. |
| 5,891,996 | A | 4/1999 | Mateo de Acosta del Rio et al. |
| 6,004,940 | A | 12/1999 | Marasco et al. |
| 6,027,888 | A | 2/2000 | Georgiou et al. |
| 6,083,715 | A | 7/2000 | Georgiou et al. |
| 6,265,150 | B1 | 7/2001 | Terstappen et al. |
| 6,329,173 | B1 | 12/2001 | Marasco et al. |
| 6,524,584 | B2 | 2/2003 | Kensil |
| 6,544,952 | B1 | 4/2003 | Danishefsky et al. |
| 6,703,019 | B1 | 3/2004 | Malfroy-Camine |
| 7,595,292 | B2 | 9/2009 | Brocchini et al. |
| 8,268,969 | B2 | 9/2012 | Wong et al. |
| 9,850,473 | B2 | 12/2017 | Wang |
| 2002/0025313 | A1 | 2/2002 | Micklus et al. |
| 2002/0038086 | A1 | 3/2002 | Hynynen et al. |
| 2002/0065259 | A1 | 5/2002 | Schatzberg et al. |
| 2003/0073713 | A1 | 4/2003 | Schoenhard |
| 2003/0083299 | A1 | 5/2003 | Ferguson |
| 2003/0104402 | A1 | 6/2003 | Zauderer et al. |
| 2003/0129186 | A1 | 7/2003 | Beliveau et al. |
| 2003/0153492 | A1 | 8/2003 | Danishefsky et al. |
| 2003/0162695 | A1 | 8/2003 | Schatzberg et al. |
| 2004/0018194 | A1 | 1/2004 | Francisco et al. |
| 2004/0131692 | A1 | 7/2004 | Kreuter et al. |
| 2004/0204354 | A1 | 10/2004 | Nelson et al. |
| 2004/0208884 | A1 | 10/2004 | Danishefsky et al. |
| 2004/0229310 | A1 | 11/2004 | Simmons |
| 2004/0247608 | A1 | 12/2004 | Krantz et al. |
| 2005/0048572 | A1 | 3/2005 | Reilly et al. |
| 2005/0089473 | A1 | 4/2005 | Black et al. |
| 2005/0124533 | A1 | 6/2005 | Schatzberg et al. |
| 2006/0035267 | A1 | 2/2006 | Livingston et al. |
| 2007/0059769 | A1 | 3/2007 | Blixt et al. |
| 2009/0317411 | A1 | 12/2009 | Wong et al. |
| 2010/0136042 | A1 | 6/2010 | Wong et al. |
| 2010/0166790 | A1 | 7/2010 | Agadjanyan et al. |
| 2010/0286035 | A1 | 11/2010 | Ohtaki et al. |
| 2011/0117009 | A1 | 5/2011 | Kratz et al. |
| 2012/0237532 | A1 | 9/2012 | Olbrich et al. |
| 2012/0294859 | A1 | 11/2012 | Goletz et al. |
| 2012/0321583 | A1 | 12/2012 | Yurkovetskiy et al. |
| 2012/0328646 | A1 | 12/2012 | Wong et al. |
| 2013/0095173 | A1 | 4/2013 | Danishefsky et al. |
| 2013/0232589 | A1 | 9/2013 | Papkoff et al. |
| 2014/0363455 | A1 | 12/2014 | Stull et al. |
| 2015/0030669 | A1 | 1/2015 | Platscher et al. |
| 2015/0087814 | A1 | 3/2015 | Wang et al. |
| 2015/0297696 | A1 | 10/2015 | Yu et al. |
| 2015/0316556 | A1 | 11/2015 | Hardt et al. |
| 2015/0344551 | A1 | 12/2015 | Wong et al. |
| 2016/0074522 | A1 | 3/2016 | Okuda et al. |
| 2016/0102151 | A1 | 4/2016 | Wong et al. |
| 2016/0339089 | A1 | 11/2016 | Yu et al. |
| 2017/0067885 | A1 | 3/2017 | Yu et al. |
| 2017/0101462 | A1 | 4/2017 | Yu et al. |
| 2017/0283488 | A1 | 10/2017 | Yu et al. |
| 2017/0304419 | A1 | 10/2017 | Yu et al. |
| 2017/0335281 | A1 | 11/2017 | Loew et al. |
| 2018/0028629 | A1 | 2/2018 | Yu et al. |
| 2018/0193481 | A1 | 7/2018 | Chang et al. |
| 2018/0208915 | A1 | 7/2018 | Kawaguchi et al. |
| 2018/0339061 | A1 | 11/2018 | Yu et al. |

FOREIGN PATENT DOCUMENTS

| | | |
|---|---|---|
| EP | 0404097 A2 | 12/1990 |
| EP | 1391213 A1 | 2/2004 |
| EP | 2993182 A1 | 3/2016 |
| JP | 2006-507233 A | 3/2006 |
| KR | 10-2012-0014238 A | 2/2012 |
| WO | WO 87/00195 A1 | 1/1987 |
| WO | WO 90/03184 A1 | 4/1990 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/09690 A2 | 6/1992 |
| WO | WO 93/01161 A1 | 1/1993 |
| WO | WO 93/06213 A1 | 4/1993 |
| WO | WO 93/007861 A1 | 4/1993 |
| WO | WO 93/08829 A1 | 5/1993 |
| WO | WO 93/16185 A2 | 8/1993 |
| WO | WO 94/04690 A1 | 3/1994 |
| WO | WO 94/011026 A2 | 5/1994 |
| WO | WO 95/011010 A1 | 4/1995 |
| WO | WO 96/07754 A1 | 3/1996 |
| WO | WO 96/11711 A1 | 4/1996 |
| WO | WO 96/30347 A1 | 10/1996 |
| WO | WO 96/33735 A1 | 10/1996 |
| WO | WO 96/33978 A1 | 10/1996 |
| WO | WO 96/33980 A1 | 10/1996 |
| WO | WO 96/34096 A1 | 10/1996 |
| WO | WO 96/40210 A1 | 12/1996 |
| WO | WO 97/38983 A1 | 10/1997 |
| WO | WO 98/24893 A2 | 6/1998 |
| WO | WO 98/36772 A1 | 8/1998 |
| WO | WO 98/43960 A1 | 10/1998 |
| WO | WO 99/06378 A1 | 2/1999 |
| WO | WO 99/06396 A1 | 2/1999 |
| WO | WO 99/09016 A1 | 2/1999 |
| WO | WO 99/042130 A1 | 8/1999 |
| WO | WO 2000/41720 A1 | 7/2000 |
| WO | WO 2000/48630 A1 | 8/2000 |
| WO | WO-2000/49412 A1 | 8/2000 |
| WO | WO 2003/015796 A1 | 2/2003 |
| WO | WO 2003/043583 A2 | 5/2003 |
| WO | WO 2003/077945 A1 | 9/2003 |
| WO | WO 2004/011476 A1 | 2/2004 |
| WO | WO 2004/032828 A2 | 4/2004 |
| WO | WO 2005/007197 A2 | 1/2005 |
| WO | WO 2006/105152 A2 | 10/2006 |
| WO | WO 2006/134423 A2 | 12/2006 |
| WO | WO 2007/026190 A2 | 3/2007 |
| WO | WO 2007/044515 A1 | 4/2007 |
| WO | WO 2009/035494 A2 | 3/2009 |
| WO | WO 2009/126737 A2 | 10/2009 |
| WO | WO-2011/156774 A2 | 12/2011 |
| WO | WO 2014/107652 A2 | 7/2014 |
| WO | WO 2014/178195 A1 | 11/2014 |
| WO | WO 2015/143123 A2 | 9/2015 |
| WO | WO 2015/157629 A2 | 10/2015 |
| WO | WO 2015/159118 A2 | 10/2015 |
| WO | WO 2016/026742 A1 | 2/2016 |
| WO | WO 2016/044326 A1 | 3/2016 |
| WO | WO 2016/118961 A1 | 7/2016 |
| WO | WO 2016/123593 A1 | 8/2016 |
| WO | WO 2017/041027 A1 | 3/2017 |
| WO | WO 2017/062792 A1 | 4/2017 |
| WO | WO 2017/172990 A1 | 10/2017 |
| WO | WO 2018/022933 A1 | 2/2018 |
| WO | WO 2018/023121 A1 | 2/2018 |
| WO | WO 2018/094414 A1 | 5/2018 |

OTHER PUBLICATIONS

International Search Report dated Dec. 3, 2019 in counterpart application PCT/US2019/039414, 5 pages.

(56) References Cited

OTHER PUBLICATIONS

Ragupathi, Govindaswami, et al. "A novel and efficient method for synthetic carbohydrate conjugate vaccine preparation: synthesis of sialyl Tn-KLH conjugate using a 4-(4-N-maleimidomethyl) cyclohexane-1-carboxyl hydrazide (MMCCH) linker arm." Glycoconjugate Journal 15.3 (1998): 217-221.
Abrahmsén et al., "Analysis of signals for secretion in the staphylococcal protein A gene," EMBO J., Dec. 30, 1985, 4(13B):3901-3906.
Allen, P. Z. et al., Immunochemical Studies on a Sophorosyl-Azoprotein Conjugate, Biochemistry, 1967, 6(10), 3029-3036.
Arié, et al., "Chaperone function of FkpA, a heat shock prolyl isomerase, in the periplasm of *Escherichia coli*," Mol. Microbiol., Jan. 2001, 39(1):199-210.
Arigi, Emma, et al. "Design of a covalently bonded glycosphingolipid microarray." Glycoconjugate Journal 29.1 (2012): 1-12.
Avery, Oswald et al., Chemo-Immunological Studies on Conjugated Carbohydrate-Proteins, J. Exp. Med., 1929, 50, 533-550.
Bachmann, Cellular and Molecular Biology, vol. 2, Chapter 72: Derivations and Genotypes of Some Mutant Derivatives of *Escherichia coli* K-12, Neidhardt et al., eds., 1987, pp. 1190-1219, American Society for Microbiology, Washington, D.C.
Baldwin et al., "Monoclonal antibodies in cancer treatment," Lancet, Mar. 15, 1986, 327(8481):603-605.
Barbas et al., "Assembly of combinatorial antibody libraries on phage surfaces: the gene III site," Proc. Natl. Acad. Sci. U.S.A., Sep. 15, 1991, 88(18):7978-7982.
Barbas, C.F. et al., "Semisynthetic combinatorial antibody libraries: a chemical solution to the diversity problem" Proc. Natl. Acad. Sci. USA, May 15, 1992, 89(10): 4457-4461.
Barbas et al., "In vitro evolution of a neutralizing human antibody to human immunodeficiency virus type 1 to enhance affinity and broaden strain cross-reactivity," Proc. Nat. Acad. Sci. U.S.A., Apr. 26, 1994, 91(9):3809-3813.
Barnes et al., "Methods for growth of cultured cells in serum-free medium," Anal. Biochem., Mar. 1, 1980, 102(2):255-270.
Bass et al., "Hormone phage: an enrichment method for variant proteins with altered binding properties," Proteins, 1990, 8(4):309-314.
Berenbaum, M. C., What is Synergy?, Pharmacol. Rev. 41(2):93-141, 1989.
Bergman, Jan, and Lennart Venemalm. "Efficient synthesis of 2-chloro-, 2-bromo-, and 2-iodoindole." The Journal of Organic Chemistry 57.8 (1992):2495-2497.
Bertozzi, CR et al., Glycans in Cancer and Inflammation-Potential for Therapeutics and Diagnostics, Nat Rev Drug Discovery, 2005, 4, 477-488.
Bhaskar, Vinay, et al. "E-selectin up-regulation allows for targeted drug delivery in prostate cancer." Cancer Research 63.19 (2003): 6387-6394.
Bird, R.E., et al., "Single-chain antigen-binding proteins" Science Oct. 21, 1988;242(4877):423-426.
Bliss, C.I., The Calculation of Microbial Assays, Bacterial. Rev. 20:243-258, 1956.
Bobo et al., "Convection-enhanced delivery of macromolecules in the brain," Proc. Natl. Acad. Sci. U.S.A., Mar. 15, 1994, 91(6) 2076-2080.
Boerner et al., "Production of antigen-specific human monoclonal antibodies from in vitro-primed human splenocytes," J. Immunol., Jul. 1, 1991, 147(1):86-95.
Borisy, Alexis et al., Systematic Discovery of Multicomponent Therapeutics, Proc. Natl. Acad. Sci. 100(13):7977-7982, 2003.
Bosse, Folkert et al., Linear Synthesis of the Tumor-Associated Carbohydrate Antigens Globo-H, SSEA-3, and Gb3, J Org Chem. 67(19):6659-70, 2002.
Bothmann et al., "The periplasmic *Escherichia coli* peptidylprolyl cis,trans-isomerase FkpA. I. Increased functional expression of antibody fragments with and without cis-prolines," J. Biol. Chem., Jun. 2, 2000, 275(22):17100-17105.

Bowie, JU et al., Deciphering the Message in Protein Sequences: Tolerance to Amino Acid Substitutions, Science, 247: 1306-1310 (1990).
Bremer, E. G., et al. "Characterization of a glycosphingolipid antigen defined by the monoclonal antibody MBr1 expressed in normal and neoplastic epithelial cells of human mammary gland." Journal of Biological Chemistry 259.23 (1984): 14773-14777.
Brennan et al., "Preparation of bispecific antibodies by chemical recombination of monoclonal immunoglobulin G1 fragments," Science, Jul. 5, 1985, 229(4708):81-83.
Brodeur et al., Monoclonal Antibody Production Techniques and Applications, Chapter 4: Mouse-Human Myeloma Partners for the Production of Heterohybridomas, Schook, ed., 1987, pp. 51-63, Marcel Dekker, Inc., New York.
Brüggemann et al., "Designer mice: the production of human antibody repertoires in transgenic animals," Year in Immunol., 1993, 7:33-40.
Carter et al., "High level *Escherichia coli* expression and production of a bivalent humanized antibody fragment," Nature Biotechnology, Feb. 1992, 10(2):163-167.
Carter et al., "Humanization of an anti-p185HER2 antibody for human cancer therapy," Proc. Natl. Acad. Sci. U.S.A., May 15, 1992, 89(10):4285-4289.
Casset, Florence, et al. "A peptide mimetic of an anti-CD4 monoclonal antibody by rational design." Biochemical and Biophysical Research Communications 307.1 (2003): 198-205.
Chang et al., "Potent immune-modulating and anticancer effects of NKT cell stimulatory glycolipids," Proc. Natl. Acad. Sci. USA, Jun. 19, 2007, 104(25):10299-10304.
Chang et al., "Expression of Globo H and SSEA3 in breast cancer stem cells and the involvement of fucosyl transferases 1 and 2 in Globo H synthesis," Proc. Natl. Acad. Sci. U.S.A., Aug. 19, 2008, 105(33):11667-11672.
Chen et al., "Chaperone activity of DsbC," J. Bio. Chem., Jul. 9, 1999, 274(28):19601-19605.
Chen et al., "Selection and analysis of an optimized anti-VEGF antibody: crystal structure of an affinity-matured Fab in complex with antigen," J. Mol. Biol., Nov. 5, 1999, 293(4):865-881.
Chen et al., "Selective killing of transformed cells by cyclin/cyclin-dependent kinase 2 antagonists," Proc. Natl. Acad. Sci. U.S.A., Apr. 13, 1999, 96(8):4325-4329.
Chen, Wei, et al. "Determination of thiols and disulfides via HPLC quantification of 5-thio-2-nitrobenzoic acid." Journal of Pharmaceutical and Biomedical Analysis 48.5 (2008): 1375-1380.
Cheung, Sarah et al., Stage-Specific Embryonic Antigen-3 (SSEA-3) and β3GalT5 are cancer specific and Significant Markers for Breast Cancer Stem Cells, PNAS, Jan. 26, 2016, vol. 113, No. 4, pp. 960-965.
Chothia et al., "Canonical structures for the hypervariable regions of immunoglobulins," J. Mol. Biol., Aug. 20, 1987, 196(4):901-917.
Chou, Ting-Chao and Talalay, Paul, A Simple Generalized Equation for the Analysis of Multiple Inhibitions of Michaelis-Menten Kinetic Systems, J. Biol. Chem. 252:6438-6442, 1977.
Chou, T. C. and Talalay, P., Quantitative Analysis of Dose-Effect Relationships: The Combined Effects of Multiple Drugs or Enzyme Inhibitors. Adv. Enzyme Regul. 22:27-55, 1984.
Clackson et al., "Making antibody fragments using phage display libraries," Nature, Aug. 15, 1991, 352(6336):624-628.
ClinicalTrials.gov [Internet]. Bethesda (MD): National Library of Medicine (US). Jan. 24, 2012—. Trial of Active Tmunotherapy with Globo H-KLH (OPT-822) in Metastatic Breast Cancer Subjects); Jan. 24, 2012 [cited Oct. 11, 2017]; [about 7 screens]. Available from: https:clinicaltrials.gov/ct2/show/NCT01516307.
Clynes, Raphael, et al. "Fc receptors are required in passive and active immunity to melanoma." Proceedings of the National Academy of Sciences 95.2 (1998): 652-656.
Colman, P.M., "Effects of amino acid sequence changes on antibody-antigen interactions," Research in Immunology 145:33-36, 1994.
Cunningham et al., "High-resolution epitope mapping of hGH-receptor interactions by alanine-scanning mutagenesis," Science, Jun. 2, 1989, 244(4908):1081-1085.
Cuzick, J., et al. "Overview of the main outcomes in breast-cancer prevention trials." The Lancet 361.9354 (2003): 296-300.

(56) References Cited

OTHER PUBLICATIONS

Danishefsky, Samuel J., et al. "Development of Globo-H cancer vaccine." Accounts of Chemical Research 48.3 (2015): 643-652.
De Pascalis, Roberto, et al. "Grafting of "abbreviated" complementarity-determining regions containing specificity-determining residues essential for ligand contact to engineer a less immunogenic humanized monoclonal antibody." The Journal of Immunology 169.6 (2002): 3076-3084.
Doronina, Svetlana O., et al. "Development of potent monoclonal antibody auristatin conjugates for cancer therapy." Nature Biotechnology 21.7 (2003):778-784.
Eller, Chelcie et al., Human Cancer Antigen Globo H Is a Cell-Surface Ligand for Human Ribonuclease 1, ACS Central Science. vol. 1, p. 181-90, Jul. 13, 2015.
Embleton et al., "In-cell PCR from mRNA: amplifying and linking the rearranged immunoglobulin heavy and light chain V-genes within single cells," Nucl. Acids Res., Aug. 11, 1992, 20(15):3831-3837.
Engels et al., "Gene synthesis [new synthetic methods (77)]," Angew. Chem. Int. Ed. Engl., Jun. 1989, 28(6):716-734.
Evans, T. R. J., and S. B. Kaye. "Vaccine therapy for cancer—fact or fiction?" Q J Med 92.6 (1999): 299-307.
Extended European Search Report, Application No. 15842660.1, dated Mar. 12, 2018, 9 pages.
Extended European Search Report from corresponding European App. No. 16843131.0, dated Feb. 14, 2019, 13 Pages.
Fellouse et al., "Synthetic antibodies from a four-amino-acid code: a dominant role for tyrosine in antigen recognition," Proc. Natl. Acad. Sci. U.S.A., Aug. 24, 2004, 101(34):12467-12472.
Feng, Li. "Probing lipid-protein interactions using lipid microarrays." Prostaglandins & other lipid mediators 77.1-4 (2005): 158-167.
Fielder, R. J. et al., An Immunogenic Polysaccharide-Protein Conjugate, J. Immunol., 1970, 105(1), 265-267.
Fishwild et al., "High-avidity human IgGk monoclonal antibodies from a novel strain of minilocus transgenic mice," Nature Biotechnol., Jul. 1996, 14(7):845-851.
Fitzgerald, Jonathan et al., Systems Biology and Combination Therapy in the Quest for Clinical Efficacy, Nature Chem. Biol. 2(9):458-466, 2006.
Francisco, Joseph A., et al. "cAC10-vcMMAE, an anti-CD30-monomethyl auristatin E conjugate with potent and selective anti-tumor activity." Blood 102.4 (2003): 1458-1465.
Galfrè et al., "Preparation of monoclonal antibodies: strategies and procedures," Methods Enzymol., 1981, 73(Pt B):3-46.
Gazzano-Santoro, Hélène, et al. "A non-radioactive complement-dependent cytotoxicity assay for anti-CD20 monoclonal antibody." Journal of Immunological Methods 202.2 (1997): 163-171.
Gijsen, H.J. et al., Recent Advances in the Chemoenzymatic Synthesis of Carbohydrates and Carbohydrate Mimetics, Chem. Rev., 96, 443-473, 1996.
Gilewski, Teresa et al., Immunization of Metastatic Breast Cancer Patients with a Fully Synthetic Globo H Conjugate: A Phase I Trial, Proc Natl Acad Sci USA 98:3270-3275, 2001.
Gill et al., "Direct brain infusion of glial cell line-derived neurotrophic factor in Parkinson disease," Nature Med., May 2003, 9(5):589-595 and Addendum from Apr. 2006, 12(4):479.
Goding, Monoclonal Antibodies: Principles and Practice 2nd ed., Chapter 3: Production of Monoclonal Antibodies, 1986, pp. 59-103, Academic Press, London.
Goebel, Walther et al., Chemo-immunological Studies on Conjugated Carbohydrate-Proteins, J. Exp. Med., 1929, 50, 521-531.
Gonnet, GH et al., Exhaustive Matching of the Entire Protein Sequence Database, Science 256: 1443-1445 (1992).
Graham et al., "Characteristics of a human cell line transformed by DNA from human adenovirus type 5," J. Gen. Virol., Jul. 1977, 36(1):59-72.
Gram et al., "In vitro selection and affinity maturation of antibodies from a naive combinatorial immunoglobulin library," Proc. Natl. Acad. Sci. U.S.A., Apr. 15, 1992, 89(8):3576-3580.
Grant, Oliver C., et al. "Presentation, presentation, presentation! Molecular-level insight into linker effects on glycan array screening data." Glycobiology 24.1 (2014): 17-25.
Greco, William et al., The Search for Synergy: A Critical Review From a Response Surface Perspective, Pharmacol. Rev. 47(2) :331-385, 1995.
Griffiths et al., "Human anti-self antibodies with high specificity from phage display libraries," EMBO J., Feb. 1993, 12(2):725-734.
Gruber et al., "Efficient tumor cell lysis mediated by a bispecific single chain antibody expressed in *Escherichia coli*," J. Immunol., Jun. 1, 1994, 152(11):5368-5374.
Guss et al., "Structure of the IgG-binding regions of streptococcal protein G," EMBO J., Jul. 1986, 5(7):1567-1575.
Hakomori et al., "Glycosphingolipid antigens and cancer therapy," Chem. & Biol., Feb. 1997, 4(2):97-104.
Hakomori, Sen-Itiroh, Tumor-associated carbohydrate antigens defining tumor malignancy: Basis for development of and-cancer vaccines, 2001, Advances in Experimental Medicine and Biology. 491 :369-402.
Ham, Richard et al., Media and Growth Requirements, Meth. Enz 58, 44-93 (1979).
Hammerling et al., "Production of antibody-producing hybridomas in the rodent systems." in: Monoclonal Antibodies and T-Cell Hybridomas, 563-587, 1981, Elsevier North-Holland.
Hara et al., "Overproduction of penicillin-binding protein 7 suppresses thermosensitive growth defect at low osmolarity due to an spr mutation of *Escherichia coli*," Microbial Drug Resistance, Spring 1996, 2(1):63-72.
Harris, "Production of humanized monoclonal antibodies for in vivo imaging and therapy," Biochem. Soc. Transactions, Nov. 1995, 23(4):1035-1038.
Harris, J. Robin, et al. "Keyhole limpet hemocyanin (KLH), II: Characteristic reassociation properties of purified KLH1 and KLH2." Micron 28.1 (1997): 43-56.
Harris, J. R., and J. Mark 1. "Keyhole limpet hemocyanin (KLH): a biomedical review." Micron 30.6 (1999): 597-623.
Hawkins et al., "Selection of phage antibodies by binding affinity. Mimicking affinity maturation," J. Mol. Biol., 1992, 226(3):889-896.
Heffernan, Michael J., et al. "In vivo efficacy of a chitosan/IL,-12 adjuvant system for protein-based vaccines." Biomaterials 32.3 (2011): 926-932.
Hernández-Ledesma, Blanca, Chia-Chien Hsieh, and O. Ben. "Lunasin, a novel seed peptide for cancer prevention." Peptides 30.2 (2009): 426-430.
Himmelspach, K. et al., Use of 1-(m-aminophenyl)flavazoles for the Preparation of Immunogens with Oligosaccharide Determinant Groups, Eur. J. Immunol., 1971, 1(2), 106-112.
Hinman et al., "Preparation and characterization of monoclonal antibody conjugates of the calicheamicins: a novel and potent family of antitumor antibiotics," Cancer Res., Jul. 15, 1993, 53(14):3336-3342.
Hirabayashi, J. et al., Oligosaccharide Microarrays for Glycomics, Trends in Biotechnology 21 (4): 141-143, 2003.
Hirano, Fumiya, et al. "Blockade of B7-H1 and PD-1 by monoclonal antibodies potentiates cancer therapeutic immunity." Cancer Research 65.3 (2005): 1089-1096.
Hogrefe, H.H. et al., "A bacteriophage lambda vector for the cloning and expression of immunoglobulin Fab fragments on the surface of filamentous phage" Gene, 1993, 128(1): 119-126.
Holliger et al., "'Diabodies': small bivalent and bispecific antibody fragments," Proc. Natl. Acad. Sci. U.S.A., Jul. 15, 1993, 90(14):6444-6448.
Holm, Patrik, Rozbeh Jafari, and Birgitta E. Sundström. "Functional mapping and single chain construction of the anti-cytokeratin 8 monoclonal antibody TS1." Molecular Immunology 44.6 (2007): 1075-1084.
Hoogenboom et al., "By-passing immunisation: Human antibodies from synthetic repertoires of germline VH gene segments rearranged in vitro," J. Mol. Biol., Sep. 20, 1992, 227(2):381-388.

(56) References Cited

OTHER PUBLICATIONS

Hoogenboom et al., "Multi-subunit proteins on the surface of filamentous phage: methodologies for displaying antibody (Fab) heavy and light chains," Nucl. Acids Res., Aug. 11, 1991 19(15):4133-4137.
Huang, Cheng-Yuan et al., Carbohydrate Microarray for Profiling the Antibodies Interacting with Globo H Tumor Antigen, Proc Natl Acad Sci, 103:15-20, 2006.
Huang, Yen-Lin, and Chung-Yi Wu. "Carbohydrate-based vaccines: challenges and opportunities." Expert Review of Vaccines 9.11 (2010): 1257-1274.
Huang, Yen-Lin, et al. "Carbohydrate-based vaccines with a glycolipid adjuvant for breast cancer." Proceedings of the National Academy of Sciences 110.7 (2013): 2517-2522.
Hurle et al., "Protein engineering techniques for antibody humanization," Curr. Opin. Biotechnol., Aug. 1994, 5(4):428-433.
Huston, James et al, "Protein Engineering of Antibody Binding Sites: Recovery of Specific Activity in an Anti-Digoxin Single-Chain Fv Analogue Produced in *Escherichia coli*" Proc. Natl. Acad. Sci. USA, 1988, 85:5879-5883.
International Search Report dated Jan. 8, 2016 in counterpart application PCT/IB2014/002744, 3 pages.
International Search Report and Written Opinion of the International Searching Authority, from corresponding International Patent Application No. PCT/US2015/050270, dated Dec. 15, 2015, 14 Pages.
International Search Report and Written Opinion of the International Searching Authority, from corresponding International Patent Application No. PCT/US16/50252, dated Nov. 17, 2016, 12 Pages.
International Search Report and Written Opinion dated Jul. 7, 2017, from corresponding International Patent Application No. PCT/US2017/024853, by Yu, Cheng-Der Tony et al., "Antibodies, Pharmaceutical Compositions and Methods", filed Mar. 29, 2017, 21 pages.
International Search Report/Written Opinion dated Oct. 31, 2017 in counterpart PCT Application No. PCT/US2017/044244, 13 pages.
International Search Report dated Nov. 28, 2017 in counterpart application PCT/US2017/044713, 6 pages.
International Search Report/Written Opinion dated Mar. 12, 2018 in counterpart PCT Application No. PCT/US17/062886, 22 pages.
Jackson et al., "In vitro antibody maturation: Improvement of a high affinity, neutralizing antibody against IL-1β," J. Immunol., Apr. 1, 1995, 154(7):3310-3319.
Jakobovits et al., "Analysis of homozygous mutant chimeric mice: deletion of the immunoglobulin heavy-chain joining region blocks B-cell development and antibody production," Proc. Natl. Acad. Sci. U.S.A., Mar. 15, 1993, 90(6):2551-2555.
Jakobovits et al., "Germ-line transmission and expression of a human-derived yeast artificial chromosome," Nature, Mar. 18, 1993, 362(6417):255-258.
Jeon, Insik et al., A Practical Total Synthesis of Globo-H for Use in Anticancer Vaccines, J. Org. Chem., 2009, 74(21), pp. 8452-8455.
Jones et al., "Rapid PCR-cloning of full-length mouse immunoglobulin variable regions," Nature Biotechnol., Jan. 1991, 9(1):88-89.
Jones et al., "Replacing the complementarity-determining regions in a human antibody with those from a mouse," Nature, May 29-Jun. 4, 1986, 321(6069):522-525.
Jones, "Analysis of polypeptides and proteins," Adv. Drug Delivery Rev., Jan.-Apr. 1993, 10(1):29-90.
Kam et al., "Carbon nanotubes as multifunctional biological transporters and near-infrared agents for selective cancer cell destruction," Proc. Natl. Acad. Sci. U.S.A., Aug. 16, 2005, 102(33):11600-11605.
Kannagi, Reiji, et al. "Stage-specific embryonic antigens (SSEA-3 and-4) are epitopes of a unique globo-series ganglioside isolated from human teratocarcinoma cells." EMBO Journal 2.12 (1983): 2355-2361.
Kannagi et al., "New globoseries glycosphingolipids in human teratocarcinoma reactive with the monoclonal antibody directed to a developmentally regulated antigen, stage-specific embryonic antigen 3," J. Biol. Chem., Jul. 25, 1983, 258(14):8934-8942.
Klussman, Kerry, et al. "Secondary mAb-vcMMAE conjugates are highly sensitive reporters of antibody internalization via the lysosome pathway." Bioconjugate chemistry 15.4 (2004): 765-773.
Koeller, Kathryn et al., Enzymes for Chemical Synthesis, Nature, 409, 232-240, 2001.
Köhler et al., "Continuous cultures of fused cells secreting antibody of predefined specificity," Nature, Aug. 7, 1975, 256(5517):495-497.
Komenaka, Ian, Heidi Hoerig, and Howard L. Kaufman. "Immunotherapy for melanoma." Clinics in Dermatology 22.3 (2004): 251-265.
Konecny, G. et al., Drug Interactions and Cytotoxic Effects of Paclitaxel in Combination with Carboplatin, Epirubicin, Gemcitabine or Vinorelbine in Breast Cancer Cell Lines and Tumor Samples, Breast Cancer Res. and Treatment 67:223-233, 2001.
Kontermann, "Intrabodies as therapeutic agents," Methods, Oct. 2004, 34(2):163-170.
Kostelny et al., "Formation of a bispecific antibody by the use of leucine zippers," J. Immunol., Mar. 1, 1992, 148(5):1547-1553.
Kozbor, "A human hybrid myeloma for production of human monoclonal antibodies," J. Immunol., Dec. 1984, 133(6):3001-3005.
Krainer, Florian et al., An Updated View on Horseradish Peroxidases: Recombinant Production and Biotechnological Applications, Applied Microbiology and Biotechnology, vol. 99, p. 1611-1625, Jan. 11, 2015.
Kufer, Peter, et al. "A revival of bispecific antibodies." Trends in biotechnology 22.5 (2004): 238-244.
Lee et al., "Bivalent antibody phage display mimics natural immunoglobulin," J. Immunol. Methods, Jan. 2004, 284(1-2):119-132.
Lee et al., "High-affinity human antibodies from phage-displayed synthetic Fab libraries with a single framework scaffold," J. Mol. Biol., Jul. 23, 2004, 340(5):1073-1093.
Lee et al. "Immunogenicity study of Globo H analogues with modification at the reducing or nonreducing end of the tumor antigen" Journal of the American Chemical Society, (2014) 136(48), 16844-16853.
Lehninger, Biochemistry: The Molecular Basis of Cell Structure and Function, 2nd ed., 1975, pp. 73-75, Worth Publishers, New York.
Leung et al., "A method for random mutagenesis of a defined DNA segment using a modified polymerase chain reaction," Technique—A Journal of Methods in Cell and Molecular Biology, Aug. 1989, 1(1):11-15.
Liang, Pi-Hui, et al. "Quantitative Microarray Analysis of Intact Glycolipid-CD1d Interaction and Correlation with Cell-Based Cytokine Production." Journal of the American Chemical Society 130.37 (2008): 12348-12354.
Lindmark et al., "Binding of immunoglobulins to protein A and immunoglobulin levels in mammalian sera," J. Immunol. Meth., Aug. 12, 1983, 62(1):1-13.
Liu et al., "Eradication of large colon tumor xenografts by targeted delivery of maytansinoids," Proc. Natl., Acad. Sci. U.S.A., Aug. 6, 1996, 93(16):8618-8623.
Liu, Gui, et al. "QS-21 structure/function studies: effect of acylation on adjuvant activity." Vaccine 20.21-22 (2002): 2808-2815.
Livingston, Philip, "Augmenting the immunogenicity of carbohydrate tumor antigens" Seminars in Cancer Biology, Cancer Biol, 6(6):357-366, 1995.
Lloyd, Kenneth, "Tumor Antigens Known to be Immunogenic in Man" in Specific Immunotherapy of Cancer with Vaccines, 1993, 690, 50-58.
Lode et al., "Targeted therapy with a novel enediyne antibiotic calicheamicin θI1 effectively suppresses growth and dissemination of liver metastases in a syngeneic model of murine neuroblastoma," Cancer Res., Jul. 15, 1998, 58(14):2925-2928.
Lonberg et al., "Antigen-specific human antibodies from mice comprising four distinct genetic modifications," Nature, Apr. 28, 1994, 368(6474):856-859.
Lonberg et al., "Human antibodies from transgenic mice," Int. Rev. Immunol., 1995, 13(1):65-93.

(56) References Cited

OTHER PUBLICATIONS

Lou, et al., Stage-specific embryonic antigent-4 as a potential therapeutic target in glioblastoma multiforms and other cancers. Proc Natl Acad Sci USA 2014, 111(7):2482-7.

Lucas, A.H. et al., Carbohydrate Moieties as Vaccine Candidates: Meeting Summary, Vaccine, vol. 28(4), Jan. 2010, pp. 1121-1131.

Mandler et al., "Immunoconjugates of geldanamycin and anti-HER2 monoclonal antibodies: antiproliferative activity on human breast carcinoma cell lines," J. Nat. Cancer Inst., Oct. 4, 2000, 92(19):1573-1581.

Mandler et al., "Modifications in synthesis strategy improve the yield and efficacy of geldanamycin-herceptin immunoconjugates," Bioconjugate Chem., Jul.-Aug. 2002, 13(4):786-791.

Mandler et al., "Synthesis and evaluation of antiproliferative activity of a geldanamycin-Herceptin™ immunoconjugate," Bioorganic & Med. Chem. Letters, May 15, 2000, 10(10):1025-1028.

Mao, Shenlan, et al. "Phage-display library selection of high-affinity human single-chain antibodies to tumor-associated carbohydrate antigens sialyl Lewisx and Lewisx." Proceedings of the National Academy of Sciences 96.12 (1999):6953-6958.

Mao, Weiguang, et al. "EphB2 as a therapeutic antibody drug target for the treatment of colorectal cancer." Cancer Research 64.3 (2004): 781-788.

Marasco et al., "Design, intracellular expression, and activity of a human anti-human immunodeficiency virus type 1 gp120 single-chain antibody," Proc. Natl. Acad. Sci. U.S.A., Aug. 15, 1993, 90(16):7889-7893.

Marasco, "Intrabodies: turning the humoral immune system outside in for intracellular immunization," Gene Therapy, Jan. 1997, 4(1):11-15.

Marks et al., "By-passing immunization. Human antibodies from V-gene libraries displayed on phage," J. Mol. Biol., Dec. 5, 1991, 222(3):581-597.

Marks et al., "By-passing immunization: Building high affinity human antibodies by chain shuffling," Nature Biotechnology, Jul. 1992, 10(7):779-783.

Martineau, R.S. et al., Immunochemical Studies on a Panosyl-Azoprotein conjugate, Immunochemistry, vol. 8, 705-718, 1971.

Mather et al., "Culture of testicular cells in hormone-supplemented serum-free medium," Annals N.Y. Acad. Sci., 1982, 383:44-68.

Mather, "Establishment and characterization of two distinct mouse testicular epithelial cell lines," Biol. Reprod., Aug. 1980, 23(1):243-252.

Matsuda, F. et al., "Structure and physical map of 64 variable segments in the 3' 0.8-megabase region of the human immunoglobulin heavy-chain locus." Nature Genet., 1993, 3: 88-94.

McCafferty et al., "Phage antibodies: Filamentous phage displaying antibody variable domains," Nature, Dec. 6, 1990, 348:552-554.

Menard S et al., Generation of Monoclonal Antibodies Reacting with Normal and Cancer Cells of Human Breast, Cancer Res 43: 1295-1300, 1983.

Miller, Kathy, et al. "Design, construction, and in vitro analyses of multivalent antibodies." The Journal of Immunology 170.9 (2003): 4854-4861.

Milstein, C & Cuello, AC, Hybrid Hydridomas and their use in immunohistochemistry, Nature 305, 537-540, Oct. 1993.

Morimoto et al., "Single-step purification of F(ab')2 fragments of mouse monoclonal antibodies (immunoglobulins G1) by hydrophobic interaction high performance liquid chromatography using TSKgel Phenyl-5PW," J. Biochem. Biophys. Meth., Mar. 1992, 24(1-2):107-117.

Morrison et al., "Chimeric human antibody molecules: mouse antigen-binding domains with human constant region domains," Proc. Natl. Acad. Sci. U.S.A., Nov. 1984, 81(21):6851-6855.

Morrison, "Immunology. Success in specification," Nature, Apr. 28, 1994, 368(6474):812-813.

Munson et al., "LIGAND: a versatile computerized approach for characterization of ligand-binding systems," Anal. Biochem., Sep. 1, 1980, 107(1):220-239.

Neuberger et al., "Recombinant antibodies possessing novel effector functions," Nature, Dec. 13-19, 1984, 312(5995):604-608.

Neuberger, "Generating high-avidity human Mabs in mice," Nature Biotechnol., Jul. 1996, 14(7):826.

Nicolaou, K.C. et al., "Calicheamicin ΘI1: A rationally designed molecule with extremely potent and selective DNA cleaving properties and apoptosis inducing activity." Angew. Chem. Intl. Ed. Engl., Feb. 1, 1994, 33(2):183-186.

Niculescu-Duvaz et al., "Antibody-directed enzyme prodrug therapy (ADEPT): A review," Adv. Drg. Del. Rev., Jul. 7, 1997, 26(2-3):151-172.

Nikula, Kristen et al., Animal Models of Chronic Bronchitis and Their Relevance to Studies of Particle-Induced Disease, Inhal. Toxicol. 4(12): 123-153, 2000.

Office Action issued in corresponding Taiwan patent application No. 103131876, dated Dec. 26, 2016, 7 pages.

Orlandi et al., "Cloning immunoglobulin variable domains for expression by the polymerase chain reaction," Proc. Natl. Acad. Sci. U.S.A., May 1989, 86(10):3833-3837.

Ørum et al., "Efficient method for constructing comprehensive murine Fab antibody libraries displayed on phage." Nucleic Acids Res., Sep. 25, 1993, 21(19):4491-4498.

Oxenius, Annette, et al. "CpG-containing oligonucleotides are efficient adjuvants for induction of protective antiviral immune responses with T-cell peptide vaccines." Journal of Virology 73.5 (1999): 4120-4126.

Papanastassiou et al., "The potential for efficacy of the modified (ICP 34.5-) herpes simplex virus HSV1716 following intratumoural injection into human malignant glioma: a proof of principle study," Gene Therapy, Mar. 2002, 9(6):398-406.

Paul, William E. "Structure and Function of Immunoglobulins, Fundamental Immunology." Chapter 9 (1993), 3rd Edition: 292-295.

Pearson, William, Using the FASTA Program to Search Protein and DNA Sequence Databases, Methods Mol. Biol. 243:307-331, 1994.

Pegram, Mark et al., Inhibitory Effects of Combinations of HER-2/neu Antibody and Chemotherapeutic Agents Used for Treatment of Human Breast Cancers, Oncogene 18:2241-2251, 1999.

Pegram, Mark et al., Rational Combinations of Trastuzumab With Chemotherapeutic Drugs Used in the Treatment of Breast Cancer, J. of the Nat. Cancer Inst. 96(10):739-749, 2004.

Plückthun, "Mono- and bivalent antibody fragments produced in *Escherichia coli*: Engineering, folding and antigen binding," Immunol. Rev., Dec. 1992, 130:151-188.

Plückthun, Handbook of Experimental Pharmacology, vol. 113: The Pharmacology of Monoclonal Antibodies, Chapter 11: Antibodies from *Escherichia coli*, Rosenberg et al., eds., 1994, pp. 269-315, Springer-Verlag, Berlin.

Presta et al., "Humanization of an antibody directed against IgE," J. Immunol., Sep. 1, 1993, 151(5):2623-2632.

Presta et al., "Humanization of an anti-vascular endothelial growth factor monoclonal antibody for the therapy of solid tumors and other disorders," Cancer Res., Oct. 15, 1997, 57(20):4593-4599.

Presta, Leonard G. "Antibody engineering." Current Opinion in Biotechnology 3.4 (1992): 394-398.

Presta, "Antibody engineering," Curr. Opin. Str. Biol., Aug. 1992, 2(4):593-596.

Proba et al., "Functional antibody single-chain fragments from the cytoplasm of *Escherichia coli*: influence of thioredoxin reductase (TrxB)," Gene, Jul. 4, 1995, 159(2):203-207.

Queen, Cary et al., A Humanized Antibody that Binds to the Interleukin 2 Receptor, Proc Natl Acad Sci., 86: 10029-10033 (1989).

Ragupathi, Govindaswami et al., Immunization of Mice with a Fully Synthetic Globo H Antigen Results in Antibodies against Human Cancer Cells: A Combined Chemical—Immunological Approach to the Fashioning of an Anticancer Vaccine, Angew Chem Int, 36(1-2), 125-128, Feb. 1997.

Ragupathi, Govindaswami, et al. "Constructing an adenocarcinoma vaccine: Immunization of mice with synthetic KH-1 nonasaccharide stimulates anti-KH-1 and anti-Ley antibodies." International Journal of Cancer 99.2 (2002): 207-212.

(56) References Cited

OTHER PUBLICATIONS

Ramm et al., "The periplasmic *Escherichia coli* peptidylprolyl cis,trans-isomerase FkpA. II. Isomerase-independent chaperone activity in vitro," J. Biol. Chem., Jun. 2, 2000, 275(22):17106-17113.
Ravetch et al., "Fc receptors," Annu. Rev. Immunol., 1991, 9:457-492.
Reyes et al., "Expression of human β-interferon cDNA under the control of a thymidine kinase promoter from herpes simplex virus," Nature, Jun. 17, 1982, 297(5867):598-601.
Rtechmann et al., "Reshaping human antibodies for therapy," Nature, Mar. 24, 1988, 332(6162):323-327.
Rowland et al, "Drug localisation and growth inhibition studies of vindesine-monoclonal anti-CEA conjugates in a human tumour xenograft," Cancer Immunol. Immunother., 1986, 21(3):183-187.
Rüde, Erwin et al., Synthesis of the N-carboxy-α-amino Acid Anhydrides of Several O-acetylated Serine Glycosides, Carbohydr. Research, 1968, 8(2), 219-232.
Rudikoff, Stuart, et al. "Single amino acid substitution altering antigen-binding specificity." Proceedings of the National Academy of Sciences 79.6 (1982):1979-1983.
Sastry et al., "Cloning of the immunological repertoire in *Escherichia coli* for generation of monoclonal catalytic antibodies: construction of a heavy chain variable region-specific cDNA library," Proc. Natl. Acad. Sci. U.S.A., Aug. 1989, 86(15):5728-5732.
Schier et al., "Identification of functional and structural amino-acid residues by parsimonious mutagenesis," Gene, Mar. 9, 1996, 169(2):147-155.
Schiffman, Mark, and Philip E. Castle. "The promise of global cervical-cancer prevention." New England Journal of Medicine 353.20 (2005): 2101-2104.
Schwarz, Mikael, et al. "A new kind of carbohydrate array, its use for profiling antiglycan antibodies, and the discovery of a novel human cellulose-binding antibody." Glycobiology 13.11 (2003): 749-754.
Search Report issued in corresponding Taiwan patent application No. 103131876, prepared Dec. 20, 2016, 1 page.
Sedlik, Christine et al., Effective Antitumor Therapy Based on a Novel Antibody-Drug Conjugate Targeting the Tn Carbohydrate Antigen, Oncoimmunology, Jul. 2016, vol. 5, No. 7, e1171434-1-13.
Shalaby et al., "Development of humanized bispecific antibodies reactive with cytotoxic lymphocytes and tumor cells overexpressing the HER2 protooncogene," J. Exp. Med., Jan. 1, 1992, 175(1):217-225.
Sidhu et al., "Phage-displayed antibody libraries of synthetic heavy chain complementarity determining regions," J. Mol. Biol., Apr. 23, 2004, 338(2):299-310.
Siebenlist et al., "*E. coli* RNA polymerase interacts homologously with two different promoters," Cell, Jun. 1980, 20(2):269-281.
Sigma-Aldrich, Product Information for Hemocyanin From Megathura Crenulata, Catalog No. H7017, 1 Page, 2016.
Simmons et al., "Expression of full-length immunoglobulins in *Escherichia coli*: Rapid and efficient production of aglycosylated antibodies," J. Immunol. Methods, May 1, 2002, 263(1-2):133-147.
Sims et al., "A humanized CD18 antibody can block function without cell destruction," J. Immunol., Aug. 15, 1993, 151(4):2296-2308.
Sjölander, A., et al. "ISCOMs: an adjuvant with multiple functions." J. Leukocyte Biol. 64.6 (1998): 713-723.
Skerra, "Bacterial expression of immunoglobulin fragments," Curr. Opinion in Immunol., Apr. 1993, 5(2):256-262.
Slovin, S.F. et al., Carbohydrate Vaccines in Cancer: Immunogenicity of a Fully Synthetic Globo H Hexasaccharide Conjugate in Man, Proc Natl Acad Sci, 96:5710-5715, May 1999.
Sonderstrup, Grete, Development of Humanized Mice as a Model of Inflammatory Arthritis, Springer Sem. Immunopathol. 25: 35-45, 2003.

Speed, Margaret A., Daniel IC Wang, and Jonathan King. "Multimeric intermediates in the pathway to the aggregated inclusion body state for P22 tailspike polypeptide chains." Protein Science 4.5 (1995): 900-908.
Sun, Hongfan, Kevin GJ Pollock, and James M. Brewer. "Analysis of the role of vaccine adjuvants in modulating dendritic cell activation and antigen presentation in vitro." Vaccine 21.9-10 (2003): 849-855.
Suresh et al., "Bispecific monoclonal antibodies from hybrid hybridomas," Methods in Enzymology, 1986, 121:210-228.
Syrigos et al., "Antibody directed enzyme prodrug therapy (ADEPT): a review of the experimental and clinical considerations," Anticancer Research, Jan.-Feb. 1999, 19(1A):605-614.
Takeda et al., "Construction of chimaeric processed immunoglobulin genes containing mouse variable and human constant region sequences," Nature, Apr. 4-10, 1985, 314(6010):452-454.
Thorpe, (1985) "Antibody Carriers of Cytotoxic Agents In Cancer Therapy: A Review," in Monoclonal Antibodies '84: Biological and Clinical Applications, A. Pinchera et al. (Ed.s), pp. 475-506.
Tomlinson, I.M. et al., "The repertoire of human germline VH sequences reveals about fifty groups of VH segments with different hypervariable loops" J. Mol. Biol., Oct. 5, 1992, 227(3): 776-798.
Toyokuni, Tatsushi et al., Synthetic Vaccines: Synthesis of a Dimeric Tn Antigen-Lipopeptide Conjugate That Elicits Immune Responses Against Tn-Expressing Glycoproteins, J. Am. Chem. Soc., 1994, 116(1), 395-396.
Traunecker et al., "Bispecific single chain molecules (Janusins) target cytotoxic lymphocytes on HIV infected cells," EMBO J., Dec. 1991, 10(12):3655-3659.
Tutt et al., "Trispecific F(ab')3 derivatives that use cooperative signaling via the TCR/CD3 complex and CD2 to activate and redirect resting cytotoxic T cells," J. Immunol., Jul. 1, 1991, 147(1):60-69.
Urlaub et al., "Isolation of Chinese hamster cell mutants deficient in dihydrofolate reductase activity." Proc. Natl. Acad. Sci. U.S.A., Jul. 1980, 77(7):4216-4220.
Vajdos, Felix F., et al. "Comprehensive functional maps of the antigen-binding site of an anti-ErbB2 antibody obtained with shotgun scanning mutagenesis." Journal of Molecular Biology 320.2 (2002): 415-428.
Vaswani et al., "Humanized antibodies as potential therapeutic drugs," Ann. Allergy, Asthma Immunol., Aug. 1998, 81(2):105-116, 119.
Verhoeyen et al., "Reshaping human antibodies: grafting an antilysozyme activity," Science, Mar. 25, 1988, 239(4847):1534-1536.
Wakimoto, Hiroaki, et al. "Intensified antitumor immunity by a cancer vaccine that produces granulocyte-macrophage colony-stimulating factor plus interleukin 4." Cancer Research 56.8 (1996): 1828-1833.
Wallner, Fredrik K., et al. "Solid-phase synthesis of serine-based glycosphingolipid analogues for preparation of glycoconjugate arrays." Organic & Biomolecular Chemistry 3.2 (2005): 309-315.
Wang et al., "Glycan microarray of Globo H and related structures for quantitative analysis of breast cancer," Proc. Natl. Acad. Sci. U.S.A., Aug. 19, 2008, 105(33):11661-11666.
Ward et al., "Binding activities of a repertoire of single immunoglobulin variable domains secreted from *Escherichia coli*," Nature, Oct. 12, 1989, 341(6242):544-546.
Waterhouse et al., "Combinatorial infection and in vivo recombination: a strategy for making large phage antibody repertoires," Nuc. Acids Res., May 11, 1993, 21(9):2265-2266.
Wilen et al., "Strategies in optical resolutions," Tetrahedron, 1977, 33(21):2725-2736.
Williams, S.C. and Winter, G. "Cloning and sequencing of human immunoglobulin Vλ gene segments " Eur. J. Immunol., 1993, 23: 1456-1461.
Wilman, "Prodrugs in Cancer Chemotherapy" Biochemical Society Transactions, 14, pp. 375-382, 615th Meeting Belfast, 1986.
Winter et al., "Making antibodies by phage display technology," Annu. Rev. Immunol., 1994, 12:433-455.
Wymer, Nathan et al., Enzyme-Catalyzed Synthesis of Carbohydrates, Curr. Opin. Chem. Biol., 4, 110-119, 2000.

(56) References Cited

OTHER PUBLICATIONS

Yaniv, Moshe, Enhancing Elements for Activation of Eukaryotic Promoters, Nature 297: 17-18, 1982.

Yansura et al., "Nucleotide sequence selection for increased expression of heterologous genes in *Escherichia coli*," Methods: A Companion to Methods in Enzymol., Aug. 1992, 4(2):151-158.

Yelton et al., "Affinity maturation of the BR96 anti-carcinoma antibody by codon-based mutagenesis." J. Immunol., Aug. 15, 1995, 155(4):1994-2004.

Zhang et al., "Selection of tumor antigens as targets for immune attack using immunohistochemistry: I. Focus on gangliosides," Int. J. Cancer, Sep. 26, 1997,73(1):42-49.

Zhou, Zhifang et al., A Fully Synthetic Self-Adjuvanting Globo H-Based Vaccine Elicited Strong T Cell-Mediated Antitumor Immunity, Chem. Sci., 2015, 6, 7112-7121.

Zhu, Jianglong et al., From Synthesis to Biologies: Preclinical Data on a Chemistry Derived Anticancer Vaccine, J. Am. Chem. Soc. 131(26):9298-9303, 2009.

\* cited by examiner

FIG. 4

| Antibody | GlcNAc | 1N-G2S2 | 2N-G2S2 | ADCC Original (EC 50) | ADCC homogeneous (EC 50) | ADCC increase Fold |
|---|---|---|---|---|---|---|
| OBI-888 | 6.33% | 6.10% | 87.57% | 11.92 (μg/ml) | 0.45 (μg/ml) | 26.49 |
| Herceptin | 0.44% | 8.45% | 91.11% | 15.29 (μg/ml) | 5.10 (μg/ml) | 3.00 |
| Perjeta | 0.00% | 7.51% | 92.49% | 23.19 (μg/ml) | 3.75 (μg/ml) | 6.18 |
| Erbitux | 2.71% | 9.38% | 87.92% | 8.84 (ng/ml) | 0.86 (ng/ml) | 10.28 |
| Rituxan | 0.00% | 2.43% | 97.57% | 42.4 (ng/ml) | 3.6 (ng/ml) | 11.78 |
| OBI-898 | 0.87% | 9.40% | 89.73% | - | - | |
| Vectibix | 1.56% | 13.21% | 86.12% | - | - | |
| Humira | 0.92% | 5.40% | 93.68% | - | - | |
| Keytruda | 7.65% | 16.54% | 75.81% | - | - | |
| Bavencio | 2.35% | 6.95% | 90.73% | - | - | |

SEQUENCE LISTING

```
<160> NUMBER OF SEQ ID NOS: 8

<210> SEQ ID NO 1
<211> LENGTH: 1054
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly Thr Ile Leu Gly Thr His His Asp Ser Leu Ile Ser Val Lys
1               5                   10                  15

Ala Glu Glu Lys Ile Thr Gln Val Ser Gln Thr Ser Thr Ser Ile Asp
                20                  25                  30

Asp Leu His Tyr Leu Ser Glu Asn Ser Lys Lys Glu Phe Lys Glu Glu
            35                  40                  45

Leu Ser Lys Glu Lys Val Pro Glu Lys Val Lys Glu Ile Leu Ser Lys
        50                  55                  60

Ala Gln Gln Ala Asn Lys Gln Ala Gln Glu Leu Ala Glu Met Lys Val
65                  70                  75                  80

Pro Asp Lys Ile Pro Met Lys Pro Leu Asn Gly Pro Leu Tyr Gly Gly
                85                  90                  95

Tyr Phe Arg Thr Trp His Asp Lys Thr Ser Asp Pro Leu Glu Lys Asp
```

-continued

```
            100                 105                 110
Lys Val Asn Ser Met Gly Glu Leu Pro Lys Glu Val Asp Leu Ala Phe
            115                 120                 125

Val Phe His Asp Trp Thr Lys Asp Tyr Ser Leu Phe Trp Lys Glu Leu
            130                 135             140

Ala Thr Lys His Val Pro Lys Leu Asn Lys Gln Gly Thr Arg Val Ile
145                     150                 155                 160

Arg Thr Ile Pro Trp Arg Phe Leu Ala Gly Gly Asp Asn Ser Gly Ile
                165                 170                 175

Ala Glu Asp Ala Ser Lys Tyr Pro Asn Thr Pro Glu Gly Asn Lys Ala
            180                 185                 190

Leu Ala Lys Ala Ile Val Asp Glu Tyr Val Tyr Lys Tyr Asn Leu Asp
            195                 200                 205

Gly Leu Asp Val Met Ile Glu His Asp Ser Ile Pro Lys Val Asn Gly
            210                 215                 220

Glu Ala Ser Asp Glu Asn Leu Lys Arg Ser Ile Asp Val Phe Glu Glu
225                 230                 235                 240

Ile Gly Lys Leu Ile Gly Pro Lys Gly Ala Asp Lys Ser Arg Leu Phe
                245                 250                 255

Ile Met Asp Ser Thr Tyr Met Ala Asp Lys Asn Pro Leu Ile Glu Arg
                260                 265                 270

Gly Ala Pro Tyr Ile Asp Leu Leu Leu Val Gln Val Tyr Gly Ser Gln
                275                 280                 285

Gly Glu Gln Gly Glu Phe Gln Asn Asp Thr Lys Ser Val Thr Lys Thr
            290                 295                 300

Pro Glu Glu Arg Trp Gln Gly Tyr Ser Lys Tyr Ile Arg Pro Glu Gln
305                 310                 315                 320

Tyr Met Ile Gly Phe Ser Phe Tyr Glu Glu Lys Ala Gly Ser Gly Asn
                325                 330                 335

Leu Trp Tyr Asp Ile Asn Ala Arg Lys Asp Glu Asp Thr Ala Asn Gly
                340                 345                 350

Ile Asn Asp Asp Ile Thr Gly Thr Arg Ala Glu Arg Tyr Ala Arg Trp
            355                 360                 365

Gln Pro Lys Thr Gly Gly Val Lys Gly Gly Ile Phe Ser Tyr Ala Ile
            370                 375                 380

Asp Arg Asp Gly Val Ala His Gln Pro Lys Gln Ile Ala Glu Lys Asp
385                 390                 395                 400

Lys Gln Ser Val Lys Asn Asn Arg Pro Leu Ile Ser Glu Ile Thr Asp
                405                 410                 415

Asn Ile Phe His Ser Asn Tyr Ser Val Ser Lys Thr Leu Lys Thr Val
            420                 425                 430

Met Leu Lys Asp Lys Ala Tyr Asp Leu Ile Asp Glu Lys Asp Phe Pro
            435                 440                 445

Asp Lys Ala Leu Arg Glu Ala Val Met Ala Gln Val Gly Thr Arg Lys
            450                 455                 460

Gly Asp Leu Glu Arg Phe Asn Gly Thr Leu Arg Leu Asp Asn Pro Ala
465                 470                 475                 480

Ile Gln Ser Leu Glu Gly Leu Asn Lys Phe Lys Lys Leu Ala Gln Leu
            485                 490                 495

Asp Leu Ile Gly Leu Ser Arg Ile Ile Lys Leu Asp Gln Ser Val Leu
                500                 505                 510

Pro Ala Asn Met Lys Pro Gly Lys Asp Pro Leu Glu Thr Val Leu Glu
            515                 520                 525
```

```
Thr Tyr Lys Lys Asn Gly Lys Glu Glu Pro Ala Ile Ile Pro Pro Val
    530                 535                 540

Ser Leu Thr Val Ser Gly Leu Thr Gly Leu Lys Glu Leu Asp Leu Ser
545                 550                 555                 560

Gly Phe Asp Arg Glu Thr Leu Ala Gly Ile Asp Ala Ala Thr Leu Thr
                565                 570                 575

Ser Leu Glu Lys Val Asp Ile Ser Asp Asn Lys Leu Asp Leu Ala Pro
            580                 585                 590

Lys Thr Glu Asn Arg Gln Ile Phe Asp Val Met Leu Ser Thr Val Asn
        595                 600                 605

Asn Asn Ala Gly Ile Ser Glu Gln Ser Ile Lys Phe Asp Asn Gln Lys
    610                 615                 620

Pro Ala Gly Asn Tyr Pro Gln Thr Tyr Gly Ala Thr Asn Leu Gln Leu
625                 630                 635                 640

Pro Val Arg Gln Glu Lys Ile Asp Leu Gln His Gln Leu Leu Phe Gly
                645                 650                 655

Thr Ile Thr Asn Gln Gly Thr Leu Ile Asn Ser Glu Ala Asp Tyr Lys
            660                 665                 670

Thr Tyr Arg Asn Gln Lys Ile Ala Gly Arg Asn Phe Val Asp Pro Asp
        675                 680                 685

Tyr Pro Tyr Asn Asn Phe Lys Val Ser His Asp Asn Tyr Thr Val Lys
    690                 695                 700

Val Thr Asp Ser Thr Leu Gly Thr Thr Thr Asp Lys Met Leu Ala Thr
705                 710                 715                 720

Asp Lys Glu Glu Thr Tyr Lys Val Asp Phe Phe Ser Pro Thr Asp Lys
                725                 730                 735

Thr Lys Ala Val His Thr Ala Lys Val Ile Val Gly Asp Glu Lys Thr
            740                 745                 750

Met Met Val Asn Leu Ala Glu Gly Ala Thr Val Ile Lys Ser Glu Asn
        755                 760                 765

Asp Glu Asn Ala Gln Lys Val Phe Asn Gly Ile Met Glu Tyr Asn Pro
    770                 775                 780

Leu Ser Phe Asn Asn Lys Ser Ile Ile Phe Glu Ile Lys Asp Pro
785                 790                 795                 800

Ser Leu Ala Lys Tyr Trp Arg Leu Phe Asn Asp Ser Ser Lys Asp Lys
                805                 810                 815

Lys Asp Tyr Ile Lys Glu Ala Lys Leu Glu Val Phe Thr Gly Gln Leu
            820                 825                 830

Asn Ala Glu Ala Asp Val Lys Thr Ile Leu Glu Lys Pro Asp Asn Trp
        835                 840                 845

Val Thr Val Ser Thr Tyr Ser Gly Glu Glu Lys Val Phe Ser His Ser
    850                 855                 860

Leu Asp Asn Ile Ser Ala Lys Tyr Trp Arg Val Thr Val Asp Asn Lys
865                 870                 875                 880

Lys Asp Gln Tyr Gly Tyr Val Ser Leu Pro Glu Leu Gln Ile Leu Gly
                885                 890                 895

Tyr Pro Leu Pro Asn Ala Asp Thr Ile Met Lys Thr Val Thr Val Ala
            900                 905                 910

Lys Glu Leu Ser Gln Gln Lys Asp Lys Phe Pro Gln Gln Leu Leu Asp
        915                 920                 925

Glu Ser Thr Ala Lys Glu Ala Val Val Glu Ala Ser Leu Asn Ser Lys
    930                 935                 940
```

```
Leu Phe Asp Thr Gly Val Ile Asn Thr Asn Val Glu Ala Leu Lys Asn
945                 950                 955                 960

Val Val Asp Glu Cys Leu Ala Tyr Glu Lys Asn Lys Glu Thr Ala Phe
                965                 970                 975

Lys Ala Thr Glu Asp Tyr Arg Ala Ala Val Asn Gly Val Lys Ala Glu
                980                 985                 990

Ser Val Thr Val Glu Glu Met Ala  Gln Leu Lys Asp Leu Ile Gly Lys
        995                 1000                1005

Ala Ala  His Leu Asn Ser Lys  Ile Asp Ala Lys Leu  Ala Asp Arg
    1010                1015                1020

Glu Tyr  Asp Lys Asp Leu Leu  Gly Leu Ile Gly Glu  Leu Thr Asn
    1025                1030                1035

Ile Thr  Arg Thr Val Lys Ser  Phe Val Lys His His  His His His
    1040                1045                1050

His
```

<210> SEQ ID NO 2
<211> LENGTH: 998
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Val Ala Ile Leu Ala Ala Gln His Asp Ser Leu Ile Arg Val Lys
1               5                   10                  15

Ala Glu Asp Lys Leu Val Gln Thr Ser Pro Ser Val Ser Ala Ile Asp
                20                  25                  30

Ala Leu His Tyr Leu Ser Glu Asn Ser Lys Lys Glu Phe Lys Glu Glu
            35                  40                  45

Leu Ser Lys Val Glu Lys Ala Gln Pro Glu Lys Leu Lys Glu Ile Val
50                  55                  60

Ser Lys Ala Gln Gln Ala Asp Lys Gln Ala Lys Thr Leu Ala Glu Met
65                  70                  75                  80

Lys Val Pro Glu Lys Ile Pro Met Lys Pro Leu Lys Gly Pro Leu Tyr
                85                  90                  95

Gly Gly Tyr Phe Arg Thr Trp His Asp Lys Thr Ser Asp Pro Ala Glu
                100                 105                 110

Lys Asp Lys Val Asn Ser Met Gly Glu Leu Pro Lys Glu Val Asp Leu
            115                 120                 125

Ala Phe Val Phe His Asp Trp Thr Lys Asp Tyr Ser Leu Phe Trp Gln
130                 135                 140

Glu Leu Ala Thr Lys His Val Pro Thr Leu Asn Lys Gln Gly Thr Arg
145                 150                 155                 160

Val Ile Arg Thr Ile Pro Trp Arg Phe Leu Ala Gly Gly Asp His Ser
                165                 170                 175

Gly Ile Ala Glu Asp Ala Gln Lys Tyr Pro Asn Thr Pro Glu Gly Asn
                180                 185                 190

Lys Ala Leu Ala Lys Ala Ile Val Asp Glu Tyr Val Tyr Lys Tyr Asn
            195                 200                 205

Leu Asp Gly Leu Asp Val Met Ile Glu Arg Asp Ser Ile Pro Lys Val
        210                 215                 220

Asn Lys Glu Glu Ser Lys Glu Gly Ile Glu Arg Ser Ile Gln Val Phe
225                 230                 235                 240
```

```
Glu Glu Ile Gly Lys Leu Ile Gly Pro Lys Gly Asp Lys Ser Arg
            245                 250                 255
Leu Phe Ile Met Asp Ser Thr Tyr Met Ala Asp Lys Asn Pro Leu Ile
            260                 265                 270
Glu Arg Gly Ala Pro Tyr Ile Asp Leu Leu Val Gln Val Tyr Gly
            275                 280             285
Thr Gln Gly Glu Lys Gly Gly Phe Asp Asn Ala Asn His Lys Ala Val
290                 295                 300
Asp Thr Met Glu Glu Arg Trp Glu Ser Tyr Lys Tyr Ile Arg Pro
305                 310                 315                 320
Glu Gln Tyr Met Val Gly Phe Ser Phe Tyr Glu Glu Lys Ala Asn Ser
                325                 330                 335
Gly Asn Leu Trp Tyr Asp Val Asn Val Glu Asp Thr Asn Pro Asn
            340                 345                 350
Ile Gly Ser Glu Ile Lys Gly Thr Arg Ala Glu Arg Tyr Ala Lys Trp
            355                 360                 365
Gln Pro Lys Thr Gly Gly Val Lys Gly Ile Phe Ser Tyr Gly Ile
            370                 375             380
Asp Arg Asp Gly Val Ala His Pro Lys Lys Asn Gly Pro Lys Thr Pro
385                 390                 395                 400
Asp Leu Asp Lys Ile Val Lys Ser Asp Tyr Lys Val Ser Lys Ala Leu
                405                 410                 415
Lys Lys Val Met Glu Asn Asp Lys Ser Tyr Glu Leu Ile Asp Gln Lys
                420                 425                 430
Asp Phe Pro Asp Lys Ala Leu Arg Glu Ala Val Ile Ala Gln Val Gly
            435                 440                 445
Ser Arg Arg Gly Asn Leu Glu Arg Phe Asn Gly Thr Leu Arg Leu Asp
450                 455                 460
Asn Pro Asp Ile Lys Ser Leu Glu Gly Leu Asn Lys Leu Lys Leu
465                 470                 475             480
Ala Lys Leu Glu Leu Ile Gly Leu Ser Gln Ile Thr Lys Leu Asp Ser
                485                 490                 495
Ser Val Leu Pro Glu Asn Ile Lys Pro Thr Lys Asp Thr Leu Val Ser
                500                 505                 510
Val Leu Glu Thr Tyr Lys Asn Asp Asp Arg Lys Glu Glu Ala Lys Ala
            515                 520                 525
Ile Pro Gln Val Ala Leu Thr Ile Ser Gly Leu Thr Gly Leu Lys Glu
            530                 535                 540
Leu Asn Leu Ala Gly Phe Asp Arg Asp Ser Leu Ala Gly Ile Asp Ala
545                 550                 555                 560
Ala Ser Leu Thr Ser Leu Glu Lys Val Asp Leu Ser Ser Asn Lys Leu
                565                 570                 575
Asp Leu Ala Ala Gly Thr Glu Asn Arg Gln Ile Leu Asp Thr Met Leu
            580                 585                 590
Ala Thr Val Thr Lys His Gly Gly Val Ser Glu Lys Thr Phe Val Phe
            595                 600                 605
Asp His Gln Lys Pro Thr Gly Leu Tyr Pro Asp Thr Tyr Gly Thr Lys
        610                 615                 620
Ser Leu Gln Leu Pro Val Ala Asn Asp Thr Ile Asp Leu Gln Ala Lys
625                 630                 635                 640
Leu Leu Phe Gly Thr Val Thr Asn Gln Gly Thr Leu Ile Asn Ser Glu
            645                 650                 655
Ala Asp Tyr Lys Ala Tyr Gln Glu Gln Glu Ile Ala Gly His Arg Phe
```

```
                    660               665               670
Val Asp Ser Ser Tyr Asp Tyr Lys Ala Phe Ala Val Thr Tyr Lys Asp
            675               680               685

Tyr Lys Ile Lys Val Thr Asp Ser Thr Leu Gly Val Thr Asp His Lys
        690               695               700

Asp Leu Ser Thr Ser Lys Glu Glu Thr Tyr Lys Val Glu Phe Phe Ser
705               710               715               720

Pro Ile Asn Ser Thr Lys Pro Val His Glu Ala Lys Ile Val Val Gly
                    725               730               735

Glu Glu Lys Thr Met Met Val Asn Leu Ala Glu Gly Ala Thr Ile Ile
                740               745               750

Gly Gly Asp Ala Asp Pro Thr Asn Ala Lys Lys Val Phe Asp Gly Leu
            755               760               765

Leu Asn Asn Asp Thr Thr Thr Leu Ser Thr Ser Asn Lys Ala Ser Ile
        770               775               780

Ile Phe Glu Leu Lys Glu Pro Gly Leu Val Lys His Trp Arg Phe Phe
785               790               795               800

Asn Asp Ser Lys Ile Ser Lys Ala Asp Tyr Ile Lys Glu Ala Lys Leu
                    805               810               815

Glu Ala Phe Val Gly His Leu Glu Asp Ser Ser Lys Val Lys Asp Ser
                820               825               830

Leu Glu Lys Ser Thr Glu Trp Val Thr Val Ser Asp Tyr Ser Gly Glu
            835               840               845

Ala Gln Glu Phe Ser Gln Pro Leu Asn Asn Ile Gly Ala Lys Tyr Trp
        850               855               860

Arg Ile Thr Ile Asp Asn Lys Lys Ser Gln Tyr Gly Tyr Val Ser Leu
865               870               875               880

Pro Glu Leu Gln Ile Ile Gly His Arg Leu Pro Glu Ala Ala Thr Val
                    885               890               895

Met Thr Thr Met Ala Ala Ala Glu Glu Leu Ser Gln Gln Lys Asp Lys
                900               905               910

Phe Ser Gln Glu Gln Leu Lys Glu Leu Glu Val Lys Val Ala Ala Leu
            915               920               925

Lys Ala Ala Leu Asp Asn Lys Met Phe Asn Ala Asp Thr Ile Asn Ala
        930               935               940

Ser Phe Ala Asp Val Lys Ala Tyr Ile Asp Lys Leu Leu Ala Asp Ala
945               950               955               960

Ala Gly Lys Lys Thr Leu Gly Lys Ala Thr Lys Glu Ala Gln Pro Val
                    965               970               975

Ala Thr Asp Ala Lys Glu Lys Ala Glu Ser Glu Asn Pro Lys Ala Asp
                980               985               990

His His His His His His
            995

<210> SEQ ID NO 3
<211> LENGTH: 3147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atgggcacca tcctgggtac ccaccacgac agcctgatca gcgtgaaggc ggaggaaaaa      60 attcccaag ttagccaaac cagcaccagc attgacgatc tgcactacct gagcgaaaac     120
```

```
agcaagaaag agttcaaaga ggagctgagc aaggagaaag tgccggaaaa ggttaaagag      180
atcctgagca aagcgcagca agcgaacaag caggcgcaag agctggcgga aatgaaggtg      240
ccggacaaaa ttccgatgaa gccgctgaac ggtccgctgt atggtggcta ctttcgtacc      300
tggcacgaca aaaccagcga tccgctggaa aaggacaaag ttaacagcat gggcgaactg      360
ccgaaagagg tggatctggc gttcgttttt cacgactgga ccaaagatta tagcctgttc      420
tggaaagagc tggcgaccaa gcacgtgccg aagctgaaca acagggtac ccgtgttatc       480 cgtaccattc cgtggcgttt tctggcgggt ggcgacaaca gcggtattgc ggaagatgcg      540
agcaagtacc cgaacacccc ggagggtaac aaagcgctgg cgaaggcgat tgtggacgaa     600
tacgtttata atacaacct ggacggtctg gatgtgatga tcgagcacga tagcattccg       660
aaagttaacg gcgaagcgag cgacgagaac ctgaagcgta gcatcgatgt gttcgaggaa      720
atcggtaaac tgattggtcc gaaaggcgcg gacaagagcc gtctgtttat tatggacagc      780
acctatatgg cggataagaa cccgctgatc gaacgtggcg cgccgtatat tgacctgctg      840
ctggtgcagg tttacggtag ccagggcgag cagggtgaat ccaaaacga taccaaaagc       900 gttaccaaga ccccggagga acgttggcag ggctatagca aatacatccg tccggagcaa      960
tatatgattg gtttcagctt ttacgaggaa aaggcgggta gcggcaacct gtggtacgac     1020
atcaacgcgc gtaaagacga agataccgcg aacggcatca cgacgatat taccggtacc      1080 cgtgcggagc gttatgcgcg ttggcagccg aaaaccggtg gcgtgaaggg tggcatcttt      1140
agctacgcga ttgaccgtga tggtgttgcg caccagccga agcaaatcgc ggaaaaggac      1200
aaacaaagcg tgaaaaacaa ccgtccgctg atcagcgaga ttaccgataa cattttccac      1260
agcaactata gcgtgagcaa gaccctgaaa accgttatgc tgaaggacaa agcgtacgac      1320
ctgatcgatg aaaaagactt tccggataaa gcgctgcgtg aggcggtgat ggcgcaggtt      1380
ggcacccgta agggtgacct ggaacgtttc aacggcaccc tgcgtctgga taacccggcg      1440
atccagagcc tggagggtct gaacaagttt aagaaactgg cgcaactgga cctgattggc      1500
ctgagccgta tcattaaact ggatcaaagc gtgctgccgg cgaacatgaa gccgggtaaa     1560
gacccgctgg aaaccgttct ggagacctac aagaaaaacg gcaaagagga gccggcgatc      1620
attccgccgg ttagcctgac cgttagcggt ctgaccggtc tgaaagaact ggacctgagc     1680
ggcttcgatc gtgagaccct ggcgggtatc gatgcggcga ccctgaccag cctggaaaag     1740
gtggacatta gcgataacaa actggacctg gcgccgaaga ccgagaaccg tcagatcttc     1800
gatgtgatgc tgagcaccgt taacaacaac gcgggtatca gcgagcagag cattaaattt      1860
gacaaccaaa agccggcggg caactatccg caaacctacg gtgcgaccaa cctgcagctg     1920
ccggttcgtc aagaaaaaat cgacctgcag caccaactgc tgttcggcac catcaccaac      1980
cagggtaccc tgattaacag cgaggcggat tataaaacct accgtaacca aaagattgcg     2040
ggtcgtaact tcgtggaccc ggattatccg tacaacaact ttaaagttag ccacgacaac     2100
tataccgtga aggttaccga tagcaccctg gcaccacca ccgacaaaat gctggcgacc       2160
gataaagagg aaacctacaa ggtggacttc tttagcccga ccgataagac caaagcggtt     2220
cacaccgcga aagtgatcgt tggcgacgaa aagaccatga tggtgaacct ggcggagggt      2280
gcgaccgtta tcaaaagcga gaacgatgaa aacgcgcaga aggttttcaa cggtattatg     2340
gaatataacc cgctgagctt caacaacaag agcagcatca tttttgagat caaagacccg      2400
agcctggcga agtattggcg tctgttcaac gatagcagca agacaagaa agattacatc       2460
```

-continued

```
aaggaagcga aactggaagt gtttaccggt cagctgaacg cggaagcgga cgttaaaacc    2520
attctggaga agccggataa ctgggtgacc gttagcacct atagcggcga ggaaaaggtg    2580
tttagccaca gcctggacaa catcagcgcg aaatactggc gtgtgaccgt tgacaacaag    2640
aaagatcagt atggctacgt tagcctgccg gagctgcaaa tcctgggtta cccgctgccg    2700
aacgcggata ccattatgaa aaccgtgacc gttgcgaagg aactgagcca gcaaaggac     2760 aaattcccgc agcaactgct ggatgagagc accgcgaagg aagcggtggt tgaggcgagc    2820
ctgaacagca aactgtttga caccggtgtg atcaacacca cgttgaagc gctgaagaac     2880 gtggttgatg agtgcctggc gtatgaaaag aacaaagaga ccgcgttcaa ggcgaccgaa    2940
gactaccgtg cggcggtgaa cggtgttaaa gcggagagcg tgaccgttga ggaaatggcg    3000
cagctgaaag atctgatcgg caaggcggcg cacctgaaca gcaaaattga cgcgaagctg    3060
gcggatcgtg aatacgacaa agatctgctg ggcctgatcg gcgagctgac caacattacc    3120
cgtaccgtga aagctttgt taagtga                                         3147
```

<210> SEQ ID NO 4
<211> LENGTH: 2979
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atggttgcga tcctggcggc gcaacacgat agcctgattc gtgtgaaggc ggaggacaaa     60
ctggtgcaga ccagcccgag cgttagcgcg attgatgcgc tgcactacct gagcgaaaac    120
agcaagaaag aattcaaaga ggaactgagc aaggttgaaa aagcgcaacc ggagaagctg    180
aaagaaatcg tgagcaaggc gcagcaagcg acaagcagg cgaaaaccct ggcggagatg     240
aaggttccgg aaaaaattcc gatgaagccg ctgaaaggcc cgctgtatgg tggctacttt    300
cgtacctggc acgataaaac cagcgacccg gcggagaagg ataaagtgaa cagcatgggc    360
gagctgccga agaagtggac cctggcgttc gttttcacg attggaccaa ggactatagc     420
ctgttctggc aagaactggc gaccaaacac gttccgaccc tgaacaagca gggcacccgt    480
gtgatccgta ccattccgtg gcgttttctg gcgggtggcg atcacagcgg tatcgcggag    540
gacgcgcaga ataccccgaa caccccggaa ggcaacaagg cgctggcgaa agcgattgtg    600
gatgagtacg tttataagta caacctggac ggtctggatg ttatgatcga acgtgacagc    660
attccgaagg tgaacaaaga ggaaagcaaa gagggtatcg aacgtagcat tcaggttttc    720
gaggaaatcg gcaagctgat tggtccgaag ggcgcggata aaagccgtct gtttatcatg    780
gatagcacct atatggcgga caagaacccg ctgatcgagc gtggtgcgcc gtatattgac    840
ctgctgctgg tgcaggttta cggtacccag ggcgaaaaag gtggcttcga taacgcgaac    900 cacaaggcg ttgacaccat ggaggaacgt tgggagagct atagcaaata catccgtccg    960
gaacaatata tggtgggttt cagctttac gaggaaaagg cgaacagcgg caacctgtgg    1020
tacgacgtga acgttgagga cgataccaac ccgaacatcg gtagcgagat taaaggcacc    1080
cgtgcggaac gttatgcgaa gtggcagccg aaaaccggtg gcgttaaggg tggcatcttt    1140
agctacggta ttgaccgtga tggcgtggcg caccccgaaga aaaacggtcc gaaaaccccg    1200
gacctggata gatcgtgaa aagcgattat aaagttagca aagcgctgaa gaagttatg     1260 gagaacgaca agagctacga actgatcgac caaaaggatt tcccggacaa agcgctgcgt    1320
```

```
gaggcggtga ttgcgcaggt tggtagccgt cgtggcaacc tggaacgttt taacggtacc  1380
ctgcgtctgg ataaccccgga catcaaaagc ctggagggcc tgaacaaact gaagaaactg  1440
gcgaagctgg aactgatcgg tctgagccaa attaccaagc tggatagcag cgttctgccg  1500
gagaacatta gccgaccaa agacaccctg gtgagcgttc tggaaaccta caaaaacgac  1560
gatcgtaagg aagaggcgaa agcgatcccg caggtggcgc tgaccattag cggtctgacc  1620
ggcctgaagg agctgaacct ggcgggtttc gaccgtgata gcctggcggg tattgatgcg  1680
gcgagcctga ccagcctgga aaagtggat ctgagcagca caagctgga cctggcggcg  1740
ggtaccgaaa accgtcaaat tctggacacc atgctggcga ccgtgaccaa acacggtggc  1800
gttagcgaga agaccttcgt gtttgatcac cagaaaccga ccggtctgta tccggacacc  1860
tacggcacca gagcctgca gctgccggtt gcgaacgata ccatcgacct gcaagcgaaa  1920
ctgctgttcg gtaccgtgac caaccagggc accctgatca cagcgaagc ggactataag  1980
gcgtaccagg agcaagaaat tgcgggccac cgtttcgttg atagcagcta tgactacaaa  2040
gcgtttgcgg tgacctacaa ggattacaag atcaaggtta ccgacagcac cctgggtgtg  2100
accgatcaca aagacctgag caccagcaaa gaggagacct ataaagttga gttctttagc  2160
ccgatcaaca gcaccaaacc ggtgcacgaa gcgaagattg tggttggcga ggaaaagacc  2220
atgatggtta acctggcgga gggcgcgacc atcattggtg cgacgcgga cccgaccaac  2280
gcgaagaaag tgttcgatgg cctgctgaac aacgacacca ccaccctgag caccagcaac  2340
aaagcgagca tcatttttga gctgaaagaa ccgggtctgg tgaagcactg gcgtttcttt  2400
aacgatagca gatcagcaa agcggactac attaaagagg cgaaactgga agcgttcgtt  2460
ggtcacctgg aagatagcag caaggtgaaa gacagcctgg agaaaagcac cgaatgggtg  2520
accgttagcg attatagcgg cgaggcgcag gaatttagcc aaccgctgaa caacatcggc  2580
gcgaagtact ggcgtatcac cattgacaac aagaaaagcc agtatggtta cgttagcctg  2640
ccggagctgc aaatcattgg tcatcgtctg ccggaagcgg cgaccgtgat gaccaccatg  2700
gcggcggcgg aggaactgag ccagcaaaag gataaattca gccaggagca actgaaggag  2760
ctggaagtga agttgcggc gctgaaggcg gcgctggata caaaatgtt caacgcggac  2820
accatcaacg cgagctttgc ggacgttaaa gcgtacattg ataagctgct ggcggacgcg  2880
gcgggtaaga aaaaccctggg caaagcgacc aaagaggcgc agccggtggc gaccgatgcg  2940
aaggaaaaag cggagagcga aaacccgaag gcggactaa                         2979

<210> SEQ ID NO 5
<211> LENGTH: 111
<212> TYPE: PRT
<213> ORGANISM: Unknown
<220> FEATURE:
<223> OTHER INFORMATION: Description of Unknown:
      EndoS2 sequence

<400> SEQUENCE: 5

Thr Ala Leu Val Gln Thr Ile Gly Val Asn Glu Leu Asn Gly Arg Thr
1               5                   10                  15

Gly Leu Ser Lys Asp Tyr Pro Asp Thr Pro Glu Gly Asn Lys Ala Leu
            20                  25                  30

Ala Ala Ala Ile Val Lys Ala Phe Val Thr Asp Arg Gly Val Asp Gly
        35                  40                  45

Leu Asp Ile Asp Ile Glu His Glu Phe Thr Asn Lys Arg Thr Pro Glu
    50                  55                  60
```

```
Glu Asp Ala Arg Ala Leu Asn Val Phe Lys Glu Ile Ala Gln Leu Ile
 65                  70                  75                  80

Gly Lys Asn Gly Ser Asp Lys Ser Lys Leu Leu Ile Met Asp Thr Thr
                 85                  90                  95

Leu Ser Val Glu Asn Asn Pro Ile Phe Lys Gly Ile Ala Glu Asp
            100                 105                 110
```

<210> SEQ ID NO 6
<211> LENGTH: 120
<212> TYPE: PRT
<213> ORGANISM: Unknown
<220> FEATURE:
<223> OTHER INFORMATION: Description of Unknown:
      EndoS sequence

<400> SEQUENCE: 6

```
Thr Arg Val Ile Arg Thr Ile Pro Trp Arg Phe Leu Ala Gly Gly Asp
  1               5                  10                  15

Asn Ser Gly Ile Ala Glu Asp Thr Ser Lys Tyr Pro Asn Thr Pro Glu
                 20                  25                  30

Gly Asn Lys Ala Leu Ala Lys Ala Ile Val Asp Glu Tyr Val Tyr Lys
             35                  40                  45

Tyr Asn Leu Asp Gly Leu Asp Val Asp Val Glu His Asp Ser Ile Pro
 50                  55                  60

Lys Val Asp Lys Lys Glu Asp Thr Ala Gly Val Glu Arg Ser Ile Gln
 65                  70                  75                  80

Val Phe Glu Glu Ile Gly Lys Leu Ile Gly Pro Lys Gly Val Asp Lys
                 85                  90                  95

Ser Arg Leu Phe Ile Met Asp Ser Thr Tyr Met Ala Asp Lys Asn Pro
            100                 105                 110

Leu Ile Glu Arg Gly Ala Pro Tyr
            115                 120
```

<210> SEQ ID NO 7
<211> LENGTH: 120
<212> TYPE: PRT
<213> ORGANISM: Unknown
<220> FEATURE:
<223> OTHER INFORMATION: Description of Unknown:
      EndoSz sequence

<400> SEQUENCE: 7

```
Thr Arg Val Ile Arg Thr Ile Pro Trp Arg Phe Leu Ala Gly Gly Asp
  1               5                  10                  15

His Ser Gly Ile Ala Glu Asp Ala Gln Lys Tyr Pro Asn Thr Pro Glu
                 20                  25                  30

Gly Asn Lys Ala Leu Ala Lys Ala Ile Val Asp Glu Tyr Val Tyr Lys
             35                  40                  45

Tyr Asn Leu Asp Gly Leu Asp Val Asp Ile Glu Arg Asp Ser Ile Pro
 50                  55                  60

Lys Val Asn Lys Glu Glu Ser Lys Gly Ile Glu Arg Ser Ile Gln
 65                  70                  75                  80

Val Phe Glu Glu Ile Gly Lys Leu Ile Gly Pro Lys Gly Ala Asp Lys
                 85                  90                  95

Ser Arg Leu Phe Ile Met Asp Ser Thr Tyr Met Ala Asp Lys Asn Pro
            100                 105                 110

Leu Ile Glu Arg Gly Ala Pro Tyr
            115                 120
```

```
<210> SEQ ID NO 8
<211> LENGTH: 120
<212> TYPE: PRT
<213> ORGANISM: Unknown
<220> FEATURE:
<223> OTHER INFORMATION: Description of Unknown:
      EndoSd sequence

<400> SEQUENCE: 8

Thr Arg Val Ile Arg Thr Ile Pro Trp Arg Phe Leu Ala Gly Gly Asp
1               5                   10                  15

Asn Ser Gly Ile Ala Glu Asp Ala Ser Lys Tyr Pro Asn Thr Pro Glu
            20                  25                  30

Gly Asn Lys Ala Leu Ala Lys Ala Ile Val Asp Glu Tyr Val Tyr Lys
        35                  40                  45

Tyr Asn Leu Asp Gly Leu Asp Val Asp Ile Glu His Asp Ser Ile Pro
    50                  55                  60

Lys Val Asn Gly Glu Ala Ser Asp Glu Asn Leu Lys Arg Ser Ile Asp
65                  70                  75                  80

Val Phe Glu Glu Ile Gly Lys Leu Ile Gly Pro Lys Gly Ala Asp Lys
                85                  90                  95

Ser Arg Leu Phe Ile Met Asp Ser Thr Tyr Met Ala Asp Lys Asn Pro
            100                 105                 110

Leu Ile Glu Arg Gly Ala Pro Tyr
            115                 120
```

GLYCOSYNTHASE VARIANTS FOR GLYCOPROTEIN ENGINEERING AND METHODS OF USE

CROSS-REFERENCE TO RELATED APPLICATIONS

This application claims the benefit of U.S. Patent Application No. 62/690,669, filed on Jun. 27, 2018, the disclosure of all of which are incorporated by reference herein in their entirety.

FIELD

The present disclosure relates to glycosynthase enzymes for homogeneous antibody engineering/remodeling. EndoSd-D232 and EndoSz-D234 mutants contain the glycan conjugation enzymatic activity at the conserved N297 glycosylation site of Fc region. The present disclosure demonstrated that glycosynthase activities of EndoSd and EndoSz mutants can be applied on various mAbs targeting different receptors, including OBI-888 (Globo H ganglioside), Herceptin (Her 2 receptor), Perj eta (Her 2 receptor), Erbitux (EGFR receptor), Rituxan (CD20 receptor), OBI-898 (SSEA4 ganglioside), Vectibix (EGFR receptor), Humira (TNFα inactivating), Keytruda (PD-1) and Bavencio (PD-L1). Both mAb-GlcNAc and mAb-GlucNAc(F) were suitable substrates for both EndoSd-D232M and EndoSz-D234M. The ADCC assay of related products showed that the remodeled homogeneous antibody (mAb-G2S2) increased relative activity by several folds.

BACKGROUND

Numerous surface carbohydrates are expressed in malignant tumor cells. For example, the carbohydrate antigen Globo H (Fucα1→2 Galβ1→3 GalNAcβ1→3 Galα1→4 Galβ1→4 Glc) was first isolated as a ceramide-linked Glycolipid and identified in 1984 from breast cancer MCF-7 cells. (Bremer E G, et al. (1984) J Biol Chem 259:14773-14777). Previous studies have also shown that Globo H and stage-specific embryonic antigen 3 (Galβ1→3GalNAcβ1→3Galα1→4Galβ1→4Glcβ1) (SSEA-3, also called Gb5) were observed on breast cancer cells and breast cancer stem cells (WW Chang et al. (2008) Proc Natl Acad Sci USA, 105(33): 11667-11672). In addition, SSEA-4 (stage-specific embryonic antigen-4) (Neu5Acα2→3Galβ1→3GalNAcβ1→3Galα1→4Galβ1→4Glcβ1) has been commonly used as a cell surface marker for pluripotent human embryonic stem cells and has been used to isolate mesenchymal stem cells and enrich neural progenitor cells (Kannagi R et al. (1983) EMBO J, 2:2355-2361). These findings support that Globo series antigens (Globo H, SSEA-3 and SSEA-4) can be unique targets for cancer therapies and may be used to direct therapeutic agents to targeting cancer cells effectively.

Program death 1 (PD-1) is an inhibitory receptor expressed on T cells, B cells, or monocytes (Ishida et al. (1992) EMBO J. 11: 3887-2895; Agata et al. (1996) Int. Immunol. 8: 765-772). PD-L1 and PD-L2 are ligands for PD-1 which have been identified to downregulate T cell activation and cytokine secretion upon binding to PD-1 (Freeman et al. (2000) J Exp Med 192:1027-34; Latchman et al. (2001) Nat Immunol 2:261-8). Engagement of PD-1 with PD-L1 or PD-L2 leads to down-regulation of immune responses. Hence, blocking of the PD-1/PD-L1 pathway has been proposed to attenuate central and peripheral immune responses against cancer. Targeting PD-1 and PD-L1 pathway have shown the clinical efficacy in more than 15 cancer types including melanoma, non-small cell lung cancer (NSCLC), renal cell carcinoma (RCC), bladder carcinoma and Hodgkin's lymphoma (Sharma et al. (2015) Science 348(6230):56-61). However, many patients still fail to respond; in some cases, patients showed initial responses but acquire resistance over time. Therefore, there is an urgent need to identify mechanisms of resistance for combination therapy.

Therapeutic monoclonal antibodies (mAbs) have been developed for the treatment of many diseases, such as cancer, autoimmune, and infectious (Adams, G. P., and Weiner, L. M. (2005) Nat. Biotechnol. 23: 1147-1157; Aggarwal, S. R. (2012) Nat. Biotechnol. 30: 1191-1197; Aggarwal, S. R. (2014) Nat. Biotechnol. 32:323-330). For cancer therapy, several commercial mAbs have been found on the market. Those mAbs recognize particular biomarkers on tumor cell surface and enhance cell apoptosis by different mechanisms, such as turn on antibody-dependent cellular cytotoxicity (ADCC) and complement dependent cytotoxicity (CDC) or blocking signal pathway. Her 2 receptor is the most famous biomarker overexpressed on breast cancer, which enable Roche Company to develop two related mAbs, Herceptin (trastuzumab) and Perj eta (pertuzumab). EGFR receptor is also a well-known target for mAb development. For example, Vectibix (panitumumab) and Erbitux (cetuximab) have been developed by Amgen and Merck Company, respectively, targeting metastatic colorectal cancer therapy. In addition, Rituxan (rituximab, Roche) and Arzerra (ofatumumab, GSK) designed to recognize CD20 receptor are commonly used to treat non-Hodgkin's B-cell lymphomas and chronic lymphocytic leukemia cancer. Most recently, OBI Pharma. Inc. is developing OBI-888 and OBI-898 antibodies base on the ganglioside biomarkers Globo H and SSEA-4, which are found in breast, lung, ovary, stomach and small-cell lug (Hakomori, S. I. (2008) Biochim. Biophys. Acta. 1780: 325-346; Hakomori, S. and Zhang, Y. (1997) Chem. Biol. 4:97-104; Zhang, S. et al. (1997) Int. J. Cancer 73: 42-49; Zhang, S. et al. (1997) Int. J. Cancer 73: 50-56.) but not detectable in normal cell. Erbitux, Rituxan, Arzerra, OBI-888 and OBI-898 kill cancer cells through cytotoxicity in terms of ADCC and CDC. Moreover, several mAbs have been developed to block the function of protein-protein interaction. For example, Humira (adalimumab, AbbVie) blocks the TNF-α receptor mediate signal pathway for autoimmune disease, rheumatoid arthritis; Keytruda (pembrolizumab, Merck) blocks PD-1 receptor to destroy the protective mechanism of cancer cells that treats metastatic melanoma. Compare with small molecular drugs, mAbs are more specific to the target cells and have relatively smaller side-effect to the patients. These two important features have become powerful tools against various diseases.

Monoclonal antibodies (mAbs) have molecular weight ~150 kDa composed of two heavy chains (~50 kDa) and two light chains (~25 kDa), which form three domains separated by flexible hinge region. Two Fab domains contain variable complementarity-determining region (CDR) for identifying antigen. One Fc domain is a constant region with N-glycan for mediation of ADCC and CDC cytotoxicity (Jefferis, R. (2009) Nat. Rev. Drug Discov. 8:226-234). The amino acid N297 at the Fc domain is a conserved N-glycosylation site which connects with heterogeneous glycan types, such as biantennary (M3, GOF, G1F, G2F, G0, G1 and G2 complex type) and triantennary (high-mannose and hybrid types), while expressed in various cell systems. The X-ray structure analysis results indicated that the core fucose of Fc glycan obstructed the particular carbohydrate-carbohydrate interactions between Fc and FcγRIIIa and, as a result, decreased the binding constant for approximately hundred folds (Ferrara, C. et al. (2011) Proc. Natl. Acad. Sci. USA 108: 12669-12674) and, as a result, reduced cell killing efficiency. The most common cell system used in the industry is CHO cell. CHO cell generally produce the mAbs that contain glycan compositions predominately in the form of G0F, G1F and G2F. These glycan forms limit the activity of mAbs due to the reduced ADCC binding efficiency caused by fucose. Although modified CHO cell systems have been available by FUT8 (α-1,6-fucosyltransferase 8) gene knock-out (Yamane-Ohnuki, N. and Satoh, M. (2009) MAbs, 1: 230-236; Yamane-Ohnuki, N. et al. (2004) Biotechnol. Bioeng. 87: 614-622) or up-regulation of bisecting GlcNAc (N-acetylglycosamine) transferase GnT-III (Umana, P. et al. (1999) Nat. Biotechnol. 17: 176-180) to reduce the glycan complicity of mAbs, to find a better and more general method to obtain the desired N-glycan on mAbs is still in great interests. In addition, it has also reported that removing the Fc glycan will result in losing the ADCC activity (Kurogochi, M. et al. (2015) PLoS One 10: e0132848). According to the above observations, mAbs cytotoxicity can be effectively controlled by the N-glycan type attached on the Fc region.

Enzymatic modification of Fc region is a solution to establish homogeneous mAbs. Few years ago Lai-Xi Wang and coworkers have tried the chemoenzymatic remodeling by removing the glycan mixture and conjugating homogeneous glycans (Huang, W. et al. (2012) J. Am. Chem. Soc. 134: 12308-12318). Several endo-β-N-acetylglycosaminidases (ENGases) have been reported to remove glycan mixture on mAbs. For instance, EndoD (Tai, T. et al. (1975) J. Biol. Chem. 250: 8569-8575), EndoH (Tarentino, A. L. et al. (1974) J. Biol. Chem. 249: 818-824), EndoLL (Kurogochi, M. et al. (2015) PLoS One 10: e0132848) and EndoM (Kadowaki, S. et al. (1990) Agric. Biol. Chem. 54: 97-106) are able to hydrolyze the glycan with high mannose or terminal mannose types. EndoS (Collin M and Olsen A. (2001) EMBO J. 20: 3046-3055) and EndoSd (Shadnezhad, A. et al. (2016) Future Microbiol 11: 721-736.) have the ability to hydrolyze non-fucosylated and fucosylated N-glycans on the Fc domain, but not high-mannose types. So far, none of signal endoglycosidase could completely hydrolyze all glycan types on mAbs. The EndoS crystal structure was recently solved, which revealed five functional domains (Trastoy, B. et al. (2014) Proc. Natl. Acad. Sci. USA 111: 6714-6719), in which the endoglycosidase domain is highly conserved with rigid β-barrel structure that suitable for site mutation studies. On the other hand, glycosynthases for antibody Fc were also reported. EndoD-N322Q (Fan, S. Q. et al. (2012) J. Biol. Chem. 287: 11272-11281) and EndoM-N175Q (Umekawa, M., Li, C. et al. (2010) J. Biol. Chem. 285: 511-521) only transferred short chain complex-type N-glycan to Fc. Endo-F3-D165Q (Giddens, J. P. et al. (2016) J. Biol. Chem. 291: 9356-9370) only transferred glycan to the fucosylated Fc domain. EndoS-D233Q (Huang, W. et al. (2012) J. Am. Chem. Soc. 134: 12308-12318) enables conjugation of various bi-antennary complex type, whereas EndoS2-D184M (Li., T., Tong, et al. (2016) J. Biol. Chem. 291: 16508-16518) has wild substrates including complex, high-mannose and hybrid types.

SUMMARY OF INVENTION

The present disclosure relates to selected variants of endoglycosidase from *Streptococcus* that possess/display improved enzymatic activities for the synthesis of glycoproteins and/or glycopeptides comprising broad range of well-defined N-glycans of high mannose, hybrid and complex types. In particular, one or more embodiments of present invention also relate to use of these enzyme variants for efficient glycan remodeling of therapeutic antibodies to form homogenous glycan compositions at the Fc-domain for improved of their effector functions.

In the present disclosure, two glycosynthase enzyme variants are provided, EndoSd-D232M and EndoSz-D234M, which have the glycosynthase activity that enable the production of homogeneous mAbs remodeling. Besides the previously reported EndoSd from *Streptococcus dysgalactiae* subsp. *Dysgalactiae* (NCBI GenBank accession No.: ANI26082.1), we have identified and isolated novel enzymes by protein BLAST database on the EndoS and EndoSd sequences. We selected EndoSz from *Streptococcus equi* subsp. *Zooepidemicus* Sz105 (NCBI GenBank accession No.: KIS14581.1) as another candidate despite it is a putative protein. We generated EndoSd and EndoSz mutants according to multiple sequence alignment. The results showed that both mutated enzymes have unexpectedly improved/enhanced glycosynthase activity to conjugate bi-antennary complex-type glycan to mAbs. The mAbs suitable for conjugation are obtained/derived from a wide-range targets of various biomarkers or different IgG types. We demonstrated that the conjugation results of OBI-888, Herceptin, Perj eta, Erbitux, Rituxan, OBI-898, Vectibix, Humira, Keytruda and Bavencio were satisfactory. We also demonstrated the enzyme efficiency in the conjugation reaction and compared the ADCC activities between heterogeneous and homogeneous mAbs in the related cell systems.

```
SEQ ID NO 1:
Name: EndoSd-D232M amino acid sequence
Organism: Streptococcus dysgalactiae subsp.
Dysgalactiae
MGTILGTHHDSLISVKAEEKITQVSQTSTSIDDLHYLSENSKKEFKE

ELSKEKVPEKVKEILSKAQQANKQAQELAEMKVPDKIPMKPLNGPLY

GGYFRTWHDKTSDPLEKDKVNSMGELPKEVDLAFVFHDWTKDYSLFW

KELATKHVPKLNKQGTRVIRTIPWRFLAGGDNSGIAEDASKYPNTPE

GNKALAKAIVDEYVYKYNLDGLDVMIEHDSIPKVNGEASDENLKRSI

DVFEEIGKLIGPKGADKSRLFIMDSTYMADKNPLIERGAPYIDLLLV

QVYGSQGEQGEFQNDTKSVTKTPEERWQGYSKYIRPEQYMIGFSFYE

EKAGSGNLWYDINARKDEDTANGINDDITGTRAERYARWQPKTGGVK

GGIFSYAIDRDGVAHQPKQIAEKDKQSVKNNRPLISEITDNIFHSNY

SVSKTLKTVMLKDKAYDLIDEKDFPDKALREAVMAQVGTRKGDLERF

NGTLRLDNPAIQSLEGLNKFKKLAQLDLIGLSRIIKLDQSVLPANMK

PGKDPLETVLETYKKNGKEEPAIIPPVSLTVSGLTGLKELDLSGFDR

ETLAGIDAATLTSLEKVDISDNKLDLAPKTENRQIFDVMLSTVNNNA

GISEQSIKFDNQKPAGNYPQTYGATNLQLPVRQEKIDLQHQLLFGTI

TNQGTLINSEADYKTYRNQKIAGRNFVDPDYPYNNFKVSHDNYTVKV

TDSTLGTTTDKMLATDKEETYKVDFFSPTDKTKAVHTAKVIVGDEKT

MMVNLAEGATVIKSENDENAQKVFNGIMEYNPLSFNNKSSIIFEIKD

PSLAKYWRLFNDSSKDKKDYIKEAKLEVFTGQLNAEADVKTILEKPD
```

-continued
NWVTVSTYSGEEKVFSHSLDNISAKYWRVTVDNKKDQYGYVSLPELQ

ILGYPLPNADTIMKTVTVAKELSQQKDKFPQQLLDESTAKEAVVEAS

LNSKLFDTGVINTNVEALKNVVDECLAYEKNKETAFKATEDYRAAVN

GVKAESVTVEEMAQLKDLIGKAAHLNSKIDAKLADREYDKDLLGLIG

ELTNITRTVKSFVKHHHHHH

SEQ ID NO 2:
Name: EndoSz-D234M amino acid sequence
Organism: *Streptococcus equi* subsp.
*Zooepidemicus* Sz105
MVAILAAQHDSLIRVKAEDKLVQTSPSVSAIDALHYLSENSKKEFKE

ELSKVEKAQPEKLKEIVSKAQQADKQAKTLAEMKVPEKIPMKPLKGP

LYGGYFRTWHDKTSDPAEKDKVNSMGELPKEVDLAFVFHDWTKDYSL

FWQELATKHVPTLNKQGTRVIRTIPWRFLAGGDHSGIAEDAQKYPNT

PEGNKALAKAIVDEYVYKYNLDGLDVMIERDSIPKVNKEESKEGIER

SIQVFEEIGKLIGPKGADKSRLFIMDSTYMADKNPLIERGAPYIDLL

LVQVYGTQGEKGGFDNANHKAVDTMEERWESYSKYIRPEQYMVGFSF

YEEKANSGNLWYDVNVEDDTNPNIGSEIKGTRAERYAKWQPKTGGVK

GGIFSYGIDRDGVAHPKKNGPKTPDLDKIVKSDYKVSKALKKVMEND

KSYELIDQKDFPDKALREAVIAQVGSRRGNLERFNGTLRLDNPDIKS

LEGLNKLKKLAKLELIGLSQITKLDSSVLPENIKPTKDTLVSVLETY

KNDDRKEEAKAIPQVALTISGLTGLKELNLAGFDRDSLAGIDAASLT

SLEKVDLSSNKLDLAAGTENRQILDTMLATVTKHGGVSEKTFVFDHQ

KPTGLYPDTYGTKSLQLPVANDTIDLQAKLLFGTVTNQGTLINSEAD

YKAYQEQEIAGHRFVDSSYDYKAFAVTYKDYKIKVTDSTLGVTDHKD

LSTSKEETYKVEFFSPINSTKPVHEAKIVVGEEKTMMVNLAEGATII

GGDADPTNAKKVFDGLLNNDTTTLSTSNKASIIFELKEPGLVKHWRF

FNDSKISKADYIKEAKLEAFVGHLEDSSKVKDSLEKSTEWVTVSDYS

GEAQEFSQPLNNIGAKYWRITIDNKKSQYGYVSLPELQIIGHRLPEA

ATVMTTMAAAEELSQQKDKFSQEQLKELEVKVAALKAALDNKMFNAD

TINASFADVKAYIDKLLADAAGKKTLGKATKEAQPVATDAKEKAESE

NPKADHHHHHH

SEQ ID NO 3:
Name: EndoSd-D232M nucleic acid sequence
Organism: *Streptococcus dysgalactiae* subsp.
*Dysgalactiae*
ATGGGCACCATCCTGGGTACCCACCACGACAGCCTGATCAGCGTGAA

GGCGGAGGAAAAAATTACCCAAGTTAGCCAAACCAGCACCAGCATTG

ACGATCTGCACTACCTGAGCGAAAACAGCAAGAAAGAGTTCAAAGAG

GAGCTGAGCAAGGAGAAAGTGCCGGAAAAGGTTAAAGAGATCCTGAG

CAAAGCGCAGCAAGCGAACAAGCAGGCGCAAGAGCTGGCGGAAATGA

AGGTGCCGGACAAAATTCCGATGAAGCCGCTGAACGGTCCGCTGTAT

GGTGGCTACTTTCGTACCTGGCACGACAAAACCAGCGATCCGCTGGA

AAAGGACAAAGTTAACAGCATGGGCGAACTGCCGAAAGAGGTGGATC

TGGCGTTCGTTTTTCACGACTGGACCAAAGATTATAGCCTGTTCTGG

AAAGAGCTGGCGACCAAGCACGTGCCGAAGCTGAACAAACAGGGTAC

CCGTGTTATCCGTACCATTCCGTGGCGTTTTCTGGCGGGTGGCGACA

ACAGCGGTATTGCGGAAGATGCGAGCAAGTACCCGAACACCCCGGAG

GGTAACAAAGCGCTGGCGAAGGCGATTGTGGACGAATACGTTTATAA

ATACAACCTGGACGGTCTGGATGTGATGATCGAGCACGATAGCATTC

CGAAAGTTAACGGCGAAGCGAGCGACGAGAACCTGAAGCGTAGCATC

GATGTGTTCGAGGAAATCGGTAAACTGATTGGTCCGAAAGGCGCGGA

CAAGAGCCGTCTGTTTATTATGGACAGCACCTATATGGCGGATAAGA

ACCCGCTGATCGAACGTGGCGCGCCGTATATTGACCTGCTGCTGGTG

CAGGTTTACGGTAGCCAGGGCGAGCAGGGTGAATTCCAAAACGATAC

CAAAAGCGTTACCAAGACCCCGGAGGAACGTTGGCAGGGCTATAGCA

AATACATCCGTCCGGAGCAATATATGATTGGTTTCAGCTTTTACGAG

GAAAAGGCGGGTAGCGGCAACCTGTGGTACGACATCAACGCGCGTAA

AGACGAAGATACCGCGAACGGCATCAACGACGATATTACCGGTACCC

GTGCGGAGCGTTATGCGCGTTGGCAGCCGAAAACCGGTGGCGTGAAG

GGTGGCATCTTTAGCTACGCGATTGACCGTGATGGTGTTGCGCACCA

GCCGAAGCAAATCGCGGAAAAGGACAAACAAAGCGTGAAAAACAACC

GTCCGCTGATCAGCGAGATTACCGATAACATTTTCCACAGCAACTAT

AGCGTGAGCAAGACCCTGAAAACCGTTATGCTGAAGGACAAAGCGTA

CGACCTGATCGATGAAAAAGACTTTCCGGATAAAGCGCTGCGTGAGG

CGGTGATGGCGCAGGTTGGCACCCGTAAGGGTGACCTGGAACGTTTC

AACGGCACCCTGCGTCTGGATAACCCGGCGATCCAGAGCCTGGAGGG

TCTGAACAAGTTTAAGAAACTGGCGCAACTGGACCTGATTGGCCTGA

GCCGTATCATTAAACTGGATCAAAGCGTGCTGCCGGCGAACATGAAG

CCGGGTAAAGACCCGCTGGAAACCGTTCTGGAGACCTACAAGAAAAA

CGGCAAAGAGGAGCCGGCGATCATTCCGCCGGTTAGCCTGACCGTTA

GCGGTCTGACCGGTCTGAAAGAACTGGACCTGAGCGGCTTCGATCGT

GAGACCCTGGCGGGTATCGATGCGGCGACCCTGACCAGCCTGGAAAA

GGTGGACATTAGCGATAACAAACTGGACCTGGCGCCGAAGACCGAGA

ACCGTCAGATCTTCGATGTGATGCTGAGCACCGTTAACAACAACGCG

GGTATCAGCGAGCAGAGCATTAAATTTGACAACCAAAAGCCGGCGGG

CAACTATCCGCAAACCTACGGTGCGACCAACCTGCAGCTGCCGGTTC

GTCAAGAAAAAATCGACCTGCAGCACCAACTGCTGTTCGGCACCATC

ACCAACCAGGGTACCCTGATTAACAGCGAGGCGGATTATAAACCTA

CCGTAACCAAAAGATTGCGGGTCGTAACTTCGTGGACCCGGATTATC

CGTACAACAACTTTAAAGTTAGCCACGACAACTATACCGTGAAGGTT

ACCGATAGCACCCTGGGCACCACCACCGACAAAATGCTGGCGACCGA

TAAAGAGGAAACCTACAAGGTGGACTTCTTTAGCCCGACCGATAAGA

CCAAAGCGGTTCACACCGCGAAAGTGATCGTTGGCGACGAAAAGACC

ATGATGGTGAACCTGGCGGAGGGTGCGACCGTTATCAAAGCGGAAA

CGATGAAAACGCGCAGAAGGTTTTCAACGGTATTATGGAATATAACC

CGCTGAGCTTCAACAACAAGAGCAGCATCATTTTTGAGATCAAAGAC
CCGAGCCTGGCGAAGTATTGGCGTCTGTTCAACGATAGCAGCAAAGA
CAAGAAAGATTACATCAAGGAAGCGAAACTGGAAGTGTTTACCGGTC
AGCTGAACGCGGAAGCGGACGTTAAAACCATTCTGGAGAAGCCGGAT
AACTGGGTGACCGTTAGCACCTATAGCGGCGAGGAAAAGGTGTTTAG
CCACAGCCTGGACAACATCAGCGCGAAATACTGGCGTGTGACCGTTG
ACAACAAGAAAGATCAGTATGGCTACGTTAGCCTGCCGGAGCTGCAA
ATCCTGGGTTACCCGCTGCCGAACGCGGATACCATTATGAAAACCGT
GACCGTTGCGAAGGAACTGAGCCAGCAAAAGGACAAATTCCCGCAGC
AACTGCTGGATGAGAGCACCGCGAAGGAAGCGGTGGTTGAGGCGAGC
CTGAACAGCAAACTGTTTGACACCGGTGTGATCAACACCAACGTTGA
AGCGCTGAAGAACGTGGTTGATGAGTGCCTGGCGTATGAAAAGAACA
AAGAGACCGCGTTCAAGGCGACCGAAGACTACCGTGCGGCGGTGAAC
GGTGTTAAAGCGGAGAGCGTGACCGTTGAGGAAATGGCGCAGCTGAA
AGATCTGATCGGCAAGGCGGCGCACCTGAACAGCAAAATTGACGCGA
AGCTGGCGGATCGTGAATACGACAAAGATCTGCTGGGCCTGATCGGC
GAGCTGACCAACATTACCCGTACCGTGAAAAGCTTTGTTAAGTGA

SEQ ID NO 4:
Name: EndoSz-D234M nucleic acid sequence
Organism: Streptococcus equi subsp.
Zooepidemicus Sz105
ATGGTTGCGATCCTGGCGGCGCAACACGATAGCCTGATTCGTGTGAA

GGCGGAGGACAAACTGGTGCAGACCAGCCCGAGCGTTAGCGCGATTG

ATGCGCTGCACTACCTGAGCGAAAACAGCAAGAAAGAATTCAAAGAG

GAACTGAGCAAGGTTGAAAAAGCGCAACCGGAGAAGCTGAAAGAAAT

CGTGAGCAAGGCGCAGCAAGCGGACAAGCAGGCGAAAACCCTGGCGG

AGATGAAGGTTCCGGAAAAAATTCCGATGAAGCCGCTGAAAGGCCCG

CTGTATGGTGGCTACTTTCGTACCTGGCACGATAAAACCAGCGACCC

GGCGGAGAAGGATAAAGTGAACAGCATGGGCGAGCTGCCGAAAGAAG

TGGACCTGGCGTTCGTTTTTCACGATTGGACCAAGGACTATAGCCTG

TTCTGGCAAGAACTGGCGACCAAACACGTTCCGACCCTGAACAAGCA

GGGCACCCGTGTGATCCGTACCATTCCGTGGCGTTTTCTGGCGGGTG

GCGATCACAGCGGTATCGCGGAGGACGCGCAGAAATACCCGAACACC

CCGGAAGGCAACAAGGCGCTGGCGAAAGCGATTGTGGATGAGTACGT

TTATAAGTACAACCTGGACGGTCTGGATGTTATGATCGAACGTGACA

GCATTCCGAAGGTGAACAAAGAGGAAAGCAAAGAGGGTATCGAACGT

AGCATTCAGGTTTTCGAGGAAATCGGCAAGCTGATTGGTCCGAAGGG

CGCGGATAAAAGCCGTCTGTTTATCATGGATAGCACCTATATGGCGG

ACAAGAACCCGCTGATCGAGCGTGGTGCGCCGTATATTGACCTGCTG

CTGGTGCAGGTTTACGGTACCCAGGGCGAAAAAGGTGGCTTCGATAA

CGCGAACCACAAGGCGGTTGACACCATGGAGGAACGTTGGGAGAGCT

ATAGCAAATACATCCGTCCGGAACAATATATGGTGGGTTTCAGCTTT

TACGAGGAAAAGGCGAACAGCGGCAACCTGTGGTACGACGTGAACGT

-continued

TGAGGACGATACCAACCCGAACATCGGTAGCGAGATTAAAGGCACCC

GTGCGGAACGTTATGCGAAGTGGCAGCCGAAAACCGGTGGCGTTAAG

GGTGGCATCTTTAGCTACGGTATTGACCGTGATGGCGTGGCGCACCC

GAAGAAAAACGGTCCGAAAACCCCGGACCTGGATAAGATCGTGAAAA

GCGATTATAAAGTTAGCAAAGCGCTGAAGAAAGTTATGGAGAACGAC

AAGAGCTACGAACTGATCGACCAAAAGGATTTCCCGGACAAAGCGCT

GCGTGAGGCGGTGATTGCGCAGGTTGGTAGCCGTCGTGGCAACCTGG

AACGTTTTAACGGTACCCTGCGTCTGGATAACCCGGACATCAAAAGC

CTGGAGGGCCTGAACAAACTGAAGAAACTGGCGAAGCTGGAACTGAT

CGGTCTGAGCCAAATTACCAAGCTGGATAGCAGCGTTCTGCCGGAGA

ACATTAAGCCGACCAAAGACACCCTGGTGAGCGTTCTGGAAACCTAC

AAAAACGACGATCGTAAGGAAGAGGCGAAAGCGATCCCGCAGGTGGC

GCTGACCATTAGCGGTCTGACCGGCCTGAAGGAGCTGAACCTGGCGG

GTTTCGACCGTGATAGCCTGGCGGGTATTGATGCGGCGAGCCTGACC

AGCCTGGAGAAAGTGGATCTGAGCAGCAACAAGCTGGACCTGGCGGC

GGGTACCGAAAACCGTCAAATTCTGGACACCATGCTGGCGACCGTGA

CCAAACACGGTGGCGTTAGCGAGAAGACCTTCGTGTTTGATCACCAG

AAACCGACCGGTCTGTATCCGGACACCTACGGCACCAAGAGCCTGCA

GCTGCCGGTTGCGAACGATACCATCGACCTGCAAGCGAAACTGCTGT

TCGGTACCGTGACCAACCAGGGCACCCTGATCAACAGCGAAGCGGAC

TATAAGGCGTACCAGGAGCAAGAAATTGCGGGCCACCGTTTCGTTGA

TAGCAGCTATGACTACAAAGCGTTTGCGGTGACCTACAAGGATTACA

AGATCAAGGTTACCGACAGCACCCTGGGTGTGACCGATCACAAAGAC

CTGAGCACCAGCAAAGAGGAGACCTATAAAGTTGAGTTCTTTAGCCC

GATCAACAGCACCAAACCGGTGCACGAAGCGAAGATTGTGGTTGGCG

AGGAAAAGACCATGATGGTTAACCTGGCGGAGGGCGCGACCATCATT

GGTGGCGACGCGGACCCGACCAACGCGAAGAAAGTGTTCGATGGCCT

GCTGAACAACGACACCACCACCCTGAGCACCAGCAACAAAGCGAGCA

TCATTTTTGAGCTGAAAGAACCGGGTCTGGTGAAGCACTGGCGTTTC

TTTAACGATAGCAAGATCAGCAAAGCGGACTACATTAAAGAGGCGAA

ACTGGAAGCGTTCGTTGGTCACCTGGAAGATAGCAGCAAGGTGAAAG

ACAGCCTGGAGAAAAGCACCGAATGGGTGACCGTTAGCGATTATAGC

GGCGAGGCGCAGGAATTTAGCCAACCGCTGAACAACATCGGCGCGAA

GTACTGGCGTATCACCATTGACAACAAGAAAAGCCAGTATGGTTACG

TTAGCCTGCCGGAGCTGCAAATCATTGGTCATCGTCTGCCGGAAGCG

GCGACCGTGATGACCACCATGGCGGCGGCGGAGGAACTGAGCCAGCA

AAAGGATAAATTCAGCCAGGAGCAACTGAAGGAGCTGGAAGTGAAAG

TTGCGGCGCTGAAGGCGGCGCTGGATAACAAAATGTTCAACGCGGAC

ACCATCAACGCGAGCTTTGCGGACGTTAAAGCGTACATTGATAAGCT

GCTGGCGGACGCGGCGGGTAAGAAAACCCTGGGCAAAGCGACCAAAG

-continued

```
AGGCGCAGCCGGTGGCGACCGATGCGAAGGAAAAAGCGGAGAGCGAA

AACCCGAAGGCGGACTAA
```

In one aspect, the present invention provides the glycosynthase enzymes variants, wherein the variants have at least about 80%, 81, 82, 83, 84, 85, 86, 87, 88, 89, 90, 91, 92, 93, 94, 95, 96, 97, 98, 99% sequence and/or structural homology thereto and exhibit improved transglycosylation activity on both fucosylated and non-fucosylated GlcNAc acceptors against broad range of N-glycans of high mannose, hybrid and complex types, wherein the said variants enable efficient transfer of an activated oligosaccharide donors on fucosylated and non-fucosylated GlcNAc acceptors to form new homogenous glycoform of glycopeptide or glycoprotein or therapeutic antibodies. The EndoSz and EndoSd mutants are listed in the following table:

| EndoSz mutant | EndoSd mutant |
|---|---|
| D234E | D232E |
| D234R | D232R |
| D234H | D232H |
| D234M | D232M |
| D234V | D232V |
| D234L | D232L |
| D234F | D232F |
| D234S | D232S |
| D234T | D232T |
| D234Q | D232Q |
| T183Q | T181Q |
| D232Q | D230Q |
| D280Q | D278Q |
| S281Q | S279Q |
| T282Q | T280Q |

In one aspect, the disclosure provides vectors and cells lines suitable for expressing the peptides of SEQ IDs No 1 or No. 2. In one embodiment, the vector or cell line comprises the nucleotide of SEQ ID No 3 or No. 4.

In one aspect, that the sequence and/or structural homologs can include or exclude natural sequences.

In certain embodiment, the antibody is OBI-888 (Anti-Globo H monoclonal antibody). Exemplary OBI-888 is as described in PCT patent publications (WO2015157629A2 and WO2017062792A1), patent applications, the contents of which are incorporated by reference in its entirety.

In certain embodiment, the antibody is OBI-898 (Anti-SSEA4 monoclonal antibody). Exemplary OBI-898 is as described in PCT patent publication (WO2017172990A1), patent applications, the contents of which are incorporated by reference in its entirety.

In another aspect, a method for preparing an engineered glycoprotein using the glycosynthase variants is provided.

In another aspect, a population of homogeneous antibody prepared by using the glycosynthase variants is provided.

BRIEF DESCRIPTION OF THE DRAWINGS

FIG. 4. The multiple sequence alignment of exemplary EndoS2, EndoS, EndoSz and EndoSd (SEQ ID NOs: 5-8). The blue triangle indicated the selected sites for site-direct mutagenesis study in EndoSz and EndoSd enzymes.

ABBREVIATIONS

Figure 1:
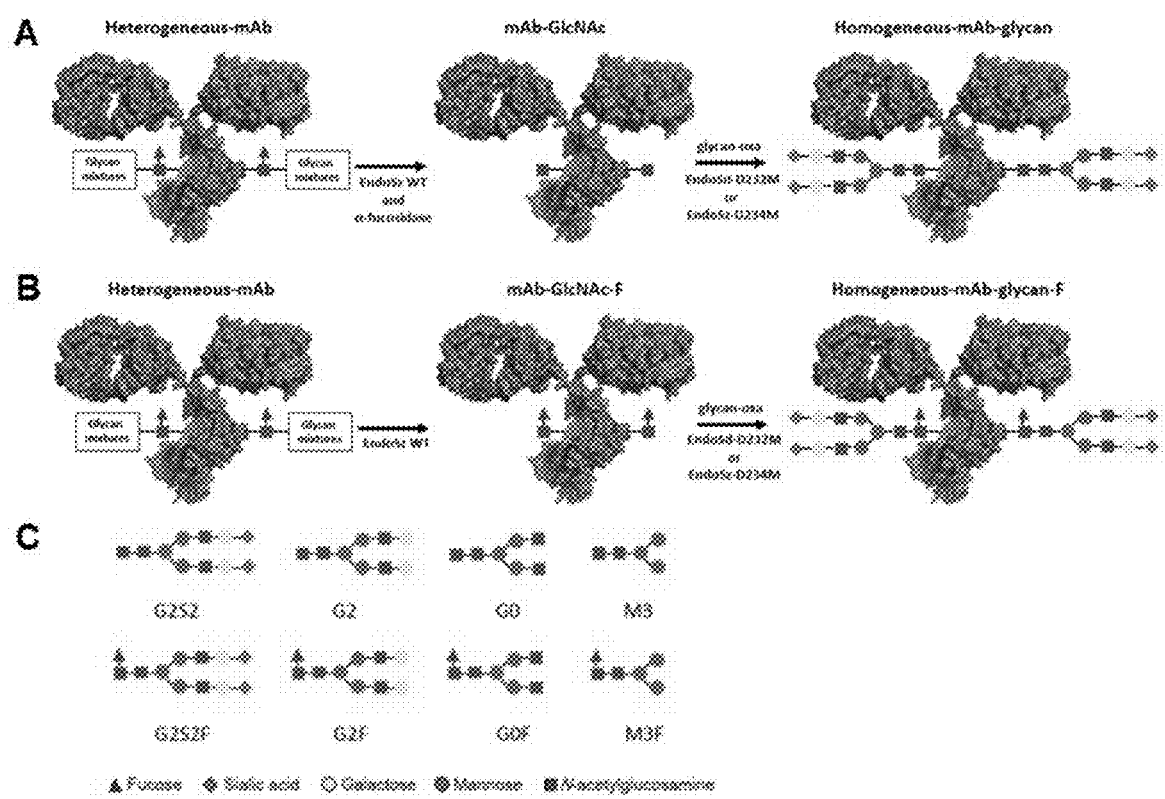
FIG. 1. Summarizes aspects of the overall process of homogeneous platform. (A) The cell expressed mAbs were heterogeneous with glycan mixtures which were removed by wild type EndoSz and α-fucosidase to generate mAb-GlcNAc. Then the EnodSd-D232M and EnodSz-D234M were used to conjugate glycan-oxazoline and produce homogeneous mAbs. (B) In the glycan cleavage step, only EndoSz enzyme is used to generate mAbs-GlcNAc-F and the product will be homogeneous-mAb-glycan-F after conjugation. (C) The exemplary picture of biantennary glycans.

ACN: acetonitrile; ADCC: antibody-dependent cellular cytotoxicity; CDC: complement dependent cytotoxicity; CDR: complementarity-determining region; FA: Formic acid; FUT8: α-1,6-fucosyltransferase 8; GlcNAc: N-acetylglycosamine; HFIP: 1,1,1,3,3,3-Hexafluoro-2-propanol; IPTG: isopropyl-β-D-thiogalactopyranoside; TFA: trifluoroacetic acid.

DETAILED DESCRIPTION OF THE INVENTION

N-glycosylation is one of the most complex post-translational modifications that often result in a remarkable heterogeneity of glycan structures including high mannose, hybrid and complex types, depending on the recombinant expression system. Commercially available therapeutic antibodies typically exist as mixtures of glycoforms that are not optimal for their respective therapeutic activities. Recently, glycoengineering has gathered attention to control Fc glycosylation for improving efficacy.

A typical IgG consists of two antigen-binding fragments (Fabs), which are connected via a flexible region to a constant region (Fc). The Fab domains are responsible for antigen recognition while the N-glycan at Asn297 of Fc domain interact with respective Fcγ receptors (such as FcγRIIIa and FcγRIIb) on effector cells and C1q component of the complements that activate the effector functions, including antibody-dependent cellular cytotoxicity (ADCC) and complement-dependent cytotoxicity (CDC). Almost all therapeutic antibodies are N-glycosylated on each of the homodimeric Fc domains at the conserved asparagine residue (N297). These N-linked glycans result in more than 30 different glycoforms, and are typical biantennary complex type with considerable structural heterogeneity, in which the core heptasaccharide can be differentially decorated with core fucose (Fuc), bisecting N-acetylglucosamine (GlcNAc), terminal galactose (Gal), and terminal sialic acid (Sia). The composition of N-glycans could influence the Fc domain conformation, therefore, modulating the antibody's stability, pharmacokinetic profile, immunogenicity, effector functions, antibody-mediated inflammation, and complement activation. For example, the absence of the core fucose, as well as the attachment of a bisecting GlcNAc moiety, dramatically enhances the affinity of antibody for the FcγIIIa receptor (FcγRIIIa) on effector cells, resulting in more effective elimination of the target. In addition, the terminal α-2,6-sialylated glycan, which is a minor component of antibodies and the intravenous immunoglobulin (IVIG), is an optimized structure that enhances the anti-inflammatory properties.

Endoglycosidases, are a family of at least 18 glycoside hydrolase (GH) from the *Streptococcus pyogenes* and have recently become the point of attention for glycoengineering of therapeutic antibodies. These enzymes can catalyze the hydrolysis of the β-1, 4 linkage between the two N-acetylglucosamines (GlcNAcs) in the core of the N-linked glycan of human IgG. Additionally, the enzymes remove complex type glycans at IgG Fc domain.

Embodiments of the present disclosure relate to selected variants of glycosynthase that show remarkable transglycosylation activities to transfer a broad range of N-glycans of high mannose, hybrid or complex types, from activated oligosaccharide oxazolines to fucosylated or non-fucosylated GlcNAc-peptides, proteins or IgGs with little or negligible product hydrolysis. The novel Glycosynthase enzymes acted with surprising efficiency to provide homogeneously glycosylated glycopeptides, glycoproteins and therapeutic antibodies and Fc fragments thereof, having various defined glycoforms. Still further, embodiments of the present invention may provide glycoengineered antibodies with enhancement of their effector functions, such as FcγIIIA bindings and antibody dependent cell mediated cytotoxicity (ADCC) etc., as well as pharmacological properties. Embodiments of the present invention also allow for rapid investigation of effects of diverse Fc glycosylations of therapeutic antibodies on their effector functions.

In accordance with embodiments of the invention, a novel Glycosynthase enzyme comprises a sequence selected from the sequences of SEQ ID NOs. 1-2. These mutants show unexpectedly improved tranglycosylation activities and reduced hydrolyzing activities. Therefore, they can catalyze efficient transfer of activated oligosaccharide donors to core GlcNAc-acceptors, which may be fucosylated or non-fucosylated.

In accordance with certain embodiments, a Glycosynthase enzyme may have a sequence identity of at least about 80% (e.g., 80%, 85%, 90%, 95%, or 98% (or a value ranging between any of the two numbers listed herein) to a sequence in SEQ ID Nos. 1-2 and have the desired transglycosylation activity, or fragment thereof having the transglycosylation activity.

Definitions

It must be noted that as used herein and in the appended claims, the singular forms "a", "an", and "the" include plural reference unless the context clearly dictates otherwise.

As used herein, the term "glycan" refers to a polysaccharide, oligosaccharide or monosaccharide. Glycans can be monomers or polymers of sugar residues and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6' sulfo N-acetylglucosamine, etc.).

As used herein, the terms "fucose," "core fucose," and "core fucose residue" are used interchangeably and refer to a fucose in α-1,6-position linked to the N-acetylglucosamine.

As used herein, the terms "N-glycan", "N-linked glycan", "N-linked glycosylation", "Fc glycan" and "Fc glycosylation" are used interchangeably and refer to an N-linked oligosaccharide attached by an N-acetylglucosamine (GlcNAc) linked to the amide nitrogen of an asparagine residue in a Fc-containing polypeptide. The term "Fc-containing polypeptide" refers to a polypeptide, such as an antibody, which comprises an Fc region.

As used herein, the term "glycosylation pattern" and "glycosylation profile" are used interchangeably and refer to the characteristic "fingerprint" of the N-glycan species that have been released from a glycoprotein or antibody, either enzymatically or chemically, and then analyzed for their carbohydrate structure, for example, using LC-HPLC, or MALDI-TOF MS, and the like. See, for example, the review in Current Analytical Chemistry, Vol. 1, No. 1 (2005), pp. 28-57; herein incorporated by reference in its entirety.

As used herein, the term "glycoengineered Fc" when used herein refers to N-glycan on the Fc region has been altered or engineered either enzymatically or chemically. The term "Fc glycoengineering" as used herein refers to the enzymatic or chemical process used to make the glycoengineered Fc.

The terms "homogeneous", "uniform", "uniformly" and "homogeneity" in the context of a glycosylation profile of Fc region are used interchangeably and are intended to mean a single glycosylation pattern represented by one desired N-glycan species, with little or no trace amount of precursor N-glycan, including, for example, less than 95, 96, 97, 98, 99% starting precursor material.

TABLE 1

Listed the four classes of amino acids.

| Side Chain | Amino Acid |
| --- | --- |
| Basic | Arginine (R), Lysine (K) or Histidine (H) |
| Neutral | Cysteine (C), Tyrosine (Y), Glycine (G), Glutamine (Q), Threonine (T), Asparagine (N) or Serine (S) |
| Hydrophobic | Isoleucine (I), Leucine (L), Methionine (M), Tryptophan (W), Proline (P), Valine (V), Phenylalanine (F) or Alanine (A) |
| Acidic | Aspartic Acid (D) or Glutamic Acid (E) |

As used herein, the terms "IgG", "IgG molecule", "monoclonal antibody", "immunoglobulin", and "immunoglobulin molecule" are used interchangeably.

As used herein, the term "Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see review M. in Daeron (1997) Annu. Rev. Immunol. 15:203-234). FcRs are reviewed in Ravetch and Kinet (1991) Annu. Rev. Immunol 9:457-92; Capel et al. (1994) Immunomethods 4:25-34; Haas et al. (1995) J. Lab. Clin. Med. 126:330-41). Other FcRs, including those to be identified in the future, are encompassed by the term "FcR" herein. The term also includes the neonatal receptor, FcRn, which is responsible for the transfer of maternal IgGs to the fetus (Guyer et al. (1976) J. Immunol. 117:587 and Kim et al. (1994) J. Immunol. 24:249).

The term "effector function" as used herein refers to a biochemical event that results from the interaction of an antibody Fc region with an Fc receptor or ligand. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions can be assessed using various assays known in the art.

As used herein, the term "Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. (1998) PNAS (USA) 95:652-656.

The complex N-linked oligosaccharide on each CH2 domain of IgGs is crucial for the structure of the Fc region and thus the interaction with the Fc receptors (Krapp et al. 2003; Woof and Burton 2004). The oligosaccharide chain at IgG-Fc domain contains several N-Acetyl-Glucosamine (GlcNAc) and mannose (Man) residues, and eventually galactose (Gal) and fucose (Fuc) residues as well as sialic acid (Sia or NANA for N-acetylneuraminic acid). A GlcNAc, with or without α1-6 Fuc, is attached to the Asn297. A GlcNAcβ1-4 is attached to this first GlcNAc. A manβ1-4 is then found, to which two Manα1-6 and Manα1-3 arms are attached. Both arms contain an additional GlcNAcβ1-2 to which a Galβ1-4 can be attached or not. Thus, the carbohydrate chain can contain 0, 1 or 2 galactose residues, defining G0, G1, and G2 glycoforms, respectively. Further variations occur, including the presence of a bisecting GlcNAcβ1-4 and the capping of one or both of the terminal galactose residues with a sialic acid or even a Galα1-3 residue. The enzymatic cleavage of the Fc-glycan with Endoglycosidases causes the Fc region to deform, and thus, dramatically decrease in IgGs binding to Fcγ receptors (Allhorn et al. 2008). Despite of their 37% sequence identity, both EndoS and EndoS2 catalyze the hydrolysis of the β-1,4 linkage between the two N-acetylglucosamines (GlcNAcs) in the core of the N-linked glycan of human IgG. However, in addition to complex type glycans, EndoS2 hydrolyze hybrid and oligomannose structures to a greater extent compared with EndoS (Sjögren et al. 2015).

Since the first antibody therapy was introduced in the 1980s, there are more than 240 therapeutic antibodies in clinical trials and the field is steadily expanding (Chan and Carter 2010). The role of the IgG-Fc glycans on antibody functions has gained a huge attention in the growing field of monoclonal therapeutic antibodies. Therefore, to improve the efficacy of the therapeutic antibodies, the major focus is turning towards the engineering the Fc-glycan that specifically interact with selected Fcγ receptors (Sondermann et al. 2013; Bournazos et al. 2014; Monnet et al. 2014; Quast and Liinemann 2014). Some of the important glycan modifications that dramatically affect the effector functions includes, i) the lack of a core fucose residue attached to the reducing end GlcNAc residue leads to increased affinity for Fcγ RIIIa and thus increased antibody-dependent cytotoxicity (Iidaet et al. 2006); ii) sialic acid rich glycans on IgG that have been claimed to increase the anti-inflammatory response of IgGs through increased interaction with DC-SIGN receptors on dendritic cells and macrophages (Anthony et al. 2008; Anthony and Ravetch 2010; Pincetic et al. 2014); iii) having bisecting GlcNAc induces a strong ADCC as compared to its parental counterpart. The recent improvements in biotechnology tools to control the Fc-glycosylation states of IgG facilitates development of therapeutic antibodies with predefined glycoforms. Accordingly, the Glycosynthase enzymes of present invention is a great advancement in the field for glycoengineering of peptides, proteins, and antibodies of interest to attach broad range of N-glycans of high mannose, hybrid and complex types for functional and structural studies.

In one embodiment, the synthetic glycan oxazoline comprising diverse N-glycans of high mannose, hybrid and complex types having the formula:

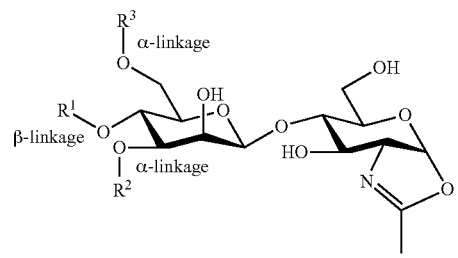

Wherein, $R^1$ is —H or N-acetyl glucosamine attached via β-1, 4 linkage and $R^2$ and $R^3$ are same or different and are independently selected from the group consisting of:

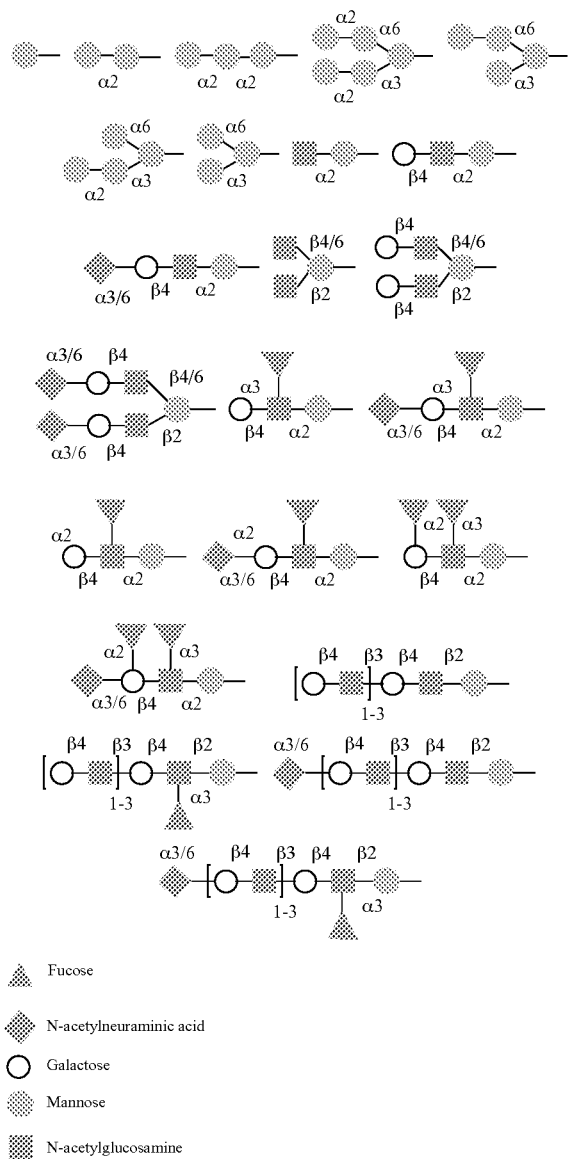

- Fucose
- N-acetylneuraminic acid
- Galactose
- Mannose
- N-acetylglucosamine

In another aspect, the present invention provides exemplary Glycosynthase enzymes for transglycosylation at core fucosylated or non-fucosylated GlcNAc-acceptor, wherein the core fucosylated or non-fucosylated GlcNAc-acceptor comprising core fucosylated or non-fucosylated GlcNAc-peptides, proteins and IgG Fc domain or fragment thereof.

In a separate aspect, the present invention provides a remodeling method of core fucosylated or non-fucosylated GlcNAc-peptide, protein, and IgG or IgG-Fc fragment, wherein the method comprising: providing peptide/protein/antibody-GlcNAc acceptor or Fc fragment and reacting with an activated oligosaccharide donors under the catalysis of *Streptococcus dysgalactiae* subsp. *Dysgalactiae* and *Streptococcus equi* subsp. *Zooepidemicus* Sz105 glycosynthase enzymes, and thereby preparing substantially, essentially, and/or pure glycoforms of pre-existing peptides, proteins and monoclonal antibodies having heterogeneous glycosylation states.

In further aspect, the present invention provides method of using Glycosynthase enzymes for glycan remodeling of therapeutic IgG or Fc fragment thereof, wherein the method comprising:

A. Treating natural or recombinant core fucosylated or non-fucosylated therapeutic IgG or IgG-Fc fragment carrying heterogeneous N-glycans with Endoglycosidase (e.g. wild type EndoS2) together with or without bacterial alpha fucosidases to hydrolyze bond between two reducing end GlcNAc residues to form core fucosylated or non-fucosylated GlcNAc-IgG acceptor;

B. Transferring the wide range of predefined oligosaccharide building units in the form of activated oligosaccharide donors to core fucosylated or non-fucosylated GlcNAc-IgG to reconstitute natural beta 1, 4 linkage through transglycosylation using *Streptococcus dysgalactiae* subsp. *Dysgalactiae* and *Streptococcus equi* subsp. *Zooepidemicus* Sz105 Glycosynthase enzymes, thereby attaching the predefined oligosaccharide to remodel core fucosylated or non-fucosylated IgG or Fc fragment thereof.

In further aspect, the present invention provides a composition of fucosylated or non-fucosylated glyco-engineered antibodies or antigen binding fragments comprising of IgG molecules having the same N-glycan structure at each site of the Fc region, wherein the N-glycan is of high mannose, hybrid, and complex types and is selected from the group consisting of:

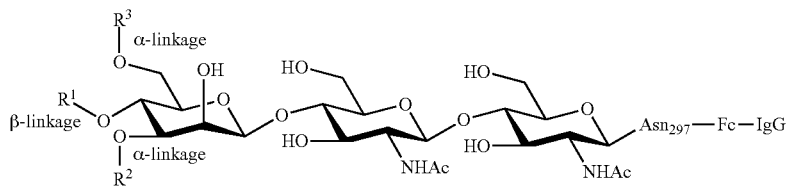

Wherein, $R^1$ is —H or N-acetyl glucosamine attached via β-1, 4 linkage and R and $R^3$ are same or different and are independently selected from the group consisting of:

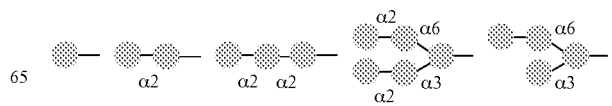

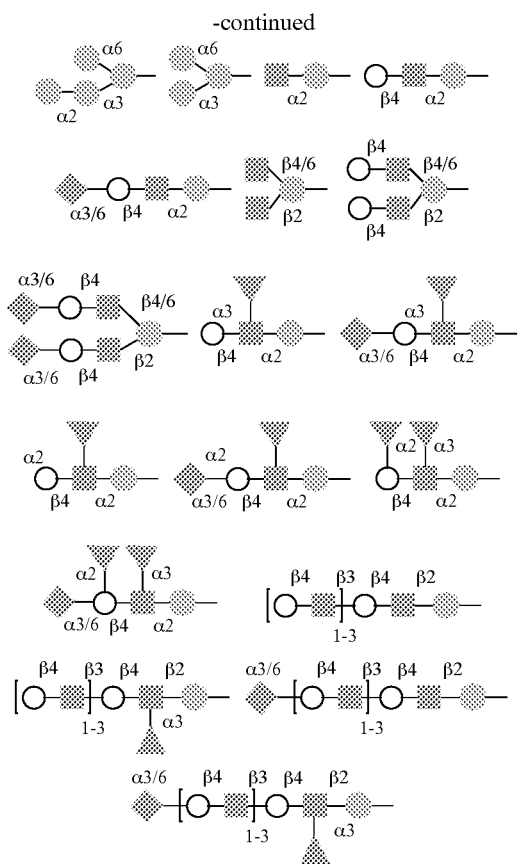

In another aspect, the present invention provides the glycoengineered antibodies with unexpectedly improved effector functions such as bindings to FcγIIIA, ADCC and regulates immune response, as compared to non-modified antibodies.

Another aspect of the present disclosure features a pharmaceutical composition comprising a composition of glycoengineered antibodies described herein and a pharmaceutically acceptable carrier for the treatment of cancer in a patient.

As used herein, examples of cancers include, but not limited to, cancers associated with and/or expressing Globo series antigens, including, but not limited to, Globo H, S SEA-4, S SEA-3; cancers associated with and/or expressing Her-2; cancers associated with and/or expressing EGFR CD20, TNF-α, PD-1 and PD-L1 receptor.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having cancer, which include, but not limited to, sarcoma, skin cancer, leukemia, lymphoma, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer. A subject having cancer can be identified by routine medical examination. Particularly, the cancer is Globo series antigen expressing cancer.

The present invention envisioned glycoengineering of antibodies selected from the group consisting of Herceptin (trastuzumab), Perjeta (pertuzumab), Erbitux (cetuximab), Rituxan (rituximab), Vectibix (panitumumab), Humira (adalimumab), Keytruda (pembrolizumab) and Bavencio (avelumab).

Pharmaceutical Formulations

Therapeutic formulations comprising an antibody of the invention may be prepared for storage by mixing the antibody having the desired degree of purity with one or more optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, including, but not limited to, those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nano-capsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No.

3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(~)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The amount of antibody in the pre-lyophilized formulation is determined taking into account the desired dose volumes, mode(s) of administration etc. Where the protein of choice is an intact antibody (a full-length antibody), from about 2 mg/mL to about 50 mg/mL, preferably from about 5 mg/mL to about 40 mg/mL and most preferably from about 20-30 mg/mL is an exemplary starting protein concentration. The protein is generally present in solution. For example, the protein may be present in a pH-buffered solution at a pH from about 4-8, and preferably from about 5-7. Exemplary buffers include histidine, phosphate, Tris, citrate, succinate and other organic acids. The buffer concentration can be from about 1 mM to about 20 mM, or from about 3 mM to about 15 mM, depending, for example, on the buffer and the desired isotonicity of the formulation (e.g. of the reconstituted formulation). The preferred buffer is histidine in that, as demonstrated below, this can have lyoprotective properties. Succinate was shown to be another useful buffer.

The lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the protein occurs upon lyophilization. Where the lyoprotectant is a sugar (such as sucrose or trehalose) and the protein is an antibody, exemplary lyoprotectant concentrations in the pre-lyophilized formulation are from about 10 mM to about 400 mM, and preferably from about 30 mM to about 300 mM, and most preferably from about 50 mM to about 100 mM.

The ratio of protein to lyoprotectant is selected for each protein and lyoprotectant combination. In the case of an antibody as the protein of choice and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, for example from about 200 to about 600 moles of lyoprotectant to 1 mole antibody.

In preferred embodiments of the invention, it has been found to be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68, etc.). The amount of surfactant added is such that it reduces aggregation of the reconstituted protein and minimizes the formation of particulates after reconstitution. For example, the surfactant may be present in the pre-lyophilized formulation in an amount from about 0.001-0.5%, and preferably from about 0.005-0.05%.

In certain embodiments of the invention, a mixture of the lyoprotectant (such as sucrose or trehalose) and a bulking agent (e.g. mannitol or glycine) is used in the preparation of the pre-lyophilization formulation. The bulking agent may allow for the production of a uniform lyophilized cake without excessive pockets therein etc.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions and formulations described herein are preferably stable. A "stable" formulation/composition is one in which the antibody therein essentially retains its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes, for example.

After the protein, lyoprotectant and other optional components are mixed together, the formulation is lyophilized. Many different freeze-dryers are available for this purpose such as Hull50° (Hull, USA) or GT20° (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hours). A secondary drying stage may be carried out at about 0-40° C., depending primarily on the type and size of container and the type of protein employed. However, it was found herein that a secondary drying step may not be necessary. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial. As a general proposition, lyophilization will result in a lyophilized formulation in which the moisture content thereof is less than about 5%, and preferably less than about 3%.

At the desired stage, typically when it is time to administer the protein to the patient, the lyophilized formulation may be reconstituted with a diluent such that the protein concentration in the reconstituted formulation is at least 50 mg/mL, for example from about 50 mg/mL to about 400 mg/mL, more preferably from about 80 mg/mL to about 300 mg/mL, and most preferably from about 90 mg/mL to about 150 mg/mL. Such high protein concentrations in the reconstituted formulation are considered to be particularly useful where subcutaneous delivery of the reconstituted formulation is intended. However, for other routes of administration, such as intravenous administration, lower concentrations of the protein in the reconstituted formulation may be desired (for example from about 5-50 mg/mL, or from about 10-40 mg/mL protein in the reconstituted formulation). In certain embodiments, the protein concentration in the reconstituted formulation is significantly higher than that in the pre-lyophilized formulation. For example, the protein concentration in the reconstituted formulation may be about 2-40 times, preferably 3-10 times and most preferably 3-6 times (e.g. at least three fold or at least four fold) that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%. Preferably, the reconstituted formulation has less than 6000 particles per vial which are >10 µm in size.

Therapeutic Applications

The glycoengineered antibodies described herein may be used for treating a patient having a cancer. The method of the treatment comprises administering to the patient an effective amount of a glycoengineered antibody or a pharmaceutical composition described herein. Examples of the cancers include, but are not limited to cancers associated with and/or expressing Globo series antigens, including, but not limited to, Globo H, SSEA-4, SSEA-3; cancers associated with and/or expressing Her-2; cancers associated with and/or expressing EGFR receptor.

In certain embodiments, the cancer is a breast cancer.

Further, the glycoengineered antibodies described herein may be used for treating a patient having an autoimmune or inflammatory disease. The method of the treatment comprises administering to the patient an effective amount of a glycoengineered antibody or a pharmaceutical composition described herein. Examples of the autoimmune or inflammatory disease include, but are not limited to, rheumatoid arthritis, juvenile rheumatoid arthritis, systemic lupus erythematosus (SLE), Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Crohn's disease, ulcerative colitis, gastritis, Hashimoto's thyroiditis, ankylosing spondylitis, hepatitis C-associated cryoglobulinemic vasculitis, chronic focal encephalitis, bullous pemphigoid, hemophilia A, membranoproliferative glomerulonephritis, adult and juvenile dermatomyositis, adult polymyositis, chronic urticaria, primary biliary cirrhosis, neuromyelitis optica, Graves' dysthyroid disease, bullous pemphigoid, membranoproliferative glomerulonephritis, Churg-Strauss syndrome, asthma, psoriatic arthritis, dermatitis, respiratory distress syndrome, meningitis, encephalitis, uveitis, eczema, atherosclerosis, leukocyte adhesion deficiency, juvenile onset diabetes, Reiter's disease, Behcet's disease, hemolytic anemia, atopic dermatitis, Wegener's granulomatosis, Omenn's syndrome, chronic renal failure, acute infectious mononucleosis, HIV and herpes-associated disease, systemic sclerosis, Sjogren's syndrome and glomerulonephritis, dermatomyositis, ANCA, aplastic anemia, autoimmune hemolytic anemia (AIHA), factor VIII deficiency, hemophilia A, autoimmune neutropenia, Castleman's syndrome, Goodpasture's syndrome, solid organ transplant rejection, graft versus host disease (GVHD), autoimmune hepatitis, lymphoid interstitial pneumonitis (HIV), bronchiolitis obliterans (non-transplant), Guillain-Barre Syndrome, large vessel vasculitis, giant cell (Takayasu's) arteritis, medium vessel vasculitis, Kawasaki's Disease, and polyarteritis *nodosa*.

In certain embodiments, the autoimmune or inflammatory disease is rheumatoid arthritis.

In these treatment methods, the primary glycoengineered antibody can be administered alone or in conjunction with a second therapeutic agent such as a second antibody, or a chemotherapeutic agent or an immunosuppressive agent.

EXAMPLES

Embodiments of the invention will be further illustrated with the following specific examples. One skilled in the art would appreciate that these specific examples are for illustration only and that other modifications and variations are possible without departing from the scope of the invention. For example, the enzyme variants of the invention may be used to glycoengineer any glycoproteins or glycopeptides, including antibodies. The specific examples described herein use anti-CD20 antibodies. However, one skilled in the art would appreciate that other glycoproteins or antibodies may also be used in a similar manner.

Materials

Monoclonal anti-Globo H antibody, OBI-888 was produced according to our previously procedure disclosed in PCT patent publications (WO2015157629A2 and WO2017062792A1). Monoclonal anti-SSEA4 antibody, OBI-898 was produced according to our previously procedure disclosed in PCT patent publication (WO2017172990A1). The commercial antibodies Herceptin (trastuzumab), Perj eta (pertuzumab), Erbitux (cetuximab), Rituxan (rituximab), Vectibix (panitumumab), Humira (adalimumab), Keytruda (pembrolizumab) and Bavencio (avelumab). were purchased from:

base on mutated sites. Taking EndoSd-D232M and EndoSz-D234M as template vectors, the mutated vectors were amplified by Pfu DNA polymerase (Protech). Then, the template vectors (methylated DNA) were digested by DpnI (Promega) for 2 hours (37° C.). The mutated vectors were transformed to the DH5a competent cell for selection. All mutants were confirmed by DNA sequencing.

All vectors were transformed into BL21 (DE3) and cultured at 37° C. in TB medium containing ampicillin antibiotic (50 µg/mL). The proteins were induced by 0.2 mM isopropyl-β-D-thiogalactopyranoside (IPTG) while the cell density OD600 reached 0.6. After 5 hours, the cells were harvested at 25° C. by centrifugation (BACKMAN/JLA-8.1, 9000 g) for 15 minutes. The cell pellet was resuspension with wash buffer containing 50 mM MOPS pH 7.0, 300 mM NaCl and 10 mM imidazole (100 mL buffer/1 L cell pellet) for the homogenizer (NanoLyzer N-10) to break the cell. After 60 min/12,000 g (BACKMAN/JA-10) centrifugation at 4° C. and discard pellet, the supernatant was mixed with Ni-NTA resin (Roche) and gentle rocked overnight at 4° C. for protein binding completely. The resin was loaded onto open column and washed non-bound protein with wash buffer until the concentration of non-bound protein was less than 1 mg/mL (defined by Bradford assay, Thermo). The bound protein was eluted with elute buffer containing 50 mM MOPS pH 7.0, 300 mM Nacl and 250 mM imidazole. The eluted fraction was dialysis to a storage buffer contain-

|  | Herceptin | Perjeta | Erbitux | Rituxan | Vectibix | Humira | Keytruda | Bavencio |
|---|---|---|---|---|---|---|---|---|
| Brand | Roche | Roche | MerckSerono | Roche | Amgen | AbbVie | MSD Ireland | Merck |
| Lot | N7208B06B3066 | H0239B09 | 245011 | H0229B13 | 1080265 | 83347XH04 | 7302614A13 | 04150132280583 |

Biantennary glycan, Sialylated complex type N-glycan (NSCT), was purchase from Tokyo Chemical Industry Co., Ltd. (Tokyo, Japan, D4065) and NSCT-oxazoline were synthesized according to previously reported (Noguchi, M. et al. (2012) Helvetica chimica acta 95: 1928-1936). Other glycans (M3, G0, and G2) and Bf-α-fucosidase was produced according previous papers (Tsai, T. I. et al. (2017) ACS Chem. Biol. 12: 63-72; Fairbanks, A. J. (2013) Pure Appl. Chem. 85, 1847-1863).

Example 1: Cloning, Overexpression and Purification of EndoSd-D232M and EndoSz-D234M and Mutants The genes of EndoSd and EndoSz from *Streptococcus dysgalactiae* subsp. *Dysgalactiae* (ANI26082.1) and *Streptococcus equi* subsp. *Zooepidemicus* Sz105 (KIS14581.1) were used for this study. The signal peptides were deleted in both enzymes at N-terminal. To enhance transglycosylation activity we aligned the EndoSd and EndoSz protein sequence to EndoS-D233Q (Huang, W. et al. (2012) J. Am. Chem. Soc. 134: 12308-12318) and found the relative position is D232 and D234 for EndoSd and EndoSz, respectively. We decided to mutate the relative position D to M. Therefore, the gene encoding amino acids 20-1067 of EndoSd-D232M and 20-1011 of EndoSz-D234M were synthesized and sub-clone into pGEX-4T-1 with 5'-BamHI and 3'-XhoI restriction sites. For the purification purpose, we inserted additional six histidine at the C-terminal of EndoSd-D232M and EndoSz-D234M for affinity Ni-NTA column. Other mutates used in this investigation were generated by site-directed mutagenesis. Related primers were designed ing 50 mM MOPS pH 6.7 and concentrated using TFF (Millipore lab scale) by 30 kDa cutoff cassette. The final samples were assayed by SDS-PAGE and Braford for detecting MW and concentrates, respectively.

Example 2: Deglycosylation of OBI-888 by EndoS-WT and Bf-α-Fucosidase to Generate mAb-GlcNAc and mAb-GlcNAc(F)

The OBI-888 and Herceptin monoclonal antibody (10 mg) were incubated with EndoS (10 µg) in a 25 mM sodium citrate buffer (pH 6.5) and 100 mM NaCl at 37° C. for 4 h. The complete cleavage of Fc N-glycans was analyzed by 4-12% gradient SDS-PAGE.

The N-glycans of OBI-888 (10 mg) was digesting by incubation with EndoS-WT (10 µg) and Bf-α-fucosidase (10 mg) in the Tris-HCl buffer (pH 7.4) at 37° C. for 16 hours to generate OBI-888-GlcNAc. The commercial antibodies Herceptin (trastuzumab), Perj eta (pertuzumab), Erbitux (cetuximab), Rituxan (rituximab), Vectibix (panitumumab), Humira (adalimumab), Keytruda (pembrolizumab) and Bavencio (avelumab) (10 mg) used the same procedure as OBI-888 except temperature at 30° C. The complete cleavage of Fc N-glycans was analyzed by 4-12% gradient SDS-PAGE. Fucosylated mAb-GlcNAc (mAbs-GlcNAc-F) were produced by only EndoSz wild type in similar condition with 4 hours incubation time.

Example 3: Tansglycosylation of Glycans to mAb-GlcNAc and mAb-GlcNAc-F

In general procedures, mAb-GlcNAc/mAb-GlucNAc-F (5 mg) was incubated with glycan-oxa with molar ratio 1:20 and 1:150 (mAb-GlcNAc:NSCT-oxa) by EndoSz-D234M (167 μg) or EndoSd-D232M (1002 μg), respectively, at 30° C. for 20 minutes in a MOPS buffer (50 mM, pH 6.7), to final volume 500 μL. There were some slight modifications according to experiment purposes and designs (see result section). HLPC was employed to monitor the transglycosylation efficiency.

Example 4: Purification of Deglycosylated and Homogeneous mAb

The reaction mixture was applied to a HiTrap Protein-A HP (5 mL, GE) prepack column which pre-equilibrated with PBS buffer. The non-bound contaminations were washed by two steps pH gradient, PBS (pH 7.4) buffer and glycine-HCl (pH 5.0) buffer, with five times of column volume in each step. Sodium citrate (pH 3.0) was employed to elute bound antibody. The eluted fractions were immediately neutralized with Tris-HCl buffer (1M, pH 9.0) to pH 7.4 and dialyzed to the storage buffer containing 50 mM MOPS (pH 6.7) for mAb-GlcNAc(F) and 5 mM Histidine and 150 mM Nacl for mAb-G2S2, respectively, with 30 kDa cutoff dialysis cassette (Thermo) overnight at 4° C. All samples were concentrated by Amicon centrifugation membrane (30 kDa cutoff, Millipore) and storage at 4° C. [mAb-GlcNAc(F)] or −80° C. [mAb-G2S2(F)].

Example 5: LC/MS/MS of Glycopeptide Analysis

Samples were first processed for buffer exchange into ddH$_2$O by 10 kDa cut-off Amicon Ultra-0.5 device. Samples were denatured in 0.1% RapiGest SF solution/50 mM triethylammonium bicarbonate (TEABC), reduced with 5 mM Dithiothreitol (DTT) at 60° C. for 30 minutes, then alkylated using 15 mM iodoacetamide in dark at room temperature for 30 minutes. The resulting samples were subjected to in-solution digestion with trypsin (trypsin: sample protein=1:30) in 50 mM TEABC at 37° C. overnight. After digestion, the samples were acidified with 0.5% trifluoroacetic acid (TFA) (v/v) and incubated at 37° C. for 45 minutes. The acid treated samples were centrifuged at 4° C., 14000 rpm for 30 minutes to precipitate the hydrolytic RapiGest SF by-product. The samples were analyzed with Thermo Q-Exactive mass spectrometer (Thermo Scientific) coupled with Ultimate 3000 RSLC system (Dionex). The LC separation was performed using the C18 column (Acclaim PepMap RSLC, 75 μm×150 mm, Thermo) with mobile phase A: 0.1% FA (Formic acid) and B: 95% ACN (acetonitrile)/0.1% FA and Table 2 listed the analysis solvent gradient.

TABLE 2

| Solvent gradient of LC | | | |
|---|---|---|---|
| Time (min) | A % | B % | Flow (μL/min) |
| 0 | 99 | 1 | 0.25 |
| 5.5 | 99 | 1 | 0.25 |
| 45 | 75 | 25 | 0.25 |
| 48 | 40 | 60 | 0.25 |
| 50 | 20 | 80 | 0.25 |
| 60 | 20 | 80 | 0.25 |
| 65 | 99 | 1 | 0.25 |
| 70 | 99 | 1 | 0.25 |

Full MS scan was performed with m/z range of 300 to 2000 and the ten most intense ions from MS scan were selected for MS/MS scans.

Example 6: Enzymatic Conjugation Assay by HPLC

The glycosynthase activity was analyzed by HPLC (Waters e2695) using 2.1×150 mm UPLC Glycoprotein Amide Column (Waters) under two different buffers (Buffer A, ddH$_2$O/0.3% v/v HFIP (1,1,1,3,3,3-Hexafluoro-2-propanol), 0.1% v/v TFA; Buffer B, ACN, 0.3% v/v HFIP, 0.1% v/v TFA) with the gradient as Table 3.

TABLE 3

| Solvent gradient of HPLC | | | |
|---|---|---|---|
| Time | Flow (mL/min) | A (%) | B (%) |
| 0.00 | 0.20 | 15 | 85 |
| 0.50 | 0.20 | 15 | 85 |
| 1.00 | 0.20 | 33 | 67 |
| 17.0 | 0.20 | 38.6 | 61.4 |
| 20.0 | 0.20 | 38.6 | 61.4 |
| 21.0 | 0.20 | 15 | 85 |
| 30.0 | 0.20 | 15 | 85 |

Before experiment the column was washed by 50% ACN and 50% of ddH$_2$O for 30 minutes and equilibrated with 15% buffer A and 85% buffer B until the system pressure was stable. After ensuring the baseline stability by injection water blank, the process was started by 2 μL sample injection. In the process duration (29 mins), the flow rate was 0.2 mL/min under the column temperature of 65° C. and sample tray temperature of 5° C.

Example 7: ADCC Assay of the Engineered Antibody

The ADCC activity was analyzed by ADCC reporter bioassay complete kit (Promega, G7015) using luciferase reporter cells. The related cell lines MCF7W (OBI-888), SKBR-3 (Herceptin, Perjeta), BxPC3 (Erbitux) and Raji (Rituxan) were selected for the analysis. Cell lines shared with the same procedures. Target cells were seeded at 96-well cell culture plate and incubated overnight at 37° C. in a humidified 5% CO$_2$ incubator. The culture medium was replaced with serial dilution of homogeneous antibody and the corresponding antibody standard in triplicate. In each well, ADCC bioassay effector cells were added. Ratio of effector cell to target cell was 3:1. We performed induction for 6 hours and then added of Bio-Glo luciferase assay buffer. After 15 minutes, luminescence (RLU, relative light unit) was determined using microplate reader (SpectraMax L, Molecular Devices, Sunnyvale, Calif.). The fold change of luminescence induction was calculated by the ratio of relative light unit (RLU) (induced) to RLU (no antibody control). EC$_{50}$ was determined by plotting x (concentration in μg/mL)–y (the induction of fold change) and fitting the data in a 4PL nonlinear regression model by PRISM 6 Software. Relative potency was estimated by parallel line analysis using Gen5 Microplate Reader and Imager Software (BioTek Instruments).

Example 8: Cleavage and Conjugation of Herceptin

Figure 2:
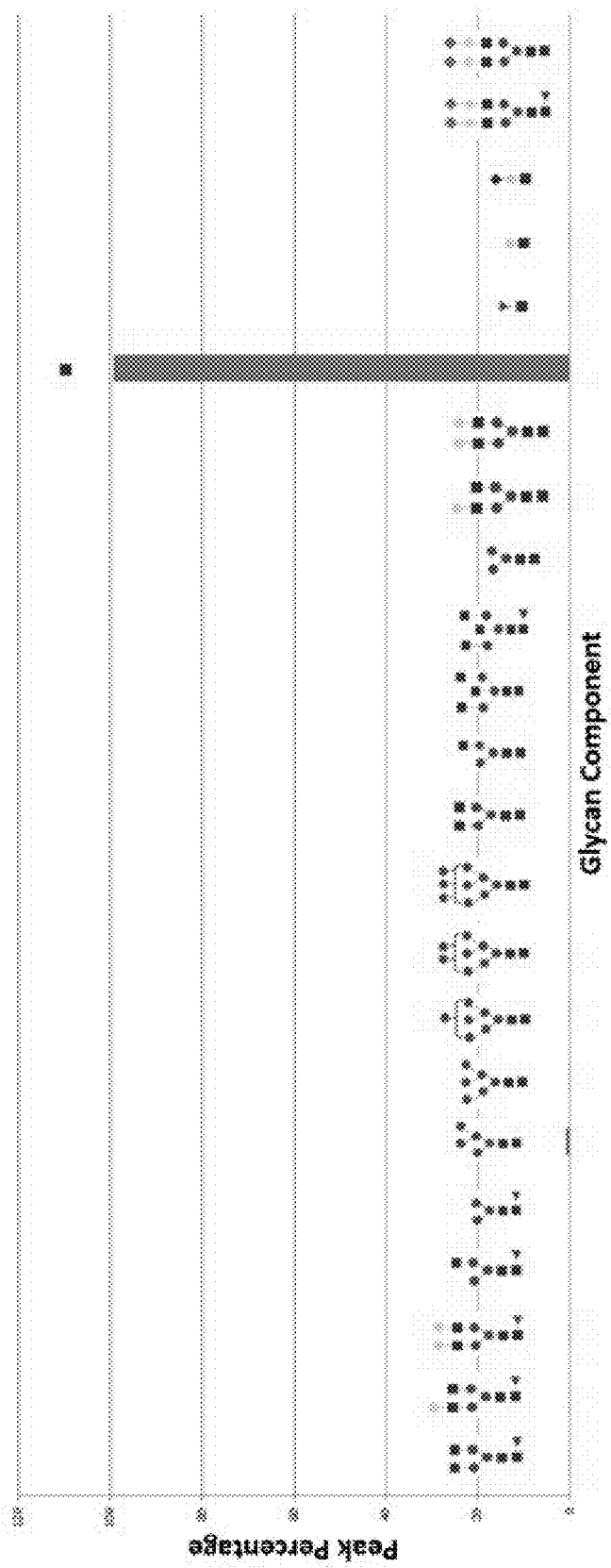
FIG. 2. LC/MS/MS results of Herceptin-GlcNAc glycopeptide. The Herceptin wild type was mixed with EndoSz wild type and α-fucosidase to remove the glycans on the Fc region. The result showed all of the glycans were removed and generated >99% Herceptin-GlcNAc.

Antibody produced by CHO cell always contains heterogeneous glycans on the N297 position of Fc. To generate homogeneous mAbs and enhance ADCC, enzymatic modification of glycan cleavage and transglycosylation are essential steps in homogeneous platform (FIG. 1). For the glycan cleavage, it has reported that EndoSd-WT hydrolyzed biantennary glycans but it is not a general chitinase (Shadnezhad, A. et al. (2016) Future Microbiol 11: 721-736). To illustrate the ability of EndoSz-WT, it was used to hydrolyze native Herceptin and detected the N-glycan profile. The result showed EndoSz-WT could hydrolyzed biantennary hybrid and high mannose glycans. It was generated >99% Herceptin with only one N-acetylglycosamine (Herceptin-GlcNAc) on N297 by EndoSz-WT and α-fucosidase enzyme (FIG. 2). However, for the mAb containing glycosylated Fab, we combined additional enzyme, EndoH or EndoM (Shadnezhad, A. et al. (2016) Future Microbiol 11: 721-736; Kadowaki, S. et al. (1990) Agric. Biol. Chem. 54: 97-106), in the cleavage step for the glycan removal completely.

Figure 3:
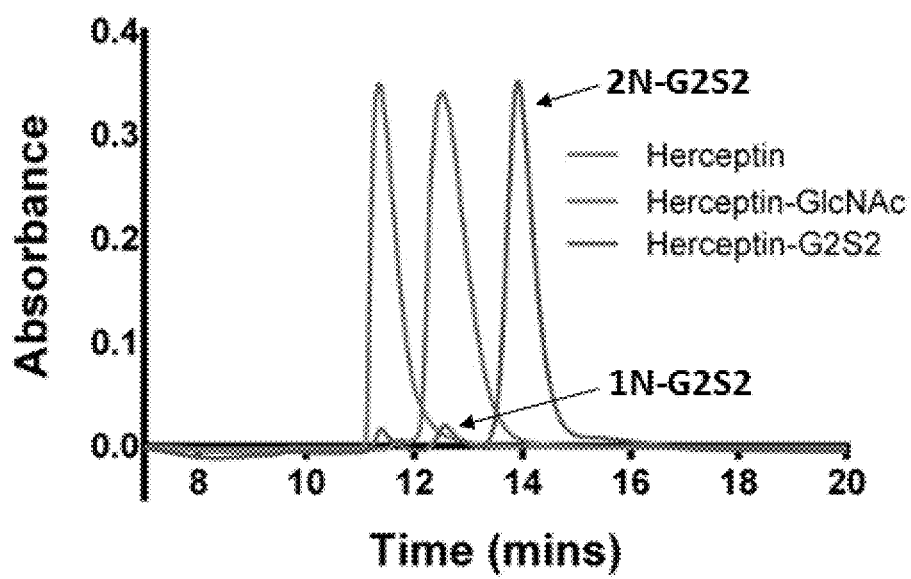
FIG. 3. The exemplary detection methods for homogeneous platform (demonstrated by EndoSz-D234M). (A) The HPLC analysis method. Original Herceptin (green) had retention time 12.5 minute, and Herceptin-GlcNAc (magenta) shifted to 11.4 minute. In the transglycosylation of NSCT-oxa, the Herceptin-G2S2 (blue) could be clearly distinguished by 1N-G2S2 (hemi-glycosylated) and 2N-G2S2 (fully glycosylated) with retention time 12.6 and 13.9 minute, respectively. In the transglycosylation process, the peaks sequentially shifted from Herceptin-GlcNAc to Herceptin-1N-G2S2 and Herceptin-2N-G2S2, which allowed us to monitor the process. (B) The SDS-PAGE result for comparison. Hemi-glycosylated and fully glycosylated Herceptin-G2S2 could not be easy identified.
Figure 3:
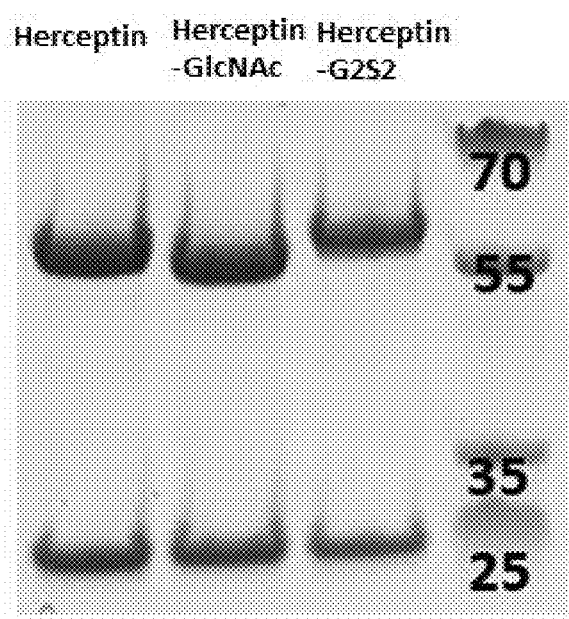

ENGases also have glycan conjugation function with proper mutations (Huang, W. et al. (2012) J. Am. Chem. Soc. 134: 12308-12318; Li., T., Tong, et al. (2016) J. Biol. Chem. 291: 16508-16518). We have established the HPLC method with amide column for precisely monitoring the transglycosylation process. As the example showed in FIG. 3, native Herceptin had retention time at 12.5 minute. After EndoSz-WT and α-fucosidase cleavage, the retention time of Herceptin with one GlcNAc (Herceptin-GlcNAc) was shifted to 11.4 minute and had the calculated molecular mass MW=145,572 Da by intact mass analysis. In the tranglycosylation step of oxazoline sialylated complex type N-glycan (NSCT-oxa) to Herceptin-GlcNAc (demonstrated by EndoSz-D234M), it is interesting to note that the column could clearly identify hemi-glycosylated Herceptin (Herceptin-1N-G2S2) and fully-glycosylated Herceptin (Herceptin-2N-G2S2) that could not be distinguished in the SDS-PAGE. Herceptin-1N-G2S2 was found in the retention time at 12.6 minute with MW=147,574 Da, whereas Herceptin-2N-G2S2 had retention time at 13.9 minute with M=149,576 Da. The HPLC method is able to apply to all mAbs. Therefore, we used HPLC assay for further investigation.

Example 9: Transglycosylation Investigation of EndoSz-D234M and EndoSd-D232M

Figure 4:
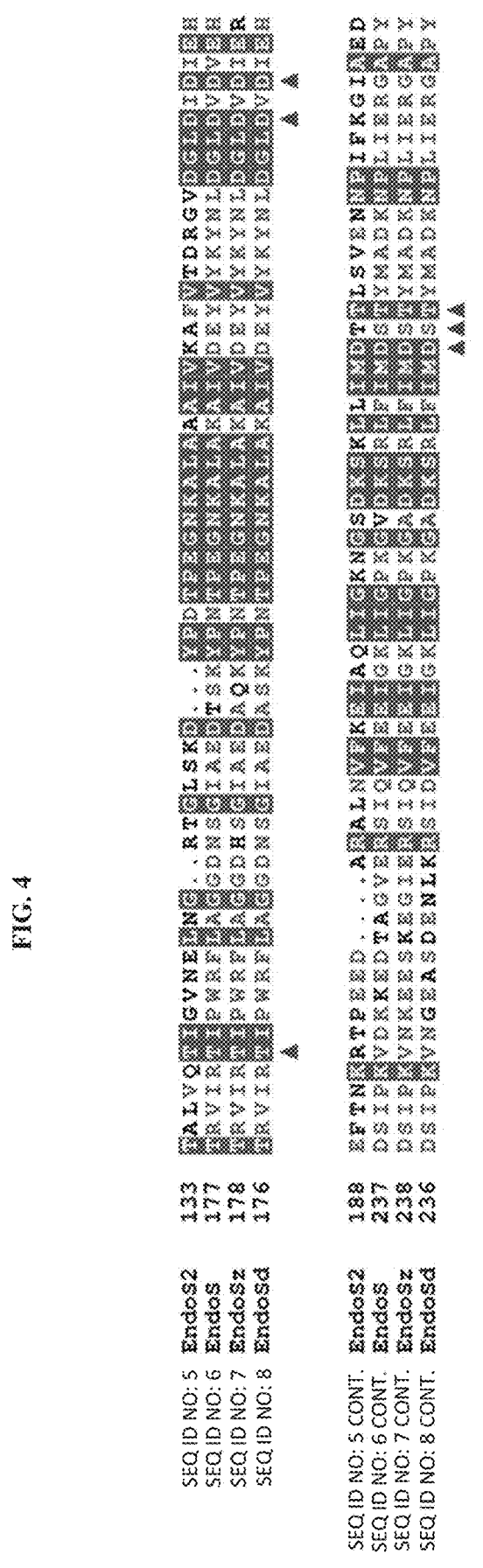

Transglycosylation is the most important step in homogeneous platform that decides the quality of homogeneous mAbs. According to previous report (Li., T., Tong, et al. (2016) J. Biol. Chem. 291: 16508-16518), EndoS2 employed D184M mutation had high transglycosylation activity. We have first generated EndoSz-D234M and EndoSd-D232M for the transglycosylation investigation by multiple sequence alignment (FIG. 4). In general, higher sugar ratio would generate higher conjugation efficiency. However, in industry used, decreasing sugar amount to save cost and processing with a reasonable time frame were the goals for optimizing the process. We used Herceptin-GlcNAc and NSCT-oxa as an investigate model to evaluate the transglycosylation activity of EndoSz-D234M and EndoSd-D232M within 60 minutes and expected the formation of >90% Herceptin-2N-G2S2.

Figure 5:
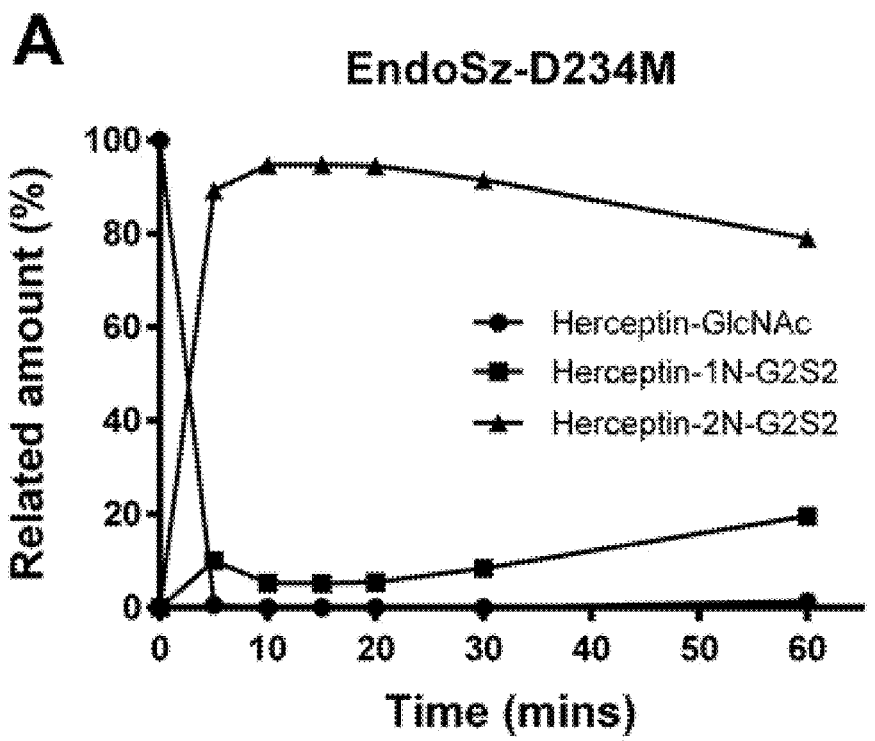
FIG. 5. The time dependent transglycosylation results (A) The transglycosylation of NSCT-oxa and Herceptin-GlcNAc with molar ratio 20:1 by EndoSz-D234M. (B) EndoSd-D232M used higher molar ratio 150:1 (NSCT-oxa: Herceptin-GlcNAc). The reaction was stated with 100% Herceptin-GlcNAc. According to the efficiency, the percentage of Herceptin-1N-G2S2 and Herceptin-2N-G2S2 were formed. Tansglycosylation efficiency of >90% Herceptin-2N-G2S2 could be reached in both enzymes.
Figure 5:
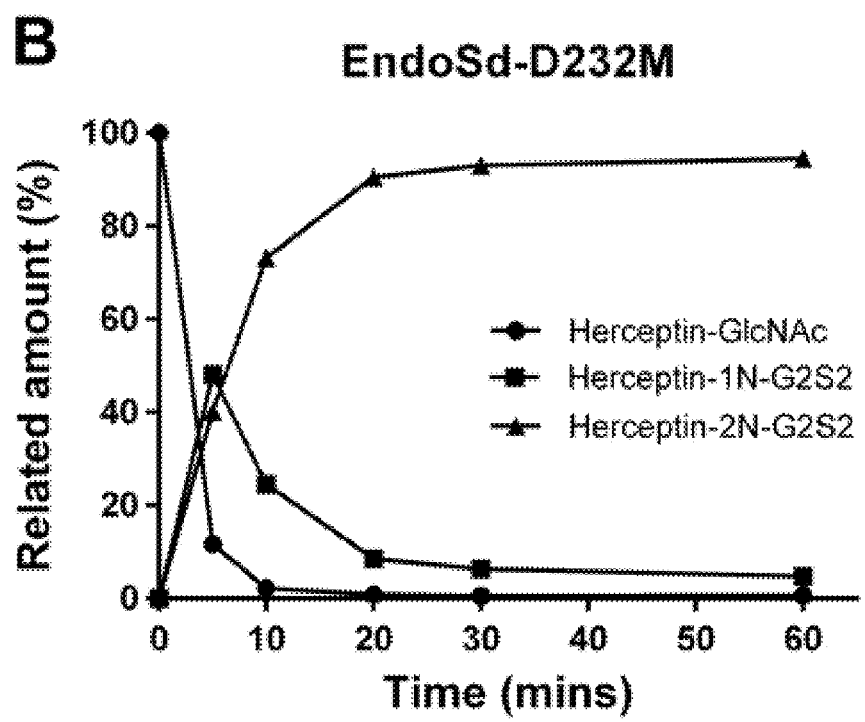

Starting with NSCT-oxa/Herceptin molar ratio of 40:1, >90% Herceptin-2N-G2S2 was obtained with EndoSz-D234M. Decrease the amount of NSCT-oxa/Herceptin molar ratio of 30:1, >90% Herceptin-2N-G2S2 reached at 10 minutes. With 20:1 of NSCT-oxa/Herceptin ratio, Herceptin-2N-G2S2 reached to 89.31% at 5 minutes, reached to 91.85% at 10 minutes and stayed until 20 minutes before deglycosylating (FIG. 5A). With 10:1 of NSCT-oxa/Herceptin (molar ratio), 62.61% of Herceptin-2N-G2S2 were obtained at 5 minutes, 61.48% at 10 minutes and deglycosylation started. To determine extremity of NSCT-oxa usage, increase amount of NSCT-oxa/Herceptin to 15:1 (molar ratio). 80.8% of Herceptin-2N-G2S2 was attained at 5 minutes, and deglycosylation started at 10 minutes. Therefore, the final condition of transglycosylation with EndoSz-D234M enzyme was NSCT-oxa:antibody=20:1 (molar ratio) with 20 minutes reaction time.

The time dependent graph of EndoSz-D234M (FIG. 5A) clearly illustrated the enzyme behavior. It is an efficiency enzyme that quickly bound to Fc and conjugated glycan to N297 position of Fc as we saw that within five minutes Herceptin-GlcNAc decreased almost to 0% and most of fully glycosylated antibody was found. However, the high efficiency transglycosylation enzyme also contributes to hydrolysis activity. In all trails, deglycosylation occurred while the reaction reached the peak efficiency of transglycosylaiton and stay for a period of time (20 minutes), which indicated the importance of controlling the time frame in the process. Notably, the data showed decreasing percentage of Herceptin-2N-G2S2 accompanied by increasing major percentage of Herceptin-1N-G2S2 and minor percentage of Herceptin-GlcNAc, implying the enzyme has priority to select the targets in the hydrolysis reaction.

In contrast, applying the final transglycosylation condition of EndoSz-D234M onto EndoSd-D232M enzyme showed inconsistent results. Only 46.06% Herceptin-2N-G2S2 was generated by EndoSd-D232M with molar ratio 20:1 (NSCT-oxa/antibody), which demonstrated a better glycosynthase activity of EndoSz-D234M. In order to obtain higher fully glycosylated antibody, increasing amount of EndoSd-D232M and NSCT-oxa were the strategies to enhance transglycosylation efficiency. By increasing enzyme amount five times, it was too poor to meet our expected efficiency (>90%) by only 60% Herceptin-2N-G2S2 produced. Therefore, we tried to increase NSCT-oxa amount to 80:1 (molar ratio) and give an unstable result with the range of 80-90% Herceptin-2N-G2S2. Finally, 150:1 (molar ratio) of NSCT-oxa gave a stable and repeatable data. The time dependent graph (FIG. 5B) showed that the EndoSd-D232M slowly transferred NSCT-oxa to N297 (Fc region) despite larger amount of substrate was used. In 5 minutes, the Herceptin-1N-G2S2 (~50%) has larger amount than Herceptin-2N-G2S2 (~40%). Herceptin-2N-G2S2 reached to 80% at 10 minutes and 94% at 20 minutes. The deglycosylation was not found within 60 minutes.

Besides using Herceptin-GlcNAc as acceptor, we also studied transglycosylation activity of fucosylated Herceptin-GlcNAc (Herceptin-GlcNAc-F) that potentially applies in Antibody-Drug-Conjugation (ADC). Using the best transglycosylation conditions described previously, it was obtained 94.29% and 94.75% Herceptin-2N-G2S2F by EndoSz-D234M and EndoSd-D232M, respectively (Table 4). It has demonstrated that two enzymes have transglycosylation activity on fucosylated substrate.

Table 4. The transglycosylation results of EndoSz-D234M and EndoSd-D232M in different acceptors.

TABLE 4

The transglycosylation results of EndoSz-D234M and EndoSd-D232M in different acceptors.

| Enzyme | Acceptor | GlcNAc(F) | 1N-G2S2 | 2N-G2S2 |
|---|---|---|---|---|
| EndoSz-D234M | Herceptin-GlcNAc | 3.35% | 4.8% | 91.85% |
|  | Herceptin-GlcNAc-F | 1.72% | 4.00% | 94.29% |
| EndoSd-D232M | Herceptin-GlcNAc | 0% | 2.11% | 97.88% |
|  | Herceptin-GlcNAc-F | 0% | 3.17% | 94.75% |

In conclusion, EndoSz-D234M has a better transglycosylation activity than EndoSd-D232M. EndoSz-D234M stable produced >90% Herceptin-2N-G2S2 (Herceptin-2N-G2S2F) with only 20:1 molar ratio (NSCT-oxa:antibody), whereas EndoSd-D232M needs 7.5 folds of substrate Example 10: Transglycosylation Investigation of EndoSz and EndoSd Mutates The previous reports that several mutant sites, such as EndoS-D233Q and EndoS2-D184M could increase transglycosylation activity for glycan (Huang, W. et al. (2012) J. Am. Chem. Soc. 134: 12308-12318; Li., T., Tong, et al. (2016) J. Biol. Chem. 291: 16508-16518). Recently, Shivatare et al. reported that the mutation of EndoS2-T138Q increases better activity than EndoS2-D184M (Shivatare, S. S. et al. (2018) Chem. Commun. 54, 6161-6164). According to multiple sequence alignment (FIG. 4), the equivalent positions T183, D232, D234, D280, S281 and T282 of EndoSz, and T181, D230, D232, D278, S279 and T280 of EndoSd were selected as targets for site-directed mutagenesis investigation, in which EndoSz D234 and EndoSd D232 sites were generated by several different types, including positive/negative charge and polar/non-polar. The transglycosylation activity was assayed using the best conditions described previous.

Figure 6:
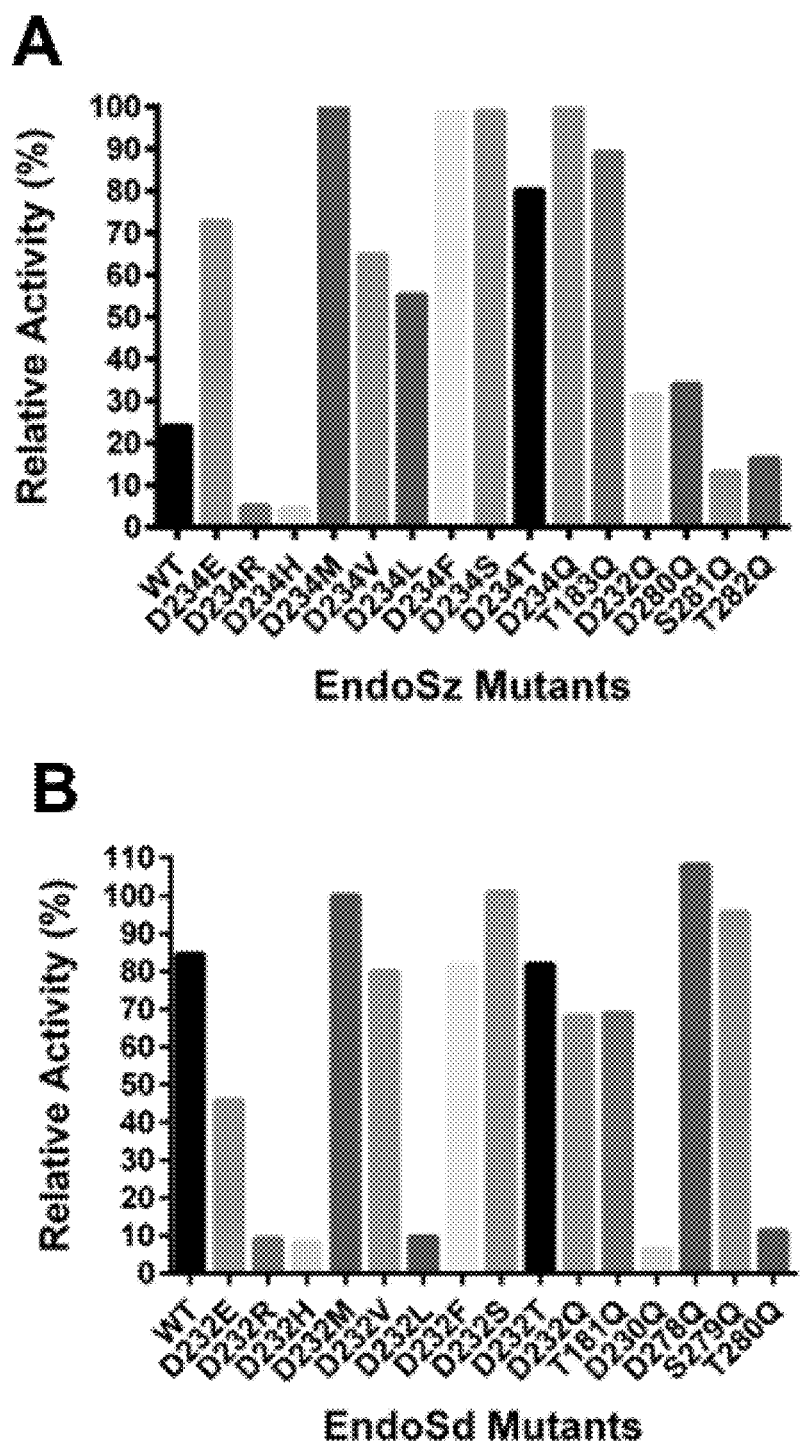
FIG. 6. The relative transglycosylation activities in different exemplary mutants. (A) EndoSz (B) EndoSd.

The activity assay results of EndoSz mutants (FIG. 6A) showed that EndoSz-D234M has highest activity (set to 100%) and EndoSz-D234Q (99.9%), EndoSz-D234S (98.8%) and D234F (98.6%) have competitive high activities. In contrast, EndoSz-D234R (4.9%) and EndoSz-D234H (4.5%) have low activities. EndoSz wild type also has sight transglycosylation activity (24.3%). Beside the D234 position, EndoSz-T183Q (89.1%), EnodSz-D232Q (31.4%), EndoSz-D280Q (34.0%), EndoSz-S281Q (12.9%) and EndoSz-T282Q (16.3%) had no significant increasing transglycosylation activity compared to EndoSz-D234M.

In EndoSd mutants (FIG. 6B), EndoSd-D232M (set to 100%), EndoSd-D232S (100.8%) and EndoSd-D278Q (108.0%) have equally high transglycosylation activity, whereas EndoSd-D232R (9.2%) and EndoSd-D232H (8.1%) have low activities. The EndoSd wild type had relatively high transglycosylation activity (84%).

In conclusion, EndoSz-D234M and EndoSd-D278Q were shown to exhibit relative better transglycosylation activity on Herceptin-GlcNAc to produce homogeneous Herceptin bearing with NSCT-oxa at the Fc region.

Example 11: Conjugation Investigation of EndoSz-D234M on Various Sugars

Homogeneous platform was designed to conjugate various glycans on Fc region of Herceptin. Glycans, M3, G0 and G2, were used for the investigation by better effective enzyme, EndoSz-D234M. The results showed all of the glycans were successfully conjugated onto Fc region with 20:1 molar ratio (NSCT-oxa:antibody). G0 and G2 except M3 reached to >90% fully glycosylated Herceptin (Table 5).

TABLE 5

The transglycosylation results of EndoSz-D234M in different acceptor with different glycans.

| Acceptor | Glycan type | GlcNAc(F) | 1N-Glycan | 2N-Glycan |
|---|---|---|---|---|
| Herceptin-GlcNAc | M3 (40 eq) | 1.11% | 6.51% | 92.37% |
| | G0 | 0.91% | 2.58% | 96.50% |
| | G2 | 0.61% | 4.52% | 94.87% |

TABLE 5-continued

The transglycosylation results of EndoSz-D234M in different acceptor with different glycans.

| Acceptor | Glycan type | GlcNAc(F) | 1N-Glycan | 2N-Glycan |
|---|---|---|---|---|
| Herceptin-GlcNAc-F | M3F | 0.62% | 4.95% | 94.44% |
| | G0F | 0.00% | 2.45% | 97.55% |
| | G2F | 0.21% | 2.64% | 97.14% |

M3 was able to obtain 78% fully glycosylated Herceptin at 5 minutes and deglycosylation started. To optimize the conjugation rate, increasing M3 to 30:1 (molar ratio) to attain a result of 86.3% at minute 10 before deglycosylation, and increasing to 40:1 (molar ratio) for 90% of fully glycosylated Herceptin attempt. Final condition of conjugating with M3 was 40:1 with 10 minutes reaction time to obtain 92.37% fully glycosylated Herceptin. Homogeneous platform not only can be applied on Herceptin-GlcNAc but also applied on Herceptin-GlcNAc-F to conjugating various glycans on Fc region and with results of above 90% conjugation efficiency.

Example 12: Transglycosylation on Various Antibodies

Figure 7:
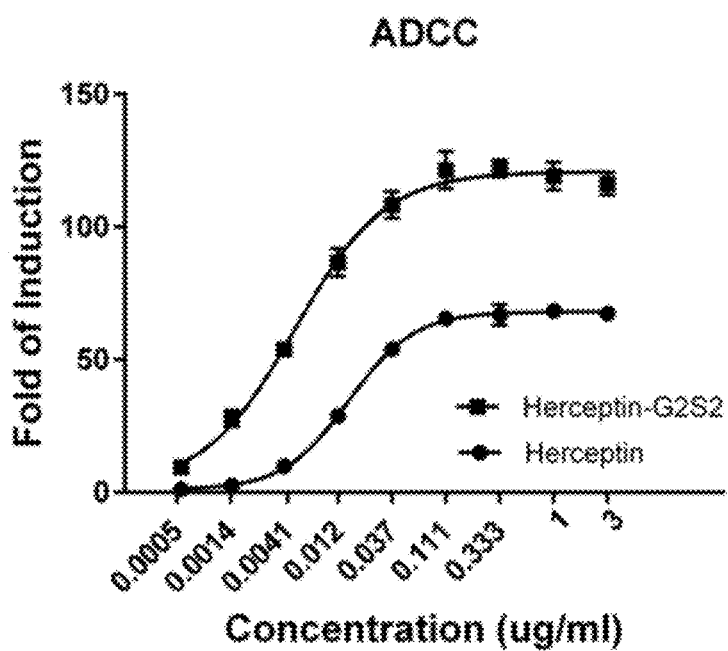
FIG. 7. Demonstration of efficacy: The ADCC assay results. (A) The ADCC result of Herceptin and Herceptin-G2S2. The data showed Herceptin had higher ADCC activity. The $EC_{50}$ of Herceptin and Herceptin-G2S2 was 15.29 (μg/mL) and 5.10 (μg/mL), respectively. (B) The summary of the transglycosylation efficiency and ADCC in various mAb s.

Homogeneous platform is a powerful process to establish homogeneous mAbs. Several other mAbs were selected for the conjugation investigation by EndoSz-D234M, including OBI-888, Perj eta, Erbitux, Rituxan, OBI-898, Vectibix, Humira, Keytruda, Bavencio. With the condition of 20:1 (molar ratio) of NSCT-oxa to antibody, the results demonstrated the effectiveness of homogeneous platform (FIG. 7). The percentage of fully glycosylated mAbs are OBI-888-G2S2: 87.57%, Perjeta-G2S2: 92.49%, Erbitux-G252: 87.92%, Rituxan-G252: 97.57%, OBI-898-G252: 89.73%, Vectibix-G2S2: 86.12%, Humira-G2S2: 93.68%, Keytruda-G252: 75.81% and Bavercio-G2S2: 90.73%.

To evaluate the effect of homogeneous glycan on different mAbs, we have selected five antibodies for the ADCC bioassay (FIG. 7B). It is obviously that the $EC_{50}$ of homogeneous mAbs were increased by comparing with original mAbs. Especially OBI-888 increased 26 folds had the best ADCC improvement.

The present invention discloses selected glycosynthase variants that show excellent transglycosylation activities with a broad range of N-glycans, including high mannose, hybrid and complex types.

In preferred embodiments, N-glycans of high mannose, hybrid and complex types are in an active oxazoline form.

In some embodiments, the high mannose type N-glycans described herein are selected from group consisting of $Man_3GlcNAc$, $Man_5GlcNAc$, $Man_6GlcNAc$, $Man_7GlcNAc$, $Man_8GlcNAc$, and MangGlcNAc. In preferred embodiments, the high mannose type N-glycan is $Man_5GlcNAc$.

In some embodiments, the hybrid type N-glycans described herein comprise at least one α-2,6- or α-2,3 terminal sialic acid on the alpha-1,3 arm, wherein the alpha-1,6 arm contains the trimannose residues.

In some embodiments, the hybrid type N-glycans described herein comprise at least one terminal galactose on the alpha-1,3 arm, wherein the alpha-1,6 arm contains the trimannose residues.

In some embodiments, the hybrid type N-glycans described herein comprise at least one terminal GlcNAc on the alpha-1,3 arm, wherein the alpha-1,6 arm contains the trimannose residues.

In some embodiments, the complex type glycans are of bi-, tri- and tetra-antennary complex types.

In some embodiments, the bi-antennary complex type N-glycans described herein comprise at least one α-2,6 or α-2,3 terminal sialic acid. In preferred embodiments, the N-glycans comprise two α-2,6 and/or α-2,3 terminal sialic acids.

In some embodiments, the bi-antennary complex type N-glycans described herein comprise at least one terminal galactose or GlcNAc. In preferred embodiments, the N-glycans comprise two terminal galactose and/or GlcNAc.

In some embodiments, the bi-antennary complex type N-glycans described herein comprise at least one alpha-1,2-fucose. In preferred embodiments, the N-glycans comprise two alpha-1,2-fucoses.

In some embodiments, the bi-antennary complex type N-glycans described herein comprise at least one alpha-1,3-fucose. In preferred embodiments, the N-glycans comprise two alpha-1,3-fucose.

In some embodiments, the bi-antennary complex type N-glycans described herein comprise bisecting GlcNAc.

In some embodiments, the bi-antennary complex type N-glycans described herein comprise at least one LacNAc repeat unit. In preferred embodiments, the N-glycans comprise two LacNAc repeat units.

In some embodiments, the tri-antennary complex type N-glycans described herein comprise at least one α-2,6 or α-2,3 terminal sialic acid. In preferred embodiments, the N-glycans comprise three α-2-6 and/or α-2,3 terminal sialic acids.

In some embodiments, the tri-antennary complex type N-glycans described herein comprise at least one terminal galactose or GlcNAc. In preferred embodiments, the N-glycans comprise three terminal galactose and/or GlcNAc.

In some embodiments, the complex type glycans are of bi-, and triantennary complex types comprising asymmetric antennae on either the alpha-1,3 or alpha-1,6 arm.

In some embodiments, the hybrid and bi-, and triantennary complex type N-glycans described herein comprise α-2,6 or α-2,3 terminal sialic acid. In other embodiments, the hybrid and bi-, and triantennary complex type N-glycan comprises α-2,6 terminal sialic acid.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

Unless defined otherwise, all technical and scientific terms used herein have the same meanings as commonly understood by one of ordinary skills in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

---

What is claimed is:

1. A mutant of glycosynthase comprising:
   an amino acid sequence of SEQ ID NO: 1 or
   an amino acid sequence SEQ ID NO: 2,
   wherein one or more mutations are in a peptide region located within residues 176-186, residues 225-237, residues 273-289 in the sequence of SEQ ID NO: 1 or in a peptide region located within residues 178-188, residues 227-239, residues 275-291 in the sequence of SEQ ID NO: 2.

2. The mutant of glycosynthase of claim 1, wherein the residue is substituted with a neutral amino acid, hydrophobic amino acid, acidic amino acid or a basic amino acid.

3. A method for preparing an engineered glycoprotein using the glycosynthase mutant of claim 1 or 2 comprising coupling of an activated oligosaccharide to a glycoprotein acceptor.

4. The method according to claim 3, wherein the activated oligosaccharide is a glycan oxazoline.

5. The method according to claim 4, wherein the glycan oxazoline comprises an N-glycan having the following formula:

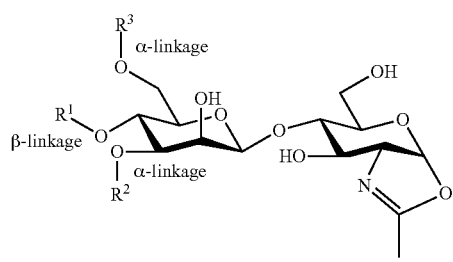

wherein $R^1$ is —H or N-acetyl glucosamine attached via a β-1,4 linkage, and $R^2$ and $R^3$ are same or different and are independently selected from the group consisting of:

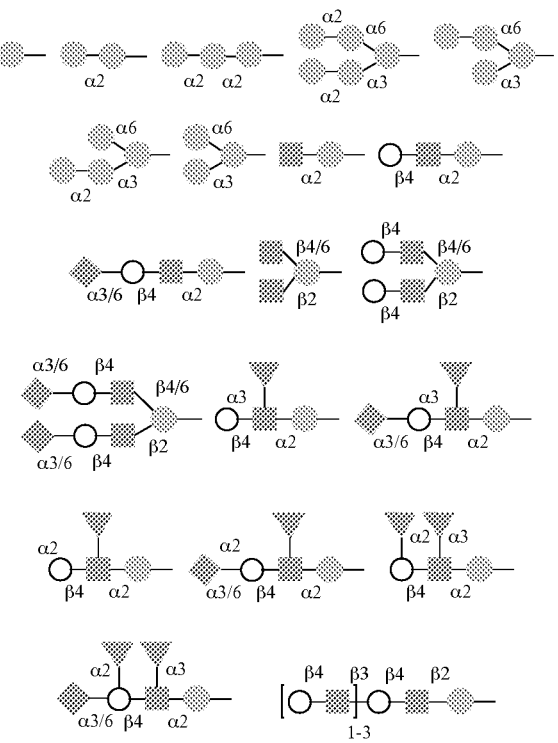

-continued

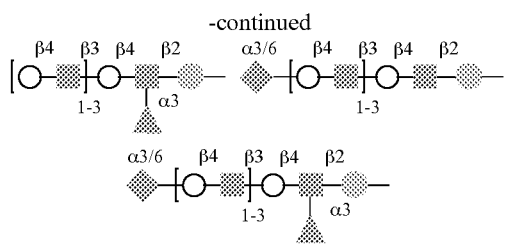

△ Fucose
◆ N-acetylneuraminic acid
○ Galactose
▦ Mannose
▨ N-acetylglucosamine

6. The method according to claim 3, wherein the glycoprotein acceptor contains a GlcNAc monosaccharide.

7. The method according to claim 3, wherein the glycoprotein acceptor is a non-fucosylated GlcNAc-acceptor.

8. The method according to claim 3, wherein the glycoprotein acceptor is a glycopeptide, a glycoprotein, an antibody or a fragment thereof.

9. The method according to claim 3, wherein the glycoprotein acceptor is a core fucosylated or non-fucosylated GlcNAC-IgG acceptor or a fragment thereof.

10. The method according to claim 9, wherein the GlcNAC-IgG acceptor is derived from a monoclonal antibody targeting Globo series antigen, Her-2, CD20, TNF-α, PD-1, PD-L1, and/or EGFR receptor.

11. The method according to claim 10, wherein the Globo series antigen is Globo H, S SEA-4 and/or S SEA-3.

12. The method of claim 10, wherein the monoclonal antibody is Herceptin (trastuzumab), Perjeta (pertuzumab), Erbitux (cetuximab), Rituxan (rituximab), Vectibix (panitumumab), Humira (adalimumab), Keytruda (pembrolizumab) or Bavencio (avelumab).

13. The method of claim 10, wherein the monoclonal antibody is OBI-888 or OBI-898.

14. A glycan engineering enzyme comprising one or more functional domains, comprising:
an amino acid sequence of SEQ ID NO: 1 or SEQ ID NO: 2.

15. The enzyme of claim 14, wherein the amino acid sequence is selected from *Streptococcus equi* or *Streptococcus dysgalactiae*.

* * * * *